US00RE47150E

(19) United States
(12) Reissued Patent
Wang et al.

(10) Patent Number: US RE47,150 E
(45) Date of Reissued Patent: Dec. 4, 2018

(54) OPTIMIZED MONOCLONAL ANTIBODIES AGAINST TISSUE FACTOR PATHWAY INHIBITOR (TFPI)

(71) Applicant: Bayer HealthCare LLC, Whippany, NJ (US)

(72) Inventors: Zhuozhi Wang, Millbrae, CA (US); Junliang Pan, Moraga, CA (US); Joanna Grudzinska-Goebel, Berlin (DE); Christian Votsmeier, Cologne (DE); Jan Tebbe, Cologne (DE); Joerg Birkenfeld, Frankfurt am Main (DE); Nina Wobst, Köln (DE); Simone Brückner, Cologne (DE); Susanne Steinig, Cologne (DE); Peter Scholz, Kleve (DE)

(73) Assignee: Bayer HealthCare LLC, Whippany, NJ (US)

(21) Appl. No.: 15/208,498

(22) Filed: Jul. 12, 2016

Related U.S. Patent Documents

Reissue of:
(64) Patent No.: 9,309,324
Issued: Apr. 12, 2016
Appl. No.: 13/582,401
PCT Filed: Mar. 1, 2011
PCT No.: PCT/US2011/026766
§ 371 (c)(1),
(2) Date: Aug. 31, 2012
PCT Pub. No.: WO2011/109452
PCT Pub. Date: Sep. 9, 2011

U.S. Applications:
(60) Provisional application No. 61/309,290, filed on Mar. 1, 2010.

(51) Int. Cl.
*A61K 39/395* (2006.01)
*C07K 16/38* (2006.01)
*A61K 39/00* (2006.01)

(52) U.S. Cl.
CPC ..... *C07K 16/38* (2013.01); *A61K 2039/505* (2013.01); *C07K 2317/55* (2013.01); *C07K 2317/565* (2013.01); *C07K 2317/76* (2013.01); *C07K 2317/92* (2013.01); *C07K 2319/21* (2013.01)

(58) Field of Classification Search
CPC ..... C07K 16/38; A61K 2039/505
USPC ..... 530/387.3
See application file for complete search history.

(56) References Cited

U.S. PATENT DOCUMENTS 4,075,193 A 2/1978 Campbell et al.
4,093,606 A 6/1978 Coval
4,374,763 A 2/1983 Takagi
4,499,073 A 2/1985 Tenold
4,597,966 A 7/1986 Zolton et al.
4,816,567 A 3/1989 Cabilly et al.
4,877,608 A 10/1989 Lee et al.
5,096,885 A 3/1992 Pearlman et al.
5,217,954 A 6/1993 Foster et al.
5,369,038 A 11/1994 Koike
5,580,856 A 12/1996 Prestrelski et al.
5,608,038 A 3/1997 Eibl et al.
5,654,403 A 8/1997 Smith et al.
5,792,838 A 8/1998 Smith et al.
5,804,557 A 9/1998 Cleland et al.
5,849,700 A 12/1998 Sørensen et al.
5,871,736 A 2/1999 Bruegger et al.
5,902,582 A 5/1999 Hung
5,994,511 A 11/1999 Lowman et al.
6,111,079 A 8/2000 Wylie
6,165,467 A 12/2000 Hagiwara et al.
6,171,587 B1 1/2001 Wun
6,252,055 B1 6/2001 Relton
6,267,958 B1 7/2001 Andya et al.
6,423,316 B1 7/2002 Riesbeck
6,440,426 B1 8/2002 Wheeler et al.
6,525,102 B1 2/2003 Chen et al.
6,593,291 B1 7/2003 Green
6,638,913 B1 10/2003 Speck et al.
6,656,746 B2 12/2003 Sprecher
6,685,940 B2 2/2004 Andya et al.
6,875,432 B2 4/2005 Liu et al.
(Continued)

FOREIGN PATENT DOCUMENTS

CA 2244209 A1 7/1997
CA 2638811 A1 8/2007
(Continued)

OTHER PUBLICATIONS

Abumiya, T. et al. (1995). "An Anti-Tissue Factor Pathway Inhibitor (TFPI) Monoclonal Antibody Recognized the Third Kunitz Domain (K3) of Free-Form TFPI but Not Lipoprotein-Associated Forms in Plasma," *J. Biochem.* 118: 178-182.
Annex to European Communication for European Application No. 09793543.1, dated Apr. 13, 2012, 7 pages.
Annex to European Communication for European Application No. 09793543.1, dated Feb. 27, 2013, 2 pages.
Annex to European Communication for European Application No. 09793543.1, dated Dec. 8, 2016, 7 pages.
Annex to European Communication for European Application No. 09793543.1, dated Apr. 26, 2016, 7 pages.
(Continued)

*Primary Examiner* — Shri Ponnaluri
(74) *Attorney, Agent, or Firm* — Timothy H. Joyce

(57) ABSTRACT

Isolated monoclonal antibodies that bind human tissue factor pathway inhibitor (TFPI) are provided. Isolated nucleic acid molecules encoding monoclonal antibodies that bind TFPI are also contemplated. Pharmaceutical compositions comprising the anti-TFPI monoclonal antibodies and methods of treating deficiencies or defects in coagulation by administration of the antibodies are also provided. Methods of producing the antibodies are also provided.

24 Claims, 5 Drawing Sheets

Specification includes a Sequence Listing.

(56) References Cited

U.S. PATENT DOCUMENTS 6,908,610 B1 6/2005 Sato
7,015,194 B2 3/2006 Kjalke
7,666,413 B2 2/2010 Liu et al.
7,785,595 B2 8/2010 Dagan et al.
8,142,776 B2 3/2012 Liu et al.
8,318,161 B2 11/2012 Esue
8,450,275 B2 5/2013 Dockal et al.
8,481,030 B2 * 7/2013 Wang et al. ..... 424/133.1
8,613,919 B1 12/2013 Ma et al.
8,632,778 B2 1/2014 Kakuta et al.
9,084,777 B2 7/2015 Morichika et al.
9,309,324 B2 4/2016 Wang et al.
2002/0031799 A1 3/2002 Stafford
2002/0045571 A1 4/2002 Liu et al.
2002/0082206 A1 6/2002 Leach
2002/0160934 A1 10/2002 Broadus
2002/0197605 A1 12/2002 Nakagawa
2003/0004324 A1 1/2003 Rosen
2003/0028920 A1 2/2003 Altier
2003/0059937 A1 3/2003 Ruben
2003/0064491 A1 4/2003 Farnet
2003/0073638 A1 4/2003 Kjalke
2003/0092607 A1 5/2003 Carpenter et al.
2003/0092622 A1 5/2003 Sato et al.
2003/0113316 A1 6/2003 Kaisheva et al.
2003/0118583 A1 6/2003 Emery et al.
2003/0138416 A1 7/2003 Lau
2003/0138417 A1 7/2003 Kaisheva et al.
2003/0157082 A1 8/2003 Hunter
2003/0166004 A1 9/2003 Gyuris
2003/0180287 A1 9/2003 Gombotz et al.
2003/0190316 A1 10/2003 Kakuta et al.
2003/0232054 A1 12/2003 Tang
2003/0233675 A1 12/2003 Cao
2004/0018200 A1 1/2004 Oliver et al.
2004/0022792 A1 2/2004 Klinke et al.
2004/0029129 A1 2/2004 Wang
2004/0031072 A1 2/2004 La Rosa
2004/0034888 A1 2/2004 Liu
2004/0037803 A1 2/2004 Sato
2004/0038878 A1 2/2004 Tanikawa et al.
2004/0052799 A1 3/2004 Smith
2004/0081092 A1 4/2004 Rhee et al.
2004/0091974 A1 5/2004 Tawara et al.
2004/0123343 A1 6/2004 La Rosa
2004/0171538 A1 9/2004 Sicard
2004/0172684 A1 9/2004 Kovalic
2004/0191243 A1 9/2004 Chen et al.
2004/0197324 A1 10/2004 Liu et al.
2004/0214272 A1 10/2004 La Rosa
2004/0228862 A1 11/2004 Shelton et al.
2005/0004354 A1 1/2005 Salfeld
2005/0049403 A1 3/2005 Thompson et al.
2005/0058649 A1 3/2005 Landes
2005/0108791 A1 5/2005 Edgerton
2005/0118163 A1 6/2005 Mizushima et al.
2005/0118643 A1 6/2005 Burgess
2005/0158313 A1 7/2005 Rosen
2005/0175603 A1 8/2005 Liu et al.
2005/0186202 A1 8/2005 Kashmiri
2005/0203280 A1 9/2005 McMichael
2005/0208558 A1 9/2005 Venter
2005/0260581 A1 11/2005 Fontana
2006/0003425 A1 1/2006 Kroger
2006/0019260 A1 1/2006 Lerner
2006/0024297 A1 2/2006 Wood
2006/0034821 A1 2/2006 Kline
2006/0041961 A1 2/2006 Abad
2006/0051347 A1 3/2006 Winter
2006/0068386 A1 3/2006 Slesarev
2006/0075522 A1 4/2006 Cleveland
2006/0107345 A1 5/2006 Alexandrov
2006/0127395 A1 6/2006 Arvinte et al.
2006/0182740 A1 8/2006 Yang et al.
2006/0234912 A1 10/2006 Wang
2006/0246071 A1 11/2006 Green
2006/0251658 A1 11/2006 Ledbetter
2006/0263363 A1 11/2006 Ferlin
2006/0268824 A1 11/2006 Dhesikan et al.
2006/0277280 A1 12/2006 Craggs
2007/0020255 A1 1/2007 Ueno et al.
2007/0020624 A1 1/2007 Rubenfield
2007/0020625 A1 1/2007 Duchaud
2007/0021600 A1 1/2007 Doucette-Stamm
2007/0042383 A1 2/2007 Kapur
2007/0044171 A1 2/2007 Kovalic
2007/0053871 A1 3/2007 Li et al.
2007/0053900 A1 3/2007 Liu et al.
2007/0061916 A1 3/2007 Kovalic
2007/0065439 A1 3/2007 Green
2007/0072177 A1 3/2007 Bakker
2007/0083334 A1 4/2007 Mintz
2007/0086433 A1 4/2007 Cunetto et al.
2007/0116700 A1 5/2007 Liu et al.
2007/0118916 A1 5/2007 Puzio
2007/0122402 A1 5/2007 Bolli et al.
2007/0150938 A1 6/2007 Moon et al.
2007/0184050 A1 8/2007 Ishikawa et al.
2007/0202552 A1 8/2007 Sidhu
2007/0202566 A1 8/2007 Bornscheuer
2007/0224627 A1 9/2007 Horowitz
2007/0271630 A1 11/2007 Boukharov
2008/0008719 A1 1/2008 Bowdish
2008/0025980 A1 1/2008 Hardy
2008/0050774 A1 2/2008 Berka
2008/0056151 A1 3/2008 Gazier et al.
2008/0071063 A1 3/2008 Allan et al.
2008/0095775 A1 4/2008 Lewis
2008/0148432 A1 6/2008 Abad
2008/0287309 A1 11/2008 Bowdish
2009/0169544 A1 7/2009 Nilsson et al.
2009/0169581 A1 7/2009 Sandrine
2009/0280129 A1 11/2009 Liu et al.
2009/0291076 A1 11/2009 Morichika et al.
2010/0158898 A1 6/2010 Liu et al.
2010/0173847 A1 7/2010 Dockal
2010/0239567 A1 9/2010 Esue
2012/0064086 A1 3/2012 Liu et al.
2012/0269817 A1 * 10/2012 Wang ..... A61K 39/3955
424/142.1
2013/0136733 A1 5/2013 Parshad et al.
2014/0294832 A1 10/2014 Wang et al.
2015/0030591 A1 1/2015 Xiang et al.
2015/0209431 A1 7/2015 Ma et al.
2017/0342162 A1 11/2017 Wang et al.

FOREIGN PATENT DOCUMENTS

EP 0025719 A2 3/1981
EP 0187712 A2 7/1986
EP 0303746 A1 2/1989
EP 0303746 B1 11/1992
EP 0531539 A1 3/1993
EP 0539975 A1 5/1993
EP 0579101 A1 1/1994
EP 0661060 A2 7/1995
EP 0787497 A2 8/1997
EP 0612251 B1 12/1997
EP 0841067 A1 5/1998
EP 0531539 B1 6/1998
EP 0303746 B2 12/1998
EP 0909564 A1 4/1999
EP 0661060 B1 5/2001
EP 1197221 A1 4/2002
EP 0841067 B1 5/2002
EP 1314437 5/2003
EP 1336410 8/2003
EP 1356829 A2 10/2003
EP 1475100 11/2004
EP 1475101 11/2004
EP 1977763 10/2008
EP 1981824 10/2008
EP 2196476 A1 6/2010
EP 2332995 A1 6/2011

(56) References Cited

FOREIGN PATENT DOCUMENTS

| | | | | |
|---|---|---|---|---|
| EP | 2335725 | A1 | 6/2011 | |
| JP | 06153985 | | 6/1994 | |
| JP | H-06153985 | | 6/1994 | |
| JP | 08075736 | | 3/1996 | |
| JP | H-08075736 | | 3/1996 | |
| WO | WO-1989011297 | | 11/1989 | |
| WO | WO-1990011091 | | 10/1990 | |
| WO | WO-1992007584 | | 5/1992 | |
| WO | WO-1997004801 | | 2/1997 | |
| WO | WO-1997009063 | | 3/1997 | |
| WO | WO-1997026862 | | 7/1997 | |
| WO | WO-1997026909 | | 7/1997 | |
| WO | WO-1997045140 | | 12/1997 | |
| WO | WO-1998022136 | | 5/1998 | |
| WO | WO-1999011091 | | 3/1999 | |
| WO | WO-2001024814 | | 4/2001 | |
| WO | WO-2001064241 | | 9/2001 | |
| WO | WO-2002011753 | | 2/2002 | |
| WO | WO-2002013860 | | 2/2002 | |
| WO | WO-2002017957 | | 3/2002 | |
| WO | WO-2002030463 | | 4/2002 | |
| WO | WO-2002096457 | | 12/2002 | |
| WO | WO-2003009817 | | 2/2003 | |
| WO | WO-2003039485 | | 5/2003 | |
| WO | WO-2003068259 | | 8/2003 | |
| WO | WO-2003072060 | A2 | 9/2003 | |
| WO | WO-2003072060 | A3 | 9/2003 | |
| WO | WO-2004001007 | | 12/2003 | |
| WO | WO-2004007520 | A2 | 1/2004 | |
| WO | WO-2004016286 | | 2/2004 | |
| WO | WO-2004058184 | | 7/2004 | |
| WO | WO-2004091658 | | 10/2004 | |
| WO | WO-2005019266 | | 3/2005 | |
| WO | WO-2005055930 | A2 | 6/2005 | |
| WO | WO-2005123131 | | 12/2005 | |
| WO | WO-2006044908 | | 4/2006 | |
| WO | WO-2006081587 | | 8/2006 | |
| WO | WO-2006083689 | | 8/2006 | |
| WO | WO-2006096345 | A2 | 9/2006 | |
| WO | WO-2006096461 | | 9/2006 | |
| WO | WO-2006096488 | | 9/2006 | |
| WO | WO-2006096489 | | 9/2006 | |
| WO | WO-2006096490 | | 9/2006 | |
| WO | WO-2006096491 | | 9/2006 | |
| WO | WO-2006110883 | | 10/2006 | |
| WO | WO-2007003936 | | 1/2007 | |
| WO | WO-2007019232 | | 2/2007 | |
| WO | WO-2007074880 | | 7/2007 | |
| WO | WO-2007092772 | | 8/2007 | |
| WO | WO-2007147001 | | 12/2007 | |
| WO | WO-2008009545 | | 1/2008 | |
| WO | WO-2008045563 | | 4/2008 | |
| WO | WO-2008071394 | | 6/2008 | |
| WO | WO-2008121615 | | 10/2008 | |
| WO | WO-2008132439 | | 11/2008 | |
| WO | WO-2008157356 | | 12/2008 | |
| WO | WO-2009009407 | | 1/2009 | |
| WO | WO-2009070642 | | 6/2009 | |
| WO | WO-2009077483 | | 6/2009 | |
| WO | 2009080541 | A1 | 7/2009 | |
| WO | WO-2009080541 | | 7/2009 | |
| WO | WO-2009103113 | | 8/2009 | |
| WO | WO-2009120684 | | 10/2009 | |
| WO | WO-2010000721 | | 1/2010 | |
| WO | WO2010017196 | A2 * | 2/2010 | ..... A61K 39/3955 |
| WO | WO-2010017196 | A2 | 2/2010 | |
| WO | WO-2010032220 | | 3/2010 | |
| WO | WO-201071894 | A2 | 6/2010 | |
| WO | WO-2010062896 | | 6/2010 | |
| WO | WO-2010066762 | | 6/2010 | |
| WO | WO-201072687 | A1 | 7/2010 | |
| WO | WO-201072691 | A1 | 7/2010 | |
| WO | WO 2010072687 | A1 | 7/2010 | |
| WO | WO 2010072691 | A1 | 7/2010 | |
| WO | WO-2010017196 | A3 | 11/2010 | |
| WO | WO-2010148337 | | 12/2010 | |
| WO | WO-2011026948 | A1 | 3/2011 | |
| WO | WO-2011104381 | | 9/2011 | |
| WO | WO-2011109452 | | 9/2011 | |
| WO | WO-2012109675 | A1 | 8/2012 | |
| WO | WO-2012135671 | A2 | 10/2012 | |
| WO | WO-2013142153 | A2 | 9/2013 | |
| WO | 2014144577 | A1 | 9/2014 | |
| WO | WO-2016137108 | A1 | 9/2016 | |
| WO | WO-2017029583 | A2 | 2/2017 | |

OTHER PUBLICATIONS

Anti-human TFPI (Kunitz-2), Art No. MW1845, Citation in opposition procedure regarding European Patent EP2379600, submitted Sep. 6, 2016, 1 page.

Arakawa et al. (1991). "Protein-Solvent Interactions in Pharmaceutical Formulations" *Pharmaceutical Research* 8(3): 285-291.

Bajaj et al. (2001). "Structure and Biology of Tissue Factor Pathway Inhibitor", vol. 86, 959-972.

Bam et al. (1995). "Stability of Protein Formulations: Investigation of Surfactant Effects by a Novel EPR Spectroscopic Technique," *Pharmaceutical Research* 12:2-11.

Baugh et al. (1998). "Regulation of Extrinsic Pathway Factor Xa Formation by Tissue Factor Pathway Inhibitor", *J. Biol. Chem.* 273(8): 4378-4386.

Belaaouaj, A. et al. (Mar. 15, 1993). "Revised cDNA Sequence of Rabbit Tissue Factor Pathway Inhibitor", *Thrombosis Research* 69(5): 547-553.

Berglund, L. et al. (2008). "The epitope space of the human proteome", *Protein Science*, 17:606-613.

Benard, S. (Aug. 31, 2016) "Dissociation constant determination for anti-TFPI K2 antibody (Fitzgerald)," Opposition to European Patent No. EP2379600, submitted Aug. 31, 2016, 2 pages.

Berry, J. et al. (2007). "Collaborative studies to establish the first World Health Organization International Standard for detection of human antibody against human platelet antigen-3a," *Vox Sanguinis* 98: 309-315, Opposition to European Patent No. EP2379600, D97, 7 pages.

Bhambhani, et al. (Mar. 2012). "Formulation design and high-throughput excipient selection based on structural integrity and conformational stability of dilute and highly concentrated IgG 1 monoclonal antibody solutions," *J Pharm. Sci.* 101(3):1120-35.

Bolli, et al (May 6, 2010) "2-Imino-thiazolidin-4-one Derivatives as Potent, Orally Active S1P1 Receptor Agonists", vol. 53 No. 10, 4198-4211.

Breen, E.D. et al. (Sep. 2001). "Effect of Moisture on the Stability of a Lyophilized Humanized Monoclonal Antibody Formulation," *Pharmaceutical Research* 18(9): 1345-1353.

Brinkmann T., et al. (1994). "Synthesis of Tissue Factor Pathway Inhibitor in Human Synovial Cells and Chondrocytes Makes Joints the Predicted Site of Bleeding in Haemophiliacs", *Eur.J. Clin. Chem. Clin. Biochem.* 32 (4): 313-317.

Browder, T., et al. (2000). "The Hemostatic System as a Regulator of Angiogenesis", *J. Biol. Chem.* 275(3): 1521-1524.

Brown et al. (May 1996). "Tolerance to Single, but Not Multiple, Amino Acid Replacements in Antibody VH CDR2: A Means of Minimizing B Cell Wastage from Somatic Hypermutation?", vol. 156 No. 6, 3285-3291.

Broze, GJ Jr. et al. (1990). "Regulation of Coagulation by a Multivalent Kunitz-Type Inhibitor", *Biochemistry* 29(33): 7539-7546.

Broze, GJ Jr., et al. (1991). "The Lipoprotein-Associated Coagulation Inhibitor", *Progress in Hemostasis and Thrombosis* 10: 243-268.

Broze, GJ Jr., (1995). "Tissue Factor Pathway Inhibitor and the Revised Theory of Coagulation", *Annu. Rev. Med.* 46: 103-112.

Burgering, M.J.M. et al. (1997). "The Second Kunitz Domain of Human Tissue Factor Pathway Inhibitor: Cloning, Structure Determination and Interaction with Factor Xa", *J. Mol. Biol.* 269: 395-407.

Buzzell et al. (1956). "The effect of charge and ionic strength on the viscosity of ribonuclease"; *J. Phys. Chem.* 60:1204-1207.

(56) References Cited

OTHER PUBLICATIONS

Campbell, A.M. (1984). Monoclonal Antibody Technology, Elsevier Science Publishing Company, Inc., pp. 1-32.
Carmen et al. (2002). Brief Funet. Genomic Proteomic 1(2):189-203.
Carpenter et al. (1997). "Rational Design of Stable Lyophilized Protein Formulations: Some Practical Advice," *Pharmaceutical Research* 14(8):969-975.
Carpenter et al. (2002). "Rational design of stable protein formulations: theory and practice," *Pharm Biotechnol.* 13: 109-33.
Casset, F. et al. (2003). "A Peptide Mimetic of an Anti-CD4 Monoclonal Antibody by Rational Design," *Biochemical and Biophysical Research Communications*, 307: 198-205.
Chang, L. et al. (Sep. 2009, e-pub. Jun. 30, 2009). "Mechanisms of Protein Stabilization in the Solid State," *Journal of Pharmaceutical Science* 98(9):2886-2908.
Chen, Y. et al. (1999). "Selection and Analysis of an Optimized Anti-VEGF Antibody: Crystal Structure of an Affinity-matured Fab in Complex with Antigen", *J. Mol. Biol.* 293: 865-881.
Chen, R. et al. (2003). "ZDOCK: An Initial-Stage Protein-Docking Algorithm", *Proteins: Structure, Function, and Genetics*, 52: 80-87.
Chen, B. et al. (Dec. 2003). "Influence of Histidine on the Stability and Physical Properties of a Fully Human Antibody in Aqueo and Solid Forms" *Pharmaceutical Research* 20(12): 1952-1960.
Certified Copy of U.S. Appl. No. 61/085,980, filed Aug. 4, 2008.
Chowdary, P. et al. (2015). "Safety and pharmacokinetics of anti-TFPI antibody (concizumab) in healthy volunteers and patients with hemophilia: a randomized first human dose trial", *Journal of Thrombosis and Haemostatis*, 13:743-754.
Clackson et al. (1991). *Nature* 352:624-628.
Crawley et al. (Jan. 23, 2008). "The Haemostatic Role of Tissue Factor Pathway Inhibitor", *Arterioscler. Thromb. Vasc. Biol.*, 28: 233-242.
Current LinkedIn profile for Christopher Sykes, Technical Sales at Fitzgerald Industries, accessed on Aug. 6, 2017, located at https://www.linkedin.com/in/christopher-sykes-20373520/, Opposition to European Patent No. EP2379600, D101, 2 pages.
Dahm, A.E. et al. (2005). "A Novel Anticoagulant Activity Assay of Tissue Factor Pathway Inhibitor I (TFPI)", *J. Thromb.Haemost.*, 3(4): 651-658.
Dalakas (1994). "High-dose intravenous immunoglobulin and serum viscosity: risk of precipitating thromboembolic events", *Neurology* 44: 223-226.
Dani et al. (Jun. 2007). "High concentration formulation feasibility of human immunoglobulin G for subcutaneous administration", *J Pharm Sci.*, 96(6): 1504-1517.
Daugherty, A. (2006). "Formulation and Delivery Issues for Monoclonal Antibody Therapeutics," *Advanced Drug Delivery Reviews*, 58: 686-706.
Day, K.C. et al. (1992). "Bacterial Expression, Purification, and Partial Characterization of Amino Acids 94-155 of Human Tissue Factor Pathway Inhibitor (TFPI) as an Inhibitor of Blood Coagulation Factor Xa", *Thrombosis Research* 68: 369-381.
Declaration of Professor David Lane, executed Sep. 1, 2016, Opposition to European Patent No. EP2379600, D55, 98 pages.
Declaration of Dr. Helle Heibroch Petersen, *Binding of mAbTFPI2021/NN mAb2021 and Bayer mAb2A8 to the isolated K2 domain of TFPI*, executed Jul. 20, 2015, Opposition to European Patent No. EP2379600, D70, 10 pages.
Declaration of Dr. Helle Heibroch Petersen, *Kinetic Parameters for the interaction between full-length TFPI with mAbTFPI2021/NN mAb2021, Bayer mAb2A8 and R&D Systems mAb2974*, executed Jul. 20, 2015, Opposition to European Patent No. EP2379600, D71, 10 pages.
Declaration of Dr. Helle Heibroch Petersen, *Determination that specific monoclonal antibodies are capable of binding to individual isolated Kunitz domains of TFPI*, executed Jul. 20, 2015, Opposition to European Patent No. EP2379600, D72, 14 pages.
Declaration of Dr. Helle Heibroch Petersen, *Binding of 2G9F1 and mAbF36 to the K2 domain fo TFPI*, executed Sep. 2, 2016, Opposition to European Patent No. EP2379600, D73, 10 pages.
Declaration of Anirban Adhikari, Ph.D., executed Aug. 25, 2016, Opposition to European Patent No. EP2379600, D88, 14 pages.
Declaration of Dr. Helle Heibroch Petersen, *Kinetic Parameters for the interaction between full-length TFPI with mAbTFPI2021/NN mAb2021, Bayer mAb2A8, R&D Systems mAb2974 and Fitzgerald mAb10R-T142A*, executed Nov. 10, 2016, Opposition to European Patent No. EP2379600, D89, 8 pages.
Declaration of Holger-Magnus Steuber, Ph.D., executed Apr. 21, 2017, Opposition to European Patent No. EP2379600, D94, 14 pages.
Declaration of Ida Hilden, Ph.D., executed Jun. 9, 2017, Opposition to European Patent No. EP2379600, D99, 2 pages.
Declaration of Berit Olsen Krogh, Ph.D. executed Jun. 9, 2017, Opposition to European Patent No. EP2379600, D100, 2 pages.
De Pascalis, R. et al. (2002). Grafting of "Abbreviated" Complementarity-Determining Regions Containing Specificity-Determining Residues Essential for Ligand and Contact to Engineer a Less Immunogenic Humanized Monoclonal Antibody, *The Journal of Immunology* 169: 3076-3084.
Draber et al. (1995). "Stability of Monoclonal IgM Antibodies Freeze-Dried in the Presence of Trehalose," *Journal of Immunological Methods* 181(1): 37-43.
Dockal, M. et al. (2012). "Biological Explanation of Clinically Observed Elevation of TFPI Plasma Levels After Treatment with TFPI-Antagonistic Aptamer BAX 499", *Amer. Soc. Hematology*, Abstract 1104, 54th ASH Annual Meeting and Exposition.
Dockal, M. et al. (2013). "Crystal Structure of Tissue Factor Pathway Inhibitor (TFPI Kunitz Domain 1 and 2 in Complex with an Inhibitory Cyclic Peptide," *Amer. Soc. Hematology*, Abstract 453, 55th ASH Annual Meeting and Exposition.
Dockal, M. et al. (2014). "Small Peptides Blocking Inhibition of Factor Xa and Tissue Factor-Factor VIIa by Tissue Factor Pathway Inhibitor (TFPI)", *J. Biol. Chem.* 289(3): 1732-1741.
Dockal, M. et al. (2013). "Design of a Most Efficient Inhibitor of TFPI by Molecular Fusion of Two Inhibitory Peptides", *Amer. Soc. Hematology*, Abstract 3564, 55th ASH Annual Meeting and Exposition.
Dockal, M. et al. (2014). "A TFPI Inhibitory Half Life Extended Fusion Peptide Proves Efficacy in FVIII Knock Out Mice and Marmoset Monkeys", *Amer. Soc. Hematology*, Abstract 1469, 56th ASH Annual Meeting and Exposition.
Email from Christopher Sykes, Fitzgerald Industries, to Brenda J. Conner regarding TFPI antibody_10R-T142A, Citation in opposition procedure regarding European Patent No. EP2379600, dated Dec. 13, 2011, 2 pages.
Email from Christopher Sykes, Director of Reagent Sales for Fitzgerald Industries to Diana Barrett re 10R-T112A inquiry, Citation in opposition procedure regarding European Patent EP2379600, dated Aug. 19, 2016, 1 page.
Engelmann, B. (Nov. 1, 2004). "Novel Initiation Mechanism of Blood Coagulation by Intravascular Tissue Factor", *Blood, American Society of Hematology US*, 104 (11) Part 2: 78B. (Abstract).
Erhardtsen, E. et al. (1995). "Blocking of Tissue Factor Pathway Inhibitor (TFPI) Shortens the Bleeding Time in Rabbits with Antibody Induced Haemophilia A", *Blood Coagulation and Fibinolysis*, 6: 388-394.
Eswar, N. et al. (2006). "Comparative Protein Structure Modeling Using Modeller", *Current Protocols in Bioinformatics*, Supplement 15, 5.6.1-5.6.30.
Fahey et al. (1938). "The viscosities of solutions of the proteins of horse serum"; *J. Amer. Chem. Soc.* 60:3039-3043.
Final Office Action dated Nov. 19, 2012, for U.S. Appl. No. 13/323,691.
Final Office Action dated Mar. 5, 2014 for U.S. Appl. No. 13/057,728.
Final Office Action dated May 11, 2016 for U.S. Appl. No. 13/057,728.
Final Office Action dated Feb. 10, 2017 for U.S. Appl. No. 13/057,728.
Final Office Action dated May 27, 2014, for U.S. Appl. No. 13/582,401.
Fitzgerald Industries International, "Monoclonal Mouse anti-TFPI antibody 10R-T142A"—product details, 1 page.

(56) References Cited

OTHER PUBLICATIONS

Forastiero, R.R. et al. (2003). Jr. High Titers of Autoantibodies to Tissue Factor Pathway Inhibitor are Associated with the Antiphospholipid Syndrome, *J. Thrombosis and Haemostasis* 1: 718-724.
Further Submissions regarding the Opposition of European Patent No. EP2379600, dated Sep. 5, 2016, 14 pages.
Further Submissions regarding the Opposition of European Patent No. EP2379600, dated Apr. 19, 2017, 8 pages.
Galush, et al. (Mar. 2012). "Viscosity behavior of high-concentration protein mixtures", *J. Pharm Sci.* 101(3): 1012-20.
Garidel et al. (2009, e-pub. Apr. 16, 2009). "A Thermodynamic Analysis of the Binding Interaction Between Polysorbate 20 and 80 With Human Serum Albumins and Immunoglobulins: A Contribution to Understand Colloidal Protein Stabilization," *Biophysical Chemistry* 143:70-78.
Girard, T.J. et al. (1989). "Functional Significance of the Kunitz-type Inhibitory Domains of lipoprotein-associated Coagulation Inhibitor", *Nature* 338: 518-520.
Girard, T.J. et al. (1991). "Structure of the Human Lipoprotein-associated Coagulation Inhibitor Gene", *J. Biol. Chem.*, 266 (8): 5036-5041.
Girard, T.J. et al. (1994). "Complementary DNA Sequencing of Canine Tissue factor Pathway Inhibitor Reveals a Unique Nanomeric Repetitive Sequence between the Second and Third Kunitz Domains", *Biochem. J.*, 303: 923-928.
Giusti et al. (May 1987). "Somatic Diversification of S107 from an Antiphosphocholine to an Anti-DNA Autoantibody is due to a Single Base Change in its Heavy Chain Variable Region", vol. 84, 2926-2930.
Gokarn et al. (2008). "Self-buffering antibody formulations", *J. Pharm. Sci.* 97(8):3051-3066.
Green, L. (1999). "Antibody engineering via genetic engineering of the mouse: XenoMouse strings are a vehicle for the facile generation of therapeutic human monoclonal antibodies", *Journal of Immunological Methods*, 231: 11-23.
Griffiths, A. D. et al. (1998). "Strategies for selection of antibodies by phage display", *Current Opinion in Biotechnology*, 9: 102-108.
Han, Y. et al. (Sep. 2007). "Effects of sugar Additives on Protein Stability of Recombinant Human Serum Albumin during Lyophilization and Storage", *Arch Pharm Res* 30(9):1124-1131.
Hansen, J-B, et al. (1997). "Tissue Factor Pathway Inhibitor in Complex with Low Density Lipoprotein Isolated from Human Plasma Does Not Possess Anticoagulant Function in Tissue Factor-Induced Coagulation in Vitro", *Thrombosis Research* 85(5):413-425.
Hansen, L. et al. (2014). "Target-mediated clearance and biodistribution of a monoclonal antibody against the Kunitz-type protease inhibitor 2 domain of Tissue Factor Pathway Inhibitor", *Thrombosis Research*, 113: 464-471.
Harn et al. (Mar. 2007). "Highly concentrated monoclonal antibody solutions: direct analysis of physical structure and thermal stability", *J Pharm Sci.* 96(3):532-46.
Harris et al. (2004). "Commercial manufacturing scale formulation and analytical characterization of therapeutic recombinant antibodies"; *Drug Dev. Res.* 61:137-154.
He et al. (Nov. 2, 2010 e-pub; Jul. 2011). "Effect of sugar molecules on the viscosity of high concentration monoclonal antibody solutions", *J Pharm Sci.; Pharm Res.* 28(7): 1552-60.
He, F. et al. (Apr. 2010, e-pub. Sep. 24, 2009). "High Throughput Thermostability Screening of Monoclonal Antibody Formulations," *Journal of Pharmaceutical Sciences* 99(4): 1707-1720.
Hess et al. (1950). "The intrinsic viscosity of mixed protein systems, including studies of plasma and serum"; *J. Gen. Physiol.* 33:511-523.
Hilden et al. (Jun. 14, 2012). "Hemostatic effect of a monoclonal antibody mAb 2021 blocking the interaction between FXa and TFPI in a rabbit hemophilia model", *Blood*, 119(24): 5871-5878.
Higuchi, D.A. et al. (1992). "The Effect of Leukocyte Elastase on Tissue Factor Pathway Inhibitor", *Blood* 79: 1712-1719.
Holm, P. et al. (2007). "Functional mapping and single chain construction of the anti-cytokeratin 8 monoclonal antibody TS1", *Molecular Immunology* 44: 1075-1084.
Holma, B. et al. (1989). "pH- and Protein-Dependent Buffer Capacity and Viscosity of Respiratory Muc, Their Interrelationships and Influence on Health," *The Science of the Total Environment* 84:71-82.
Hoogenboom, H. (Feb. 1997). "Designing and optimizing library selection strategies for generating high-affinity antibodies", *Tibtech*, 15: 62-70.
Horie, S. et al. (2000). "Oxidized Low-density Lipoprotein Impairs the Anti-coagulant Function of Tissue-Factor-Pathway Inhibitor Through Oxidative Modification by its High Association and Accelerated Degradation in Cultured Human Endothelial Cells", *Biochem. J.*352: 277-285.
Houston, D.S. (Apr. 2002). "Tissue Factor—A Therapeutic Target for Thrombotic Disorders", *Expert Opin. Ther. Targets*, 6(2): 159-174. (Abstract).
Hu, B. et al. (2009). "Opalescence of an IgG 1 Monoclonal Antibody Formulation is Mediated by Ionic Strength and Excipients," *BioPharm. Int.* 22(4): 36-47.
Internet Archive (Way Back Machine), Sanquin Reagents White Label Products, citation in opposition procedure regarding European Patent No. EP2379600, submitted Sep. 6, 2016, 4 pages.
International Report on Patentability for PCT/US2009/052702 dated Feb. 8, 2011.
International Search Report for PCT/US2009/052702 dated Sep. 13, 2010.
International Search Report for PCT/US2009/052663 dated Sep. 15, 2009, 3 pages.
International Search Report for PCT/US2011/026766 dated Jul. 15, 2011, 5 pages.
International Search Report for PCT/US2012/031538 dated Oct. 1, 2012, 5 pages.
International Search Report and Written Opinion of the International Searching Authority for International Application No. PCT/US2013/056970, dated Jan. 8, 2014, 23 pages.
Invitation to Pay Additional Fees for International Application No. PCT/US2013/056910, dated Oct. 24, 2013, 10 pages.
Jeske, W. et al. (1996). "Pharmacological Profiling of Recombinant Tissue Factor Pathway Inhibitor", *Seminars in Thrombosis and Hemostasis*, 22(2): 213-219.
Jones, A. (1993). "Analysis of Polypeptides and Proteins." *Adv. Drug Delivery Rev.* (10)29-90.
Kalapathy et al. (1996). "Alkali-Modified soy proteins: effect of salts and disulfide bond cleavage on adhesion and viscosity", *JAOCS* 73(8): 1063-1066.
Kamei, S. et al. (1994). "Amino Acid Sequences and Inhibitory Activity of Rhesus Monkey Tissue Factor Pathway Inhibitor (TFPI): Comparison with Human TFPI", 1994, *J. Biochem.* 115: 708-714.
Kanai et al. (2008). "Reversible Self-Association of a concentrated monoclonal antibody solution mediated by Fab-Fab interaction that impacts solution viscosity", *J Pharm Sci.* 97(10): 4219-4227.
Katdare et al. "Excipient Development for Pharmaceutical Biotechnology and Drug Delivery Systems", from Excipients for Protein Drugs, Informa Healthcare USA, Inc. (2006) (Gokam ed.), pp. 307-331.
Kim et al. (1997). "Diffusivity, viscosity, and cluster formation in protein solutions", *Biotechnol. Bioprocess Eng.* 2(1):64-67.
Kinekawa, et al. (1998). "Effects of Salts on the Properties of Sols and Gels Prepared from Whey Protein Isolate and Process Whey Protein," *Journal of Dairy Science* 81(6): 1532-1544.
Kochwa et al. (1966). "Aggregation of IgG Globulin in Vivo II. Physicochemical Properties of the Isolated Protein*", *Biochem.* 5(1):277-285.
Kohler et al. (Aug. 7, 1975). "Continuous Cultures of Fused Cells Secreting Antibody of Predefined Specificity", *Letters to Nature* 256:495-497.
Letter from D. Young & Co LLP to European Patent Office re Request to change the date of Oral Proceedings regarding the Opposition of European Patent No. EP2379600, dated May 6, 2016, 1 page.

(56) References Cited

OTHER PUBLICATIONS

Letter from Christopher Sykes, Director of Reagent Sales for Fitzgerald Industries to Brendan re 10R-T112A TFPI antibody inquiry, Citation in opposition procedure regarding European Patent No. EP2379600, submitted Aug. 30, 2016, D66, 1 page.
Letter from Hoffmann Eitle to European Patent Office re in response to the Summons dated Apr. 26, 2016 to attend oral proceedings regarding the Opposition of European Patent No. EP2379600, dated Aug. 30, 2016, 20 pages.
Letter from Pfizer to European Patent Department re oral proceedings attendance and additional remarks regarding the Opposition of European Patent No. EP2379600, dated Sep. 6, 2016, 3 pages.
Letter from D. Young & Co LLP to European Patent Office re updated consolidated Concordance table of citations/exhibits regarding the Opposition of European Patent No. EP2379600, dated Oct. 5, 2016, 2 pages.
Letter from Hoffmann Eitle to European Patent Office re response to patentee's Sep. 5, 2016 submission of new Declaration and references regarding the Opposition of European Patent No. EP2379600, dated Nov. 7, 2016, 6 pages.
Letter from D. Young & Co LLP to European Patent Office re reply to Opponent 1's submission of Aug. 30, 2016 and Nov. 7, 2016 and Opponent 2's submissions of Sep. 6, 2016 regarding the Opposition of European Patent No. EP2379600, dated Nov. 17, 2016, 8 pages.
Letter from Pfizer to European Patent Department re reply to Patentee's letter of Nov. 18, 2016 regarding the Opposition of European Patent No. EP2379600, dated Nov. 21, 2016, 1 page.
Letter from D. Young & Co LLP to European Patent Office re Auxiliary Claim Request regarding the Opposition of European Patent No. EP2379600, dated Dec. 20, 2016, 4 pages.
Letter from Hoffmann Eitle to European Patent Office re further response to Summons to attend oral proceedings and preparing for oral proceedings regarding the Opposition of European Patent No. EP2379600, dated Apr. 21, 2017, 4 pages.
Letter from D. Young & Co LLP to European Patent Office re providing copies of documents for oral proceedings regarding the Opposition of European Patent No. EP2379600, dated May 11, 2017, 1 page.
Letter from D. Young & Co LLP to European Patent Office re Patentee's Reply Submission regarding the Opposition of European Patent No. EP2379600, dated Jun. 9, 2017, 6 pages.
Lindhout, T., et al. (1994). "Kinetics of the Inhibition of Human Factor Xa by Full-length and Truncated Recombinant Tissue Factor Pathway Inhibitor", *Biochm. J.* 297: 131-136.
Liu et al. (Sep. 2005). "Reversible Self-Association Increases the Viscosity of a Concentrated Monoclonal Antibody in Aqueo Solution", *Journal of Pharmaceutical Sciences* 94(9).
Liu, T. et al. (2006). "Improved Coagulation in Bleeding Disorders by Non-Anticoagulant Sulfated Polysaccharides (NASP)", *Thromb. Haemost.* 95: 68-76.
Luo et al. (2006). "High-Concentration UF/DR of a Monoclonal Antibody", *Bioprocess International*, 4(2): 44-48.
Lwaleed, B. et al. (2006). "Tissue factor pathway inhibitor: structure, biology and involvement in disease", J. Pathol, 208: 327-339.
Maastricht University website, last visited Aug. 22, 2016, https://www.maastrichtuniversity.nl/, Citation in opposition procedure regarding European Patent No. EP2379600, submitted Aug. 30, 2016, 7 pages.
MacCallum, R. et al. (1996). Antibody-antigen Interactions: Contact Analysis and Binding Site Topography, *J. Mol. Biol.* 262: 732-745.
Manning et al. (1989). "Stability of Protein Pharmaceuticals", *Pharm. Res.* 6(11):903-918.
Marks et al. (Dec. 5, 1991). "By-passing Immunization human Antibodies from V-gene Libraries Displayed on Phage" *Journal of Molecular Biology*, 222: 581-597.
Maroney, S.A. and Mast, A.E., New Insights into the Biology of Tissue Factor Pathway Inhibitor, 2015, J. Thrombosis and Haemostasis 13 (Suppl 1): S200-S207.
Martinuzzo, M. et al. (2005). "Antiphospholipid Antibodies and Antibodies to Tissue Factor Pathway Inhibitor in Women with Implantation Failures or Early and Late Pregnancy Losses", *J. Thromb. Haemost* 3: 2587-2589.
Mast, A.E. et al. (2000). "Tissue Factor Pathway Inhibitor Binds to Platelet Thrombospondin-I", *J. Biol. Chem.* 41: 31715-31721.
Matheus et al. (Sep. 2009). "Liquid high concentration IgG 1 antibody formulations by precipitation." *J Pharm Sci.* 98(9): 3043-3057.
Mattern, M. et al. (1999). "Formulation of Proteins in Vacuum-Dried Glasses. II. Process and Storage Stability in Sugar-Free Amino Acid Systems," *Pharmaceutical Development and Technology* 4(2): 199-208.
Maurissen, LFA "Characterization of Anticoagulant Functions of Protein S", publically defended on Feb. 18, 2009, published in print 2009, PhD thesis.
Maurissen, LFA et al., (2010). "Thrombin generation-based assays to measure the activity of the TFPI-protein S pathway in plasma from normal and protein S-deficient individuals," *Journal of Thrombosis and Haemostasis*, 8:750-758.
McCafferty et al. (Dec. 6, 1990). "Phage Antibodies: Filamentous Phage Displaying Antibody Variable Domains", *Letters to Nature* 348(6301): 552-554.
Menjivar et al. (1980). "Viscoelastic effects in concentrated protein dispersions", *Rheol. Acta* 19:212-219.
Metcalfe, P. et al (2006). World Health Organization Expert Committee on Biological Standardization, Geneva Oct. 23-27, 2006 (WHO/BS/06.2033), Opposition to European Patent No. EP2379600, D98, 16 pages.
Monkos (1997). "Concentration and temperature dependence of viscosity in lysozyme aqueous solutions", Biochimica et Biophysica Acta 1339:304-310.
Monkos et al. (1999). "A comparative study on viscosity of human, bovine and pig IgG immunoglobulins in aqueous solutions", *Int. J. Bio. Macromolecules* 26:155-159.
Monkos (2000). "Viscosity analysis of the temperature dependence of the solution conformation to ovalbumin", *Biophysical Chem.* 85:7-16.
Moore, J. et al. (1999). "Kinetics and Thermodynamics of Dimer Formation and Dissociation for a Recombinant Humanized Monoclonal Antibody to Vascular Endothelial Growth Factor"; *Biochemistry* 13960-13967.
Morrison et al. (1984). "Chimeric Human Antibody Molecules: Mouse Antigen-Binding Domains with Human Constant Region Domains", *Proceedings of the National Academy of Sciences of USA* 81: 6851-6855.
Myszka, D.G. (1999). "Improving Biosensor Analysis", *J. Mol. Recognit.* 12:279-284.
Ndonwi, M. et al. (2008). "Protein S Enhances the Tissue Factor Pathway Inhibitor Inhibition of Factor Xa but not its Inhibition of Factor VIIa-Tissue Factor", *Thrombosis Haemostasis* 6: 1044-1046.
Ndonwi, M. et al. (2010). "The Kunitz-3 Domain of TFPI-a. is Required for Protein S-Dependent Enhancement of Factor Xa Inhibition", *Blood* 116(8): 1344-1351.
Nordfang, O. et al. (1991). "Inhibition of Extrinsic Pathway Inhibitor Shortens the Coagulation Time of Normal Plasma and of Hemophilia Plasma", *Thrombosis and Haemostasis* 66(4): 464-467.
Non-Final Office Action dated Jul. 12, 2012, for U.S. Appl. No. 13/323,691.
Non-Final Office Action dated Jun. 18, 2013, for U.S. Appl. No. 13/057,728.
Non-Final Office Action dated Sep. 11, 2013, for U.S. Appl. No. 13/582,401.
Non-Final Office Action dated Aug. 7, 2015, for U.S. Appl. No. 13/057,728.
Non-Final Office Action dated Sep. 30, 2016, for U.S. Appl. No. 13/057,728.
Notice of Opposition and Letter for European Patent No. EP2379600, Opponent Bayer Intellectual Property GMBH, dated Oct. 22, 2014, 18 pages.
Notice of Opposition and Letter for European Patent No. EP2379600, Opponent Pfizer Inc., dated Oct. 22, 2014, 21 pages.

(56) References Cited

OTHER PUBLICATIONS

Notice of Opposition Letter for European Patent No. EP2379600, Opponents Bayer Intellectual Property GMBH and Bayer Healthcare LLC, dated Oct. 22, 2014, 6 pages.
Notice of Opposition Letter for European Patent No. EP2379600, Opponent Pfizer Inc., dated Oct. 22, 2014, 8 pages.
Novotny, J. et al. (1986). "Antigenic Determinants in Proteins Coincide with Surface Regions Accessible to Large Probes (Antibody Domains)", *Proc. Natl. Acad. Sci. USA*, 83:226-230.
Office Action, Chinese Application No. 200980134625.4 dated Apr. 23, 2013.
Office Action, Mexican Application No. MX/a2011/001351 dated May 6, 2014.
Østergaard, P.G. et al. (1997). An Enzyme Linked Immunosorption Assay for Tissue Factor Pathway Inhibitor, *Thrombosis Research* 87(5): 447-459.
Patapoff et al; (2009). "Polysorbate 20 Prevents the Precipitation of a Monoclonal Antibody During Shear," *Pharmaceutical Development and Technology* 14(6):659-664.
Pearlman et al. (1991). "Analysis of Protein Drugs," Chapter 6 in Peptide and Protein Drug Delivery, Vincent H. L. Lee ed., Marcel Dekker, Inc., pp. 247-301.
Petersen, L.C. et al. (1992). "Effect of Leukocyte Proteinases on Tissue Factor Pathway Inhibitor", *Thrombosis and Haemostasis* 67(5): 537-541.
Petersen, JGL et al. (1993). "Characterization of Human Tissue Factor Pathway Inhibitor Variants Expressed in *Saccharomyces cerevisiae", J. Biol. Chem.* 268(18): 13344-13351.
Petersen, L.C. et al. (1996). "Inhibitory Properties of Separate Recombinant Kunitz-type-protease-inhibitor Domains from Tissue-factor-pathway Inhibitor," *Eur. J. Biochem.* 235: 310-316.
Petersen, H.H., "Experimental—Binding of mAbTFPI12021/NN mAb2021 and Bayer mAb2A8 to the isolated K2 Domain of TFPI", date Jul. 20, 2015, Declaration, Novo Nordisk A/S, European Patent No. EP2379600 Opposition.
Petersen, H.H., "Experimental—Determination that Specific Monoclonal Antibodies are Capable of Binding to Individual Isolated Kunitz Domains of TFPI", dated Jul. 20, 2015, Declaration, Novo Nordisk A/S, European Patent No. EP2379600 Opposition.
Petersen, H.H., "Experimental—Kinetic Parameters for the Interaction between Full-Length TFPI with mAbTFPI2021/NN mAb2021, Bayer mAb2A8 and R&D Systems mAb2974", 2015, Declaration, Novo Nordisk A/S, dated Jul. 20, 2015, EP2379600 Opposition.
Pfizer Inc. Generated Technical Report on 2A8/TFPI Binding Location, in EP2379600 Opposition filed by Pfizer, Oct. 22, 2014.
Pfizer Inc. Generated Technical Report on 2A8/TFPI KD, in European Patent No. EP2379600 Opposition filed by Pfizer, Oct. 22, 2014.
Pikal et al. (1991). "The Effects of Formulation Variables on the Stability of Freeze-Dried Human Growth Hormone," *Pharmaceutical Research* 8:427-436.
Portolano et al. (1983). *J. Immunol.*, 150:880-887.
Prasad, S. et al. (2008). "Efficacy and Safety of a New-class Hemostatic Drug Candidate, AV513, in Dogs with Hemophilia A", *Blood* 111(2): 672-679.
Queen et al. (Dec. 1989). "A Humanized Antibody that Binds to the Interleukin 2 Receptor", *Proc. Natl. Acd. Sci. USA* 86(24): 10029-33.
Quotation CBLD11201402 Report by Creative Biolabs to Sunil Bajad, Bayer Healthcare Inc., dated Feb. 3, 2015, Opposition to European Patent No. EP2379600, D87a, 55 pages.
Quotation CBLD11201402 Report by Creative Biolabs to Sunil Bajad, Bayer Healthcare Inc., dated Feb. 5, 2016, Opposition to European Patent No. EP2379600, D87b, 53 pages.
R&D Systems, R&D Systems New Products—Jun. 2007, http://www.rndsystems.co.uk, Human TFPI Antibody, Monoclonal Mouse IgG2a Clone # 374720, Catalog No. MAB2974.
R&D Systems, R&D Systems New Products—Jun. 2007, http://www.rndsystems.co.uk.
Ragni, M. et al. (2000). "Endogenous Tissue Factor Pathway Inhibitor Modulates Thrombus Formation in an In Vivo Model of Rabbit Carotid Artery Stenosis and Endothelial Injury", *Circulation*, 102:113-117.
Reninger, A.J. et al. (2006). "Mechanism of platelet adhesion to van Willebrandfactor and microparticle formation under high shear stress", *BloodJournal.Hematologylibrary.org* 7(9).
Reply to Notice(s) of Opposition against European Patent No. EP2379600, dated Aug. 11, 2015, 50 pages.
Rezaie, A. et al. (2006). "Determinants of Specificity of Factor Xa Interaction with its Physiological Inhibitors", *Mini-Reviews in Medicinal Chemistry*, 859-865.
Richards, F.M. (1985). "Calculation of Molecular Volumes and Areas for Structures of Known Geometry", *Methods in Enzymology*, 115: 440-464.
Riechmann et al. (Mar. 24, 1988). "Reshaping Human Antibodies for Therapy", *Nature* 332(6162): 323-27.
Riesbeck, K. et al. (1997). "Human Tissue Factor Pathway Inhibitor Fused to CD4 Binds both FXa and TF/FVIIa at the Cell Surface", *Thromb. Haemost.* 78:1488-1494.
Rocchia, W. et al. (2001). "Extending the Applicability of the Nonlinear Poisson-Boltzmann Equation: Multiple Dielectric Constants and Multivalent Ions", *J. Phys. Chem. B* 105:6507-6514.
Rudikoff et al. (Mar. 1982). "Single Amino Acid Substitution Altering Antigen-Binding Specificity", 79(6): 1979-1983.
Salinas et al. (2010). "Understanding and Modulation Opalescence and Viscosity in a Monoclonal Antibody Formulation", *Journal of Pharmaceutical Sciences*, 99(1): 82-93.
Saluja et al. (Dec. 2007). "Ultrasonic rheology of a monoclonal antibody (IgG2) solution: implications for physical stability of proteins in high concentration formulations", *J Pharm Sci.* 96(12): 3181-95.
Saluja et al. (2008). "Nature and consequences of protein-protein interactions in high protein concentration solutions", *Int. J. Pharm.* 358: 1-15.
Sandset, P.M. et al. (Feb. 1991). "Depletion of extrinsic pathway inhibitor (EPI) sensitizes rabbits to disseminated intravascular coagulation induced with tissue factor: Evidence supporting a physiologic role for EPI as a natural anticoagulant", *Proc. Natl. Acad. Sci. USA*, 88: 708-712.
Sanquin Blood Supply Homepage, undated, located at https://www.sanquin.nl/en/about/about-sanquin/), Opposition to European Patent No. EP2379600, D95, 1 page.
Sanquin Blood Supply (2012). "Off-List Products: Product in Development," located at https://www.sanquin.nl/en/productsservices/reagents/product-categories/off-list-products/, Opposition to European Patent No. EP2379600, D96, 2 pages.
Schildbach et al. (Feb. 9, 1994). "Contribution of a Single Heavy Chain Residue to Specificity of an Anti-Digoxin Monoclonal Antibody", 3: 737-749.
Sevinsky, J.R. et al. (Apr. 1996). "Ligand-Induced Protease Receptor Translocation into Caveloae: A Mechanism for Regulating Cell Surface Proteolysis of the Tissue Factor Dependent Coagulation Pathway", *The Journal of Cell Biology*, 133(2): 293-304.
Shetty, S. et al. (2015). "Novel therapeutic approaches for haemophilia", *Haemophilia*, 21, 152-161.
Shire, S.J. et al. (Jun. 1, 2004). "Challenges in the development of high protein concentration formulations", *Journal of Pharmaceutical Sciences, American Pharmaceutical Association*, Washington, US, 93(6): 1390-1402, XP009108986, ISSN: 0022-3549, DOI: 10.1002/jps.20079 p. 1396, right hand column.
Siegel, F.P. "Tonicity, Osmoticity, Osmolality and Osmolarity" Ch. 79, *Remington's Pharmaceutical Sciences*, 18th Ed., Gennaro ed., Mack Publishing Co., 1990, 1481-1498.
Submission in European Opposition Proceeding of European Patent No. EP2379600.
Szencizi, A. et al. (Mar. 2006). "The effect of solvent environment on the conformation and stability of human polyclonal IgG in solution"; *Biologicals*, 34(1):5-14.
Tanford, C. et al. (1956). "The Viscosity of Aqueous Solutions of Bovine Serum Albumin Between pH 4.3 and l0.51", *J. Phys. Chem.* 60:225-231.

(56) References Cited

OTHER PUBLICATIONS

Tang, H. et al. (2007). "Sepsis-Induced Coagulation in the Baboon Lung Is Associated with Decreased Tissue Factor Pathway Inhibitor", *Am Journal of Pathology*, 171(3).
Technical Report: Determination of 2A8 Fab/TFPI complex structure for epitope analysis, Opposition to European Patent No. EP2379600, prepared by Pfizer Inc., D16, 3 pages.
Technical Report: Dissociation constant ($K_d$) determination for anti-TFPI antibodies by Surface Plasmon Resonance, Opposition to European Patent No. EP2379600, prepared by Pfizer Inc., D17, 2 pages.
Tian, F. et al. (2003). "Spectroscopic Evaluation of the Stabilization of Humanized Monoclonal Antibodies in Amino Acid Formulations," *International Journal of Pharmaceutics* 335:20-31.
Tiemann, C. et al. (1997). "Detection of the Three Kunitz-Type Single Domains of Membrane-Bound Tissue Factor Pathway Inhibitor (TFPI) by Flow Cytometry", *Eur J Chin Biochem*, 37(11): 855-860.
Uni-ProtKB I Swiss-Prot entry PI0646, Tissue Factor Pathway Inhibitor, online http://www.uniprot.org/uniprot/PI0646.
Van Der Poll, T. (2008). "Tissue Factor as an Initiator of Coagulation and Inflammation in the Lung", Critical Care 12 (Suppl. 6): S3.
Van 'T Veer, C. et al. (1994). "Activated factor X and thrombin formation triggered by tissue factor on endothelial cell matrix in a flow model: effect of the tissue factor pathway inhibitor", 84: 1132-1142.
Vajdos, F. et al. (2002). "Comprehensive Functional Maps of the Antigen-binding Site of an Anti-ErbB2 Antibody Obtained with Shotgun Scanning Mutagenesis," *J. Mol. Biol*, 320: 415-428.
Violand, B.N. et al. (1995). "Determination of the Disulfide Bond Pairings in Human Tissue Factor Pathway Inhibitor Purified from *Escherichia coli*", 14(5): 341-347.
Wang (1999). "Instability, stabilization, and formulation of liquid protein pharmaceuticals", Int. J. Pharm. 185: 129-188.
Wang et al. (Jan. 2007). "Antibody Structure, Instability, and Formulation," *Journal of Pharmaceutical Sciences* 96(1):1-26.
Warn-Cramer, B.J. et al. (1993). "Studies of Factor Xa/Phospholipid-Induced Intravascular Coagulation in Rabbits—Effects of Immunodepletion of Tissue Factor Pathway Inhibitor", *Arteriosclet Throm.*, 13:1551-1557.
Weir, D. et al. "Immunology: Chapter 10—Interaction of antibody with antigen and applications in laboratory investigations", pp. 325-326.
Welsch, D.J., et al. (1991). "Effect of Lipoprotein-Associated Coagulation Inhibitor (LACI) on Thromboplastin-Induced Coagulation of Normal and Hemophiliac Plasmas", *Thrombosis Research*, 64: 213-222.
Willyard, C., (2014). "Balancing Act—A Promising Therapy Curtails Clotting Inhibitors rather than Replacing Proteins that Promote Blood Clotting", *Nature* 515: Sl68-Sl69.
Winkler, K. et al. (2000). "Changing the Antigen binding specificity by Single Point Mutations of an Anti-p24 (HIV-I) Antibody", *Journ. of Immunology*, 165; 4505-4514.
Wong, W-Y et al. "Treatment of Hemophilia A and B with BAX 499, an Aptamer Based Specific Inhibitor of TFPI-Summary Data of a Clinical Phase 1 Trial," Baxter, Jul. 11, 2012.
Written Opinion for PCT/EP2009/067598 dated Jun. 22, 2011.
Wu, H. et al., (1999). "Hominization of a Murine Monoclonal Antibody by Simultaneous Optimization of Framework and CDR Residues", *J. Mol. Biol.*, 294, 151-162.
Xiang et al. (May 1, 2000). "Study of B72.3 Combining Sites by Molecular Modeling and Site-Directed Mutagenesis", 13(5): 113-344.
Yadav et al. (Mar. 2010). "Specific interactions in high concentration antibody solutions resulting in high viscosity.", J Pharm Sci., 99(3):1152-1168.
Yadav et al. (Dec. 2010). "Factors affecting the viscosity in high concentration solutions of different monoclonal antibodies", *J Pharm Sci.*, 99(12): 4812-4829.
Yadav et al. (Aug. 2011). "Viscosity analysis of high concentration bovine serum albumin aqueous solutions", *Pharm Res.*, 228(8): 1973-83.
Yadav et al. (Mar. 2012). "Viscosity behavior of high-concentration monoclonal antibody solutions: correlation with interaction parameter and electro viscous effects"; *J Pharm Sci.*, 101(3): 998-1011.
Yang, Y. et al. (1997). "Preparation and Identification of a Monoclonal Antibody Against Tissue Factor Pathway Inhibitor", *Chin. J. Hematol.* 18(3):118-122.
Yousef, M.A. et al. (1998). "Free-Solvent Model of Osmotic Pressure Revisited: Application to Concentrated IgG Solution under Physiological Conditions." *Journal of Colloid and Interface Science*, 97: 108-118.
Zhang, E. et al. (1999). "Structure of Extracellular Tissue Factor Complexed with Factor VIIa Inhibited with a BPTI Mutant", *J. Mol. Biol.* 285: 1089-2104.
Zhang, Z. et al. (2014). "Structure-activity relationship of the pro- and anticoagulant effects of Fucus vesiculosus fucoidan," *Thrombosis and Haemostasis* 111(3): 429-437.
Zillmann, A. et al. (2001). "Platelet-Associated Tissue Factor Contributes to the Collagen-Triggered Activation of Blood Coagulation", *Biochem. Biophys. Res. Commun.* 281:603-609.
"European Search Report for Application No. EP17172199.6 dated Nov. 15, 2017".
Ragni et al., "Endogenous Tissue Factor Pathway Inhibitor Modulates Thrombus Formation in an In Vivo Model of Rabbit Cartoid Artery Stenosis and Endothelial Injury," Circulation, 2000, vol. 102, pp. 118-117.
Warn-Cramer B.J. et al. (1992). "Purification of Tissue Factor Pathway Inhibitor (TFPI) from Rabbit Plasma and Characterization of its Differences from TFPI isolated from Human Plasma", Thrombosis Research, 67: 367-383.
Yang; et al., "CDR Walking Mutagenesis for the Affinity Maturation of a Potent Human Anti-HIV-1 Antibody into the Picomolar Range", Journal of Molecular Biology, vol. 254, 392-403.
Janeway et al., Immunobiology, 3rd edition, 1997, Garland Press, pp. 3:1-3:11.*
Rudikoff et al., Proc Natl Acad Sci USA, 1982, 79:1979-1983.*
Portolano et al., J. Immunol., 1993, 150:880-887.*
Fundamental Immunology, William E. Paul, M.D. ed., 3d ed. 1993, p. 242.*
PCT/US2009/052702, PCT Written Opinion of the International Searching Authority, Jun. 22, 2011.
Petersen JGL, G Meyn, JS Rasmussen, J Petersen, SE Bjørn, I Jonassen, L Christiansen and O Nordfang, *Characterization of Human Tissue Factor Pathway Inhibitor Variants Expressed in Saccharomyces cerevisiae*, 1993, J. Biol. Chem. 268 (18): 13344-13351.
Petersen, LC, SE Bjørn, OH Olsen, ZO Nordfang, F Norris and K Norris, *Inhibitory Properties of Separate Recombinant Kunitz-type-protease-inhibitor Domains from Tissue-factor-pathway Inhibitor*, 1996, Eur. J. Biochem. 235: 310-316.
Tang H, L. Ivanciu, N. Popescu, G Peer, E Hack, C Lupu, Fb Taylor Jr, and F. Lupu. *Sepsis-Induced Coagulation in the Baboon Lung Is Associated with Decreased Tissue Factor Pathway Inhibitor*, 2007, Am Journ. of Pathology vol. 171 #3.
rndsystems.tfpi "Human TFPI", Catalog No. DY2974.
Sevinsky J. R., L. Vijay Mohan Rao, and W. Ruf, *Ligand-Induced Protease Receptor Translocaiton into Caveloae: A Mechanism for Regulating Cell Surface Proteolysis of the Tissue Factor -Dependent Coagulation Pathway*, The Journal of Cell Biology, Apr. 1996, vol. 133, No. 2, pp. 293-304.
MacCallum, R., A.C.R. Martin, J. M. Thornton, *Antibody-antigen Interactions: Contact Analysis and Binding Site Topography*, J. Mol. Biol. (1996) 262, 732-745.
GE Healthcare, Biacore Training Courses, *Kinetic and Affinity Analysis, Level 2*, extract, 1998.
Petersen LC, BJørn SE and O Nordfang, *Effect of Leukocyte Proteinases on Tissue Factor Pathway Inhibitor*, 1992, Thrombosis and Haemostasis 67(5): 537-541.
Protein Data Bank file 1ADZ, 1998.
Protein Data Bank file 1TFX, 1998.

(56) References Cited

OTHER PUBLICATIONS

Submission in European Opposition Proceeding of European Patent No. EP2379600, Aug. 11, 2015.

* cited by examiner

| Number | Clone | Sample |
|---|---|---|
| 3 | HC_S31V | 2A8-3 |
| 9 | HC_K99L | 2A8-9 |
| 17 | LC_D91W | 2A8-17 |
| 20 | Wild type | 2A8 |

| Number | Clone | Sample |
|---|---|---|
| 9 | HC_K99L | 2A8-9 |
| 10 | HC_K99V | |
| 17 | LC_D91W | 2A8-17 |
| 20 | Wild type | 2A8 |

| Sample | Clone |
|---|---|
| 2A8-9 | HC_K99L |
| 4B7-D58R | HC_D62R |
| 4B7 | Wild type 4B7 |

OPTIMIZED MONOCLONAL ANTIBODIES AGAINST TISSUE FACTOR PATHWAY INHIBITOR (TFPI)

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is *is an application for reissue of U.S. Pat. No. 9,309,324, which issued from U.S. application Ser. No. 13/582,401, filed Aug. 31, 2012, which is* a national phase of International Application No. PCT/US2011/026766, filed Mar. 1, 2011, which [is] claims the benefit of U.S. Provisional Application No. 61/309,290 filed Mar. 1, 2010.

SEQUENCE LISTING SUBMISSION

The Sequence Listing associated with this application is filed in electronic format via EFS-Web and hereby incorporated by reference into the specification in its entirety.

FIELD OF THE EMBODIMENTS

Provided are isolated monoclonal antibodies and fragments thereof that bind human tissue factor pathway inhibitor (TFPI).

BACKGROUND

Blood coagulation is a process by which blood forms stable clots to stop bleeding. The process involves a number of proenzymes and procofactors (or "coagulation factors") that are circulating in the blood. Those proenzymes and procofactors interact through several pathways through which they are converted, either sequentially or simultaneously, to the activated form. Ultimately, the process results in the activation of prothrombin to thrombin by activated Factor X (FXa) in the presence of Factor Va, ionic calcium, and platelets. The activated thrombin in turn induces platelet aggregation and converts fibrinogen into fibrin, which is then cross linked by activated Factor XIII (FXIIIa) to form a clot.

The process leading to the activation of Factor X can be carried out by two distinct pathways: the contact activation pathway (formerly known as the intrinsic pathway) and the tissue factor pathway (formerly known as the extrinsic pathway). It was previously thought that the coagulation cascade consisted of two pathways of equal importance joined to a common pathway. It is now known that the primary pathway for the initiation of blood coagulation is the tissue factor pathway.

Factor X can be activated by tissue factor (TF) in combination with activated Factor VII (FVIIa). The complex of Factor VIIa and its essential cofactor, TF, is a potent initiator of the clotting cascade.

The tissue factor pathway of coagulation is negatively controlled by tissue factor pathway inhibitor ("TFPI"). TFPI is a natural, FXa-dependent feedback inhibitor of the FVIIa/TF complex. It is a member of the multivalent Kunitz-type serine protease inhibitors. Physiologically, TFPI binds to activated Factor X (FXa) to form a heterodimeric complex, which subsequently interacts with the FVIIa/TF complex to inhibit its activity, thus shutting down the tissue factor pathway of coagulation. In principle, blocking TFPI activity can restore FXa and FVIIa/TF activity, thus prolonging the duration of action of the tissue factor pathway and amplifying the generation of FXa, which is the common defect in hemophilia A and B.

Indeed, some preliminary experimental evidence has indicated that blocking the TFPI activity by antibodies against TFPI normalizes the prolonged coagulation time or shortens the bleeding time. For instance, Nordfang et al. showed that the prolonged dilute prothrombin time of hemophilia plasma was normalized after treating the plasma with antibodies to TFPI (Thromb. Haemost., 1991, 66(4): 464-467). Similarly, Erhardtsen et al. showed that the bleeding time in hemophilia A rabbit model was significantly shortened by anti-TFPI antibodies (Blood Coagulation and Fibrinolysis, 1995, 6: 388-394). These studies suggest that inhibition of TFPI by anti-TFPI antibodies may be useful for the treatment of hemophilia A or B. Only polyclonal anti-TFPI antibody was used in these studies.

Using hybridoma techniques, monoclonal antibodies against recombinant human TFPI (rhTFPI) were prepared and identified. See Yang et al., Chin. Med. J., 1998, 111(8): 718-721. The effect of the monoclonal antibody on dilute prothrombin time (PT) and activated partial thromboplastin time (APTT) was tested. Experiments showed that anti-TFPI monoclonal antibody shortened dilute thromboplastin coagulation time of Factor IX deficient plasma. It is suggested that the tissue factor pathway plays an important role not only in physiological coagulation but also in hemorrhage of hemophilia (Yang et al., Hunan Yi Ke Da Xue Xue Bao, 1997, 22(4): 297-300).

Accordingly, antibodies specific for TFPI are needed for treating hematological diseases and cancer.

Generally, therapeutic antibodies for human diseases have been generated using genetic engineering to create murine, chimeric, humanized or fully human antibodies. Murine monoclonal antibodies were shown to have limited use as therapeutic agents because of a short serum half-life, an inability to trigger human effector functions, and the production of human antimouse-antibodies (Brekke and Sandlie, "Therapeutic Antibodies for Human Diseases at the Dawn of the Twenty-first Century," Nature 2, 53, 52-62, January 2003). Chimeric antibodies have been shown to give rise to human anti-chimeric antibody responses. Illumanized antibodies further minimize the mouse component of antibodies. However, a fully human antibody avoids the immunogenicity associated with murine elements completely. Thus, there is a need to develop fully human antibodies to avoid the immunogenicity associated with other forms of genetically engineered monoclonal antibodies. In particular, chronic prophylactic treatment such as would be required for hemophilia treatment with an anti-TFPI monoclonal antibody has a high risk of development of an immune response to the therapy if an antibody with a murine component or murine origin is used due to the frequent dosing required and the long duration of therapy. For example, antibody therapy for hemophilia A may require weekly dosing for the lifetime of a patient. This would be a continual challenge to the immune system. Thus, the need exists for a fully human antibody for antibody therapy for hemophilia and related genetic and acquired deficiencies or defects in coagulation.

Therapeutic antibodies have been made through hybridoma technology described by Koehler and Milstein in "Continuous Cultures of Fused Cells Secreting Antibody of Predefined Specificity," Nature 256, 495-497 (1975). Fully human antibodies may also be made recombinantly in prokaryotes and eukaryotes. Recombinant production of an antibody in a host cell rather than hybridoma production is preferred for a therapeutic antibody. Recombinant production has the advantages of greater product consistency, likely higher production level, and a controlled manufacture that minimizes or eliminates the presence of animal-derived proteins, For these reasons, it is desirable to have a recombinantly produced monoclonal anti-TFPI antibody.

In addition, because TFPI binds to activated Factor X (FXa) with high affinity, an effective anti-TFPI antibody should have a comparable affinity. Thus, it is desirable to have an anti-TFPI antibody which has binding affinity which can compete with TFPI/FXa binding.

SUMMARY

Monoclonal antibodies to human tissue factor pathway inhibitor (TFPI) are provided. Further provided are the isolated nucleic acid molecules encoding the same. Pharmaceutical compositions comprising the anti-TFPI monoclonal antibodies and methods of treatment of genetic and acquired deficiencies or defects in coagulation such as hemophilia A and B are also provided. Also provided are methods for shortening the bleeding time by administering an anti-TFPI monoclonal antibody to a patient in need thereof. Methods for producing a monoclonal antibody that binds human TFPI according to the present invention are also provided.

In some embodiments, the monoclonal antibodies to TFPI provided have been optimized, for example to have increased affinity or increased functional activity.

DETAILED DESCRIPTION

Definitions

Figure 1:
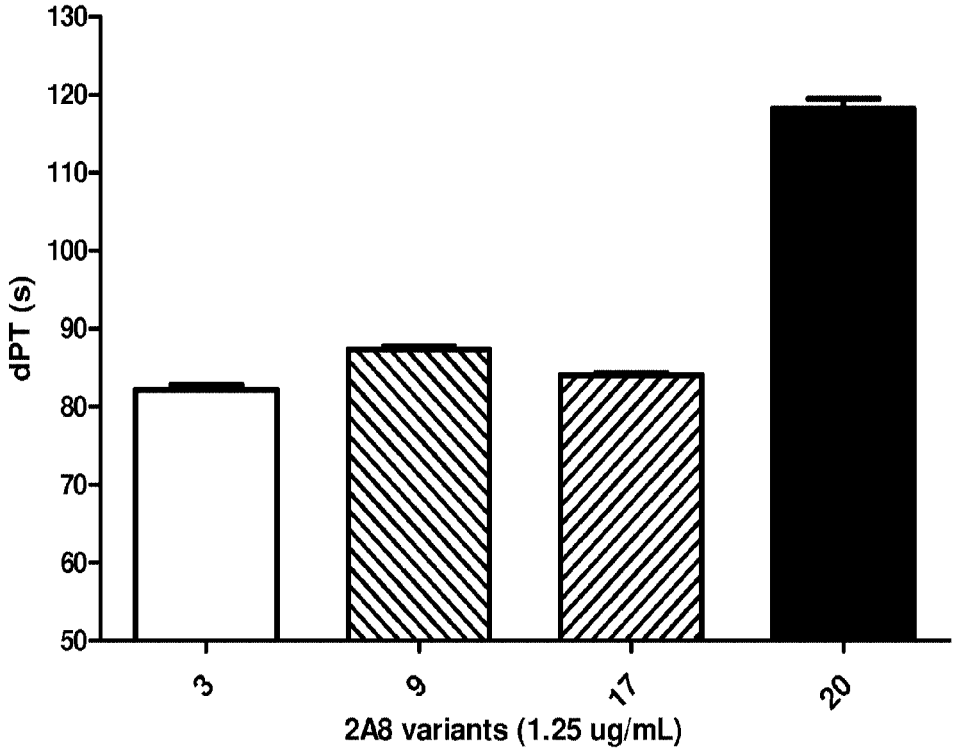
FIG. 1 depicts a bar graph illustrating selected 2A8 variants with single amino acid substitutions which showed more potency in shortening clotting time in human hemophilia A plasma using a dPT assay.

The term "tissue factor pathway inhibitor" or "TFPI" as used herein refers to any variant, isoform and species homolog of human TFPI that is naturally expressed by cells. In a preferred embodiment of the invention, the binding of an antibody of the invention to TFPI reduces the blood clotting time.

As used herein, an "antibody" refers to a whole antibody and any antigen binding fragment (i.e., "antigen-binding portion") or single chain thereof. The term includes a full-length immunoglobulin molecule (e.g., an IgG antibody) that is naturally occurring or formed by normal immunoglobulin gene fragment recombinatorial processes, or an immunologically active portion of an immunoglobulin molecule, such as an antibody fragment, that retains the specific binding activity. Regardless of structure, an antibody fragment binds with the same antigen that is recognized by the full-length antibody. For example, an anti-TFPI monoclonal antibody fragment binds to an epitope of TFPI. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR); (vii) minibodies, diaboidies, triabodies, tetrabodies, and kappa bodies (see, e.g. Ill et al., Protein Eng 1997; 10:949-57); (viii) camel IgG; and (ix) IgNAR. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are analyzed for utility in the same manner as are intact antibodies.

Furthermore, it is contemplated that an antigen binding fragment may be encompassed in an antibody mimetic. The term "antibody mimetic" or "mimetic" as used herein is meant a protein that exhibits binding similar to an antibody but is a smaller alternative antibody or a non-antibody protein. Such antibody mimetic may be comprised in a scaffold. The term "scaffold" refers to a polypeptide platform for the engineering of new products with tailored functions and characteristics.

As used herein, the terms "inhibits binding" and "blocks binding" (e.g., referring to inhibition/blocking of binding of TFPI ligand to TFPI) are used interchangeably and encompass both partial and complete inhibition or blocking. Inhibition and blocking are also intended to include any measurable decrease in the binding affinity of TFPI to a physiological substrate when in contact with all anti-TFPI antibody as compared to TFPI not in contact with an anti-TFPI antibody, e.g., the blocking of the interaction of TFPI with factor Xa or blocking the interaction of a TFPI-factor Xa complex with tissue factor, factor VIIa or the complex of tissue factor/factor VIIa by at least about 10%, 20%, 30%, 40%, 50%, 60%, 70%, 80%, 90%, 95%, 96%, 97%, 98%, 99%, or 100%.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo).

An "isolated antibody," as used herein, is intended to refer to an antibody which is substantially free of other antibodies having different antigenic specificities (e.g., an isolated antibody that binds to TFPI is substantially free of antibodies that bind antigens other than TFPI). An isolated antibody that binds to an epitope, isoform or variant of human TFPI may, however, have cross-reactivity to other related antigens, e.g., from other species (e.g., TFPI species homologs). Moreover, an isolated antibody may be substantially free of other cellular material and/or chemicals.

As used herein, "specific binding" refers to antibody binding to a predetermined antigen. Typically, the antibody binds with an affinity of at least about $10^5$ $M^{-1}$ and binds to the predetermined antigen with an affinity that is higher, for example at least two-fold greater, than its affinity for binding to an irrelevant antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, the term "high affinity" for an IgG antibody refers to a binding affinity of at least about $10^7M^{-1}$, in some embodiments at least about $10^8M^{-1}$, in some embodiments at least about $10^9M^{-1}$, $10^{10}M^{-1}$, $10^1M^{-1}$ or greater, e.g., up to $10^{13}M^{-1}$ or greater. However, "high affinity" binding can vary for other antibody isotypes. For example, "high affinity" binding for an IgM isotype refers to a binding affinity of at least about $1.0\times10^7M^{-1}$. As used herein, "isotype" refers to the antibody class (e.g., IgM or IgG1) that is encoded by heavy chain constant region genes.

"Complementarily-determining region" or "CDR" refers to one of three hypervariable regions within the variable region of the heavy chain or the variable region of the light chain of an antibody molecule that form the N-terminal antigen-binding surface that is complementary to the three-dimensional structure of the bound antigen. Proceeding from the N-terminus of a heavy or light chain, these complementarity-determining regions are denoted as "CDR1,""CDR2," and "CDR3," respectively. CDRs are involved in antigen-antibody binding, and the CDR3 comprises a unique region specific for antigen-antibody binding. An antigen-binding site, therefore, may include six CDRs, comprising the CDR regions from each of a heavy and a light chain V region.

As used herein, "conservative substitutions" refers to modifications of a polypeptide that involve the substitution of one or more amino acids for amino acids having similar biochemical properties that do not result in loss of a biological or biochemical function of the polypeptide. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). It is envisioned that the antibodies of the present invention may have conservative amino acid substitutions and still retain activity.

For nucleic acids and polypeptides, the term "substantial homology" indicates that two nucleic acids or two polypeptides, or designated sequences thereof, when optimally aligned and compared, are identical, with appropriate nucleotide or amino acid insertions or deletions, in at least about 80% of the nucleotides or amino acids, usually at least about 85%, preferably about 90%, 91%, 92%, 93%, 94%, or 95%, more preferably at least about 96%, 97%, 98%, 99%, 99.1%, 99.2%, 99.3%, 99.4%, or 99.5% of the nucleotides or amino acids. Alternatively, substantial homology for nucleic acids exists when the segments will hybridize under selective hybridization conditions to the complement of the strand. The invention includes nucleic acid sequences and polypeptide sequences having substantial homology to the specific nucleic acid sequences and amino acid sequences recited herein.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, such as without limitation the AlignX™ module of VectorNTI™ (Invitrogen Corp., Carlsbad, Calif.). For AlignX™, the default parameters of multiple alignment are: gap opening penalty: 10; gap extension penalty: 0.05; gap separation penalty range: 8; % identity for alignment delay: 40. Further details found at: Invitrogen's website for LINNEA Communities, Vector TFI Community, AlignX module for Vector NTI.

Another method for determining the best overall match between a query sequence (a sequence of the present invention) and a subject sequence, also referred to as a global sequence alignment, can be determined using the CLUSTALW computer program (Thompson et al., Nucleic Acids Research, 1994, 2(22): 4673-4680), which is based on the algorithm of Higgins et al., (Computer Applications in the Biosciences (CABIOS), 1992, 8(2): 189-191). In a sequence alignment the query and subject sequences are both DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty=10, Gap Extension Penalty-0.1. For multiple alignments, the following CLUSTALW parameters are preferred: Gap Opening Penalty=10, Gap Extension Parameter=0.05; Gap Separation Penalty Range=8; % Identity for Alignment Delay=40.

The nucleic acids may be present in whole cells, in a cell lysate, or in a partially purified or substantially pure form. A nucleic acid is "isolated" or "rendered substantially pure" when purified away from other cellular components with which it is normally associated in the natural environment. To isolate a nucleic acid, standard techniques such as the following may be used: alkaline/SDS treatment, CsCl handing, column chromatography, agarose gel electrophoresis and others well known in the art.

Monoclonal Antibodies Optimized for High Affinity and Functional Activity

Several anti-TFPI antibodies were identified in a previous study and described in PCT Application No. PCT/US2009/052702 filed 4 Aug. 2009, hereby incorporated by reference for all purposes. These anti-TFPI antibodies may be further optimized, for example by improving their affinity and blocking activity to TFPI. Such optimization can be performed for example by utilizing site saturation mutagenesis of the complementarily determining regions (CDRs) or residues in close proximity to the CDRs, i.e. about 3 or 4 residues adjacent to the CDRs, of the antibodies.

Also provided are monoclonal antibodies having increased or high affinity to TFPI. In some embodiments, the anti-TFPI antibodies have a binding affinity of at least about $10^7M^{-1}$, in some embodiments at least about $10^8M^{-1}$, in some embodiments at least about $10^9M^{-1}$, $10^{10}M^{-1}$, $10^{11}M^{-1}$ or greater, e.g., up to $10^{13}M^{-1}$ or greater.

Site saturation mutagenesis in and adjacent to the CDRs of two anti-TFPI parental antibodies, designated herein as 2A8 and 4B7, was utilized to optimize the antibodies for affinity and functional activity. It is also contemplated that the same optimization may be performed on any of the antibodies described in the previous PCT/US2009/052702.

In some embodiments, site saturation mutagenesis of the CDRs may be done on the anti-TFPI antibodies. For 2A8, the CDRs in the heavy chain shown in SEQ ID NO:1 correspond to residues FTFRSYGMS (residues 27 to 35) (SEQ ID NO: 35), SIRGSSSSTYYADSVKG (residues 50 to 66) (SEQ ID NO: 36), and KYRYWFDY (residues 99 to 106) (SEQ ID NO 37). For the 2A8 light chain shown in SEQ ID NO:2, the CDRs correspond to residues SGDNLRNYYAH (residues 23 to 33) (SEQ ID NO: 38), YYDNNRPS (residues 48 to 55) (SEQ ID NO: 39), and QSWDDGVPV (residues 88 to 96) (SEQ ID NO: 40). For 4B7, the CDRs in the heavy chain shown in SEQ ID NO: 3 correspond to residues DSVSSNSAAWS (residues 27 to 37) (SEQ ID NO: 41), IIYKRSKWYNDYAVSVKS (residues 52 to 70) (SEQ ID NO: 42), and WHSDKHWGFDY (residues 102 to 112) (SEQ ID NO: 43). For the 4B7 light chain shown in SEQ ID NO:4, the CDRs correspond to residues RSSQSLVFSDGNTYLN (residues 24 to 39) (SEQ ID NO: 44), KGSNRAS (residues 55 to 61) (SEQ ID NO: 45), and QQYDSYPLT (residues 94 to 102) (SEQ ID NO: 46) of SEQ ID NO: 4. A modification may be made in any of the six CDRs individually or combinations of modifications may be made. Further, two or more modifications may be made in a single CDR. In other embodiments, modifications may also be introduced in close proximity to the CDRs, for example about 3 or 4 residues on either side of each CDR.

Briefly, single and/or multiple amino acid modifications were introduced and analyzed to optimize, e.g. improve the affinity, of parental antibodies 2A8 and 4B7. First, single amino acid modifications were introduced into the six CDRs or adjacent to the CDRs of each antibody followed by analysis of TFPI-binding properties. Modifications that increased binding signal to TFPI were selected for combination with one or more other modifications and analyzed for further increase of the binding signal. After each analysis, selected antibody variants were used to measure their affinity to TFPI and activity in blocking TFPI activity and shortening clotting time. Thus, in some embodiments, provided is an isolated monoclonal antibody that binds to human tissue factor pathway inhibitor having increased affinity to TFPI as compared to the unmodified parental antibodies, Further, in some embodiments, provided is an isolated monoclonal antibody that binds to human tissue factor pathway inhibitor having increased blocking activity of TFPI as compared to the unmodified parental antibodies. In some embodiments, provided is an isolated monoclonal antibody that binds to human tissue factor pathway inhibitor having a shortened clotting time as compared to the unmodified parental antibodies.

In some embodiments, additional amino acid modifications were introduced to reduce divergence from the germline sequence. In other embodiments, amino acid modifications were introduced to facilitate antibody production for large scale production processes.

The antibody may be species specific or may cross react with multiple species. In some embodiments, the antibody may specifically react or cross react with TFPI of human, mouse, rat, rabbit, guinea pig, monkey, pig, dog, cat or other mammalian species.

The antibody may be of any of the various classes of antibodies, such as without limitation an IgG1, an IgG2, an IgG3, an IgG4, an IgM, an IgA1, an IgA2, a secretory IgA, an IgD, and an IgE antibody.

In one embodiment, provided is an isolated fully human monoclonal antibody to human tissue factor pathway inhibitor.

In another embodiment, provided is an isolated fully human monoclonal antibody to Kunitz domain 2 of human tissue factor pathway inhibitor.

2A8 Variants

Accordingly, in some embodiments, provided is an isolated monoclonal antibody that binds to human tissue factor pathway inhibitor, wherein the antibody comprises a heavy chain comprising an amino acid sequence shown in SEQ ID NO:1, wherein said amino acid sequence comprises one or more amino acid modifications. In some embodiments, the modification of the heavy chain of 2A8 is a substitution, an insertion or a deletion.

In some embodiments, the substitutions are located in the CDRs of the heavy chain of 2A8. In other embodiments, the substitutions are located outside the CDRs of the heavy chain of 2A8.

In some embodiments, the substitution of the heavy chain of 2A8 is at a position selected from S31, G33, S35, I51, S54, S55, K99 and F104. In some embodiments, the substitution of the heavy chain of 2A8 may also include a position selected from Q1, R30, M34, S50, R52 and S56. For example, the substitution may be selected from Q1E, R30S, S31P, S31Y, G33A, G33K, G33P, M34I, M34K, S35L, S35D, S50A, I52D, I51E, R52S, S54F, S54D, S55A, S55G, S55R, S56G, K99V, K99L, and F104Y. Further, in some embodiments, the antibody may comprise two or more substitutions selected from Q1E, R30S, S31P, S31V, G33A, G33K, G33P, M34I, M34K, S35L, S35D, S50A, I51D, I51E, R52S, S54F, S54D, S55A, S55G, S55R, S56G, K99V, K99L, and F104Y.

In some embodiments, the heavy chain of 2A8 has the following substitutions relative to SEQ ID NO:1: S31V+I51D+S54F+K99V; G33P+S35D+S54F+K99L; S35D+I51D+S55R+K99V; S35L+S54F+K99V; S31V+G33P+S35D; S35D+I51D+K99L; S31V+I51D+S55R+K99L; S31V+S35D+I51D+K99V; G33P+I51D+S54F; I51D+S54F+K99L; S35D+K99L; S31V+G33P+I51D+S54F+K99V; S35D+I51E+S55R+K99L; S31V+K99V; S31V+I51E+S55R+K99V; S35D+S55R+K99L; S31V+S54F+K99L; S31V+I51D+S55R+K99V; S31V+S35D+S55R; S31V+S35D; S31V+I51D+S55R; S35D+S54F+S55R+

K99L; S31V+S35D+S54F S31V+S35L+I51D+S54F+K99V; and S31V+S35L+I51E+S54F+K99V.

In some embodiments, the heavy chain of 2A8 has the following substitutions relative to SEQ ID NO:1: G33A+S35D+S55R+K99L; G33P+I51D+S54F; G33P+S35D+S54F+K99L; I51D+S54F+K99L; M34I+S35D+S55R+K99L; M34K+S35D+S55R+K99L; Q1E+R30S+S35D+S55G+S56G+K99L; Q1E+R30S+S35D+S55R+S56G+K99L; Q1E+S31V+S50A+I51D+S55R+A56F+K99V; Q1E+S35D+S55R+K99L; R30S+S31V+I51D+S55R+K99V; R30S+S35D+S55R+K99L; S31V+G33A+I51D+S55R+K99V; S31V+G33P+I51D+S54F+K99V; S31V+G33P+S35D; S31V+I51D+R52S+S55R+K99V; S31V+I51D+S54F+K99V; S31V+I51D+S55R; S31V+I51D+S55R+K99L; S31V+I51D+S55R+K99V; S31V+I51D+S55R+S56G+K99V; S31V+I51E+S55R+K99V; S31V+K99V; S31V+S35D; S31V+S35D+I51D+K99V; S31V+S35D+S54F; S31V+S35D+S55R; S31V+S35L+I51D+S54F+K99V; S31V+S35L+I51E+S54F+K99V; S31V+S50A+I51D+S55R+K99V; S31V+S54F+K99L; S35D+I51D+K99L; S35D+I51D+S55R+K99V; S35D+I51E+S55R+K99L; S35D+K99L; S35D+R52S+K99L; S35D+R52S+S55R+K99L; S35D+S50A+K99L; S35D+S50A+S55R+K99L; S35D+S54F+S55R+K99L; S35D+S55G+K99L; S35D+S55R+K99L; S35D+S55R+S56G+K99L; S35D+S56G+K99L; and S35L+S54F+K99V.

In some embodiments, the heavy chain of 2A8 has one or more deletions. In some embodiments, the deletions are located in the CDRs of the heavy chain of 2A8. In other embodiments, the deletions are located outside the CDRs of the heavy chain of 2A8. In some embodiments, for example, the deletion is at a position selected from I51, S56 and S57.

Further, provided is an isolated monoclonal antibody that binds to human tissue factor pathway inhibitor, wherein the antibody comprises a light chain comprising an amino acid sequence shown in SEQ ID NO:2, wherein said amino acid sequence comprises one or more amino acid modifications. In some embodiments, the modification is a substitution, an insertion or a deletion.

In some embodiments, the substitutions are located in the CDRs of the light chain of 2A8. In other embodiments, the substitutions are located outside the CDRs of the light chain of 2A8.

In some embodiments, the substitution of the light chain of 2A8 is at a position selected from A32, Y48, N51, N52, P54, D91, D92 and V96. In some embodiments, the substitution of the light chain of 2A8 may also include a position selected from D1, I2, A13, S21, N26, R28, N29, H33, Y49, G56, E80, S89, G93, V94 and P95. For example, the substitution may be selected from D1S, I2Y, A13S, S21T, N26A, R28P, N29K, A32N, H33Y, Y48F, Y49R, N51S, N51V, N52G, P54L, G56D, E80M, S89A, D91L, D91R, D91W, D91K, D92S, D92T, G93S, V94T, P95V, P95A, V96G, V96M and V96W. Further, in some embodiments, the antibody may comprise two or more substitutions selected from D1S, I2Y, A13S, S21T, N26A, R28P, N29K, A32N, H33Y, Y48F, Y49R, N51S, N51V, N52G, P54L, G56D, E80M, S89A, D91L, D91R, D91W, D91K, D92S, D92T, G93S, V94T, P95V, P95A, V96G, V96M and V96W.

In some embodiments, the light chain of 2A8 has the following substitutions relative to SEQ ID NO:2: Y48F+N51V; Y48F+N52G; Y48F+D91K; Y48F+D91L+V96W; Y48F+D91W; Y48F+N52G+D91L+V96W; Y48F+N51V+V96W; D91L+V96W; Y48F+N51V+D91W; Y48F+N51V+D91L+V96W; N51V+D91W; Y48F+N51V+G56D+V96W; Y48F+N51V+D91L; and N51V+D91K.

In some embodiments, the light chain of 2A8 has the following substitutions relative to SEQ ID NO:2: A13S+Y48F+N51V+D91W; D1S+12Y+A13S+S21T+R28P+N29K+Y48F+E80M+D91L+D92S+V94T+V96W; D1S+I2Y+A13S+S21T+R28P+N29K+Y48F+N51S+E80M+D91L+D92S+V94T+V96W; D1S+I2Y+A13S+S21T+R28P+N29K+Y48F+N51V+E80M+D91W; D1S+I2Y+A13S+S21T+R28P+N29K+Y48F+N51V+E80M+S89A+D91W+D92S+G93S+V94T; D1S+12Y+A13S+S21T+R28P+N29K+Y48F+Y49R+N51S+E80M+D91L+D92S+V94T+V96W; D1S+I2Y+A13S+S21T+R28P+Y48F+N51V+E80M+D91W; D1S+I2Y+A13S+S21T+R28P+Y48F+N51V+E80M+S89A+D91W+D92S+G93S+V94T; D1S+Y48F+N51V+D91W; D91L+V96W; H33Y+Y48F+N51V+D91W; I2Y+Y48F+N51V+D91W; N26A+Y48F+N51V+D91W; N29K+Y48F+N51V+D91W; N51V+D91K; N51V+D91W; R28P+Y48F+N51V+D91W; S21T+Y48F+N51V+D91W; Y48F+D91K; Y48F+D91L+D92S+V96W; Y48F+D91L+G93S+V96W; Y48F+D91L+P95V+V96W; Y48F+D91L+V94T+V96W; Y48F+D91L+V96W; Y48F+D91W; Y48F+N51S+D91L+V96W; Y48F+N51V; Y48F+N51V+D91L; Y48F+N51V+D91L+V96W; Y48F+N51V+D91W; Y48F+N51V+D91W+D92S; Y48F+N51V+D91W+G93S; Y48F+N51V+D91W+P95V; Y48F+N51V+D91W+V94T; Y48F+N51V+E80M+D91W; Y48F+N51V+G56D+V96W; Y48F+N51V+S89A+D91W; Y48F+N51V+S89A+D91W+D92S+G93S+V94T+P95A; Y48F+N51V+V96W; Y48F+N52G; Y48F+N52G+D91L+V96W; and Y48F+S89A+D91L+V96W.

Also provided is an isolated monoclonal antibody that binds to human tissue factor pathway inhibitor, wherein the antibody comprises: a) a heavy chain comprising an amino acid sequence shown in SEQ ID NO:1, wherein said heavy chain amino acid sequence comprises one or more amino acid modifications; and b) a light chain comprising an amino acid sequence shown in SEQ ID NO:2, wherein said light chain amino acid sequence comprises one or more amino acid modifications. Examples of modifications that can be made are provided above.

In some embodiments, the isolated monoclonal antibody that binds to human tissue factor pathway inhibitor comprises a heavy chain comprising an amino acid sequence selected from SEQ ID NO: 5, 6, 7, 8, 9, 10, and 11.

In some embodiments, the isolated monoclonal antibody that binds to human tissue factor pathway inhibitor comprises a light chain comprising an amino acid sequence selected from SEQ ID NO: 12, 13, 14, 15, 16, 17, and 18.

In some embodiments, the isolated monoclonal antibody that binds to human tissue factor pathway inhibitor comprises: a) a heavy chain comprising an amino acid sequence selected from SEQ ID NO: 5, 6, 7, 8, 9, 10, and 11; and b) a light chain comprising an amino acid sequence selected from SEQ ID NO: 12, 13, 14, 15, 16, 17, and 18. In some embodiments, the isolated monoclonal antibody that binds to human tissue factor pathway inhibitor comprises: a) a heavy chain comprising an amino acid sequence shown in SEQ ID NO: 5; and b) a light chain comprising an amino acid sequence shown in SEQ ID NO: 12. In some embodiments, the isolated monoclonal antibody that binds to human tissue factor pathway inhibitor comprises: a) a heavy chain comprising an amino acid sequence shown in SEQ ID NO: 6; and b) a light chain comprising an amino acid sequence shown in SEQ ID NO: 13. In some embodiments, the isolated monoclonal antibody that binds to human tissue factor pathway inhibitor comprises: a) a heavy chain comprising an amino acid sequence shown in SEQ ID NO: 7;

and b) a light chain comprising an amino acid sequence shown in SEQ ID NO: 14. In some embodiments, the isolated monoclonal antibody that binds to human tissue factor pathway inhibitor comprises: a) a heavy chain comprising an amino acid sequence shown in SEQ ID NO: 8; and b) a light chain comprising an amino acid sequence shown in SEQ ID NO: 15. In some embodiments, the isolated monoclonal antibody that binds to human tissue factor pathway inhibitor comprises: a) a heavy chain comprising an amino acid sequence shown in SEQ ID NO: 9: and b) a light chain comprising an amino acid sequence shown in SEQ ID NO: 16. In some embodiments, the isolated monoclonal antibody that binds to human tissue factor pathway inhibitor comprises: a) a heavy chain comprising an amino acid sequence shown in SEQ ID NO: 10; and b) a light chain comprising an amino acid sequence shown in SEQ ID NO: 17. In some embodiments, the isolated monoclonal antibody that binds to human tissue factor pathway inhibitor comprises: a) a heavy chain comprising an amino acid sequence shown in SEQ ID NO: 11; and b) a light chain comprising an amino acid sequence shown in SEQ ID NO: 18.

4B7 Variants

Also provided is an isolated monoclonal antibody that binds to human tissue factor pathway inhibitor, wherein the antibody comprises an amino acid sequence shown in SEQ ID NO:3 comprising one or more amino acid modifications. In some embodiments, the modification of the heavy chain of 4B7 is a substitution, an insertion or a deletion.

In some embodiments, the substitutions are located in the CDRs of the heavy chain of 4B7. In other embodiments, the substitutions are located outside the CDRs of the heavy chain of 4B7.

In some embodiments, the substitution of the heavy chain of 4B7 is at a position selected from S30, N32, S57, K58, N61, D62, H103, H107, G109 and Y112. In some embodiments, the substitution of the heavy chain of 4B7 may also include a position selected from Q1, S37, G44, I53 and K55. For example, the substitution may be selected from Q1E, S30R, N32D, N32F, S33G, S37N, G44S, I53T, K55Y, S57K, S57R, K58M, N61G, N61T, D62I, D62R, D62Q, D62L, D625, D62V, D62N, D62K, H103D, H103G, H107M, G109A and Y112D. Further, in some embodiments, the antibody may comprise two or more substitutions selected from Q1E, S30R, N32D, N32E, S33G, S37N, G44S, I53T, K55Y, S57K, S57R, K58M, N61G, N61T, D62I, D62R, D62Q, D62L, D62S, D62V, D62N, D62K, H103D, H103G, H107M, G109A and Y112D.

In some embodiments, the heavy chain of 4B7 has the following substitutions relative to SEQ ID NO:3:

N32D+D62Q+H107M+Y112D; N32D+D62R+H103D+H107M+Y112D; N32D+D62R+H107M+Y112D; N32D+D62R+Y112D; D62Q+Y112D; D62R+Y112D; D62R+H107M+Y112D; N32D+D62Q+Y112D; N32D+D62R+H107M; N32D+D62S+H107M+Y112D; D62Q+H107M+Y112D; N32D+D62R+H103D; D62S+H107M+Y112D; S30R+S57K; N61G+D62V; and K58M+D62N. In some embodiments, the heavy chain of 4B7 has the following substitutions relative to SEQ ID NO:3: D62Q+H107M+Y112D; D62Q+Y112D; D62R+H107M+Y112D; D62R+Y112D; D62S+H107M+Y112D; N32D+D62K+Y112D; N32D+D62Q+H107M+Y112D; N32D+D62Q+Y112D; N32D+D62R+H103D; N32D+D62R+H103D+H107M+Y112D; N32D+D62R+H107M; N32D+D62R+H107M+Y112D; N32D+D62R+Y112D; N32D+D62S+H107M+Y112D; N32D+G44S+D62R+Y112D; N32D+I53T+D62Q+Y112D; N32D+I53T+D62R+Y112D; N32D+K55Y+D62Q+Y112D; N32D+K55Y+D62R+Y112D; N32D+S37N+D62R+Y112D; Q1E+N32D+D62R+Y112D; Q1E+N32D+G44S+K55Y+D62R+Y112D; N32D+G44S+K55Y+D62R+Y112D; S30R+S57K; N61G+D62V; and K58M+D62N.

Further, provided is an isolated monoclonal antibody that binds to human tissue factor pathway inhibitor, wherein the antibody comprises an amino acid sequence shown in SEQ ID NO:4 comprising one or more amino acid modifications. In some embodiments, the modification of the light chain of 4B7 is selected from a substitution, an insertion or a deletion.

In some embodiments, the substitutions are located in the CDRs of the light chain of 4B7. In other embodiments, the substitutions are located outside the CDRs of the light chain of 4B7.

In some embodiments, the substitution of the light chain of 4B7 is at a position selected from F31, S32, D33, N35, Y37, Y54, G56, S57, S61 and D97. In some embodiments, the substitution of the light chain of 4B7 may also include a position selected from M4, V30, T36, N39, L42, K44, Q50, L51, K55, A60 and S98. For example, the substitution may be selected from M41, M4L, V30L, F31I, F31M, F31Y, F31H, S32L, S32R, S32Y, D33F, D33R, N35I, N35L, N35T, N35V, T36N, Y37F, N39D, L42Q, K44R, Q50R, L51R, Y54F, K55L, G56D, G56A, G56V, S57Y, A60D, S61C, D97M, D97T and S98H. Further, in some embodiments, the antibody may comprise two or more substitutions selected from M4I, M4L, V30L, F31I, F31M, F31Y, S32L, S32R, S32Y, D33F, D33R, N35I, N35L, N35T, N35V, T36N, Y37F, N39D, L42Q, K44R, Q50R, Y54F, K55L, G56D, G56A, G56V, S57Y, A60D, S61C, D97M, D97T and S98H.

In some embodiments, the light chain of 4B7 has the following substitutions relative to SEQ ID NO:4: S32R+N35T; S32R+N35T+D97T: S32R+D33F+N35I; S32R+D33F+N35I+D97T; S32R+D33F+N35T; S32R+D33F; S32R+D33R+N35I; S32R+D33R+N35I+D97T; S32R+D33R; S32R+D33R+N35T; N35T+D97T; D33F+N35I; D33F+N35I+D97T; D33F+N35T+Y37F; D33R+N35I; D33R+N35I+D97T; D33R+N35T; F31I+S32R+N35I+D97T; F31I+S32R+D33F+N35I+D97T; F31I+S32R+D33F+N35T; F31I+S32R+D33R+N35T+D97T; F31I+N35I; F31T+D33F+N35I; F31I+D33F+N35I+D97T; F31I+D33R+N35I; F31I+D33R; F31M+S32L+D33R+N35I+D97T; F31M+S32R+D33F+N35I; F31M+S32R+D33F+N35I+D97T; F31M+S32R+D33F+D97T; F31M+S32R+D33R+N35I; F31M+S32R+D33R+N351+D97T; F31M+S32R+D33R; F31M+S32R+D33R+N35T; F31M+D33F+N35I; F31M+D33F; F31M+D33F+N35T; F31M+D33R+N35I; F31M+D33R; S32R+N35I; F31M+D33F+N35T+Y37F; N35V+G56D; N35L+G56A; and D33F+Y54F.

In some embodiments, the light chain of 4B7 has the following substitutions relative to SEQ ID NO:4: D33F+N35I; D33F+N35I+D97T; D33F+N35T+Y37F; D33R+N35I; D33R+N35I+D97T; D33R+N35T; F31II+S32R+D33F+N35I+D97T; F31I+D33F+N35I; F31I+D33F+N35I+D97T; F31I+D33F+N35I+K44R; F31I+D33F+N35I+L42Q; F31I+D33F+N35I+S98H; F31I+D33F+N35I+T36N; F31I+D33R; F31I+D33R+N35I; F31I+N35I; F31I+S32R+D33F+N35I+D97T; F31I+S32R+D33F+N35T; F31I+S32R+D33R+N35I+D97T; F31I+S32R+N35I+D97T; F31M+D33F; F31M+D33F+N35I; F31M+D33F+N35T; F31M+D33F+N35T+Y37F; F31M+D33R; F31M+D33R+N35I; F31M+S32L+D33R+N35I+D97T; F31M+S32R+D33F+D97T; F31M+S32R+D33F+N35I; F31M+S32R+D33F+N35I+D97T; F31M+S32R+D33R; F31M+S32R+D33R+N35I; F31M+S32R+D33R+N35I+D97T; F31M+S32R+

D33R+N35T; F31Y+S32R+D33F+N35I+D97T; M4I+S32R+D33F+N35I+D97T; M4L+S32R+D33F+N35I+D97T; N35T+D97T; S32R+D33F; S32R+D33F+N35I; S32R+D33F+N35I+A60D+D97T; S32R+D33F+N35I+D97T; S32R+D33F+N35I+D97T+S98H; S32R+D33F+N35I+G56V+D97T; S32R+D33F+N35I+K44R+D97T; S32R+D33F+N35I+K55L+D97T; S32R+D33F+N35I+L42Q+D97T; S32R+D33F+N35I+L51R+D97T; S32R+D33F+N35I+N39D+D97T; S32R+D33F+N35I+Q50R+D97T; S32R+D33F+N35I+T36N+D97T; S32R+D33F+N35T; S32R+D33R; S32R+D33R+N35I; S32R+D33R+N35I+D97T; S32R+D33R+N35T; S32R+N35I; S32R+N35T; S32R+N35T+D97T; V30L+F31I+D33F+N35I; V30L+S32R+D33F+N35I+D97T; V30L+S32R+D33F+N35I+T36N+D97T; V30L+S32R+N35I+T36N; N35V+G56D; N35L+G56A; and D33F+Y54F.

Also provided is an isolated monoclonal antibody that binds to human tissue factor pathway inhibitor, wherein the antibody comprises: a) a heavy chain comprising an amino acid sequence shown in SEQ ID NO:3, wherein said heavy chain amino acid sequence comprises one or more amino acid modifications; and b) a light chain comprising an amino acid sequence shown in SEQ ID NO:4, wherein said light chain amino acid sequence comprises one or more amino acid modifications. Examples of modifications that can be made are provided above.

In some embodiments, the isolated monoclonal antibody that binds to human tissue factor pathway inhibitor comprises a heavy chain comprising an amino acid sequence selected from SEQ ID NO: 19, 20, 21, 22, 23, 24, 25 and 26.

In some embodiments, the isolated monoclonal antibody that binds to human tissue factor pathway inhibitor comprises a light chain comprising an amino acid sequence selected from SEQ ID NO: 27, 28, 29, 30, 31, 32, 33 and 34.

In some embodiments, the isolated monoclonal antibody that binds to human tissue factor pathway inhibitor comprises: a) a heavy chain comprising an amino acid sequence selected from SEQ ID NO: 19, 20, 21, 22, 23, 24, 25 and 26; and b) a light chain comprising an amino acid sequence selected from SEQ ID NO: 27, 28, 29, 30, 31, 32, 33 and 34. In some embodiments, the isolated monoclonal antibody that binds to human tissue factor pathway inhibitor comprises: a) a heavy chain comprising an amino acid sequence shown in SEQ ID NO: 19; and b) a light chain comprising an amino acid sequence shown in SEQ ID NO: 27. In some embodiments, the isolated monoclonal antibody that binds to human tissue factor pathway inhibitor comprises: a) a heavy chain comprising an amino acid sequence shown in SEQ ID NO: 20; and b) a light chain comprising an amino acid sequence shown in SEQ ID NO: 28. In some embodiments, the isolated monoclonal antibody that binds to human tissue factor pathway inhibitor comprises: a) a heavy chain comprising an amino acid sequence shown in SEQ ID NO: 21; and b) a light chain comprising an amino acid sequence shown in SEQ ID NO: 29. In some embodiments, the isolated monoclonal antibody that binds to human tissue factor pathway inhibitor comprises: a) a heavy chain comprising an amino acid sequence shown in SEQ ID NO: 22; and b) a light chain comprising an amino acid sequence shown in SEQ ID NO: 30. In some embodiments, the isolated monoclonal antibody that binds to human tissue factor pathway inhibitor comprises: a) a heavy chain comprising an amino acid sequence shown in SEQ ID NO: 23; and b) a light chain comprising an amino acid sequence shown in SEQ ID NO: 31. In some embodiments, the isolated monoclonal antibody that binds to human tissue factor pathway inhibitor comprises: a) a heavy chain comprising an amino acid sequence shown in SEQ ID NO: 24; and b) a light chain comprising an amino acid sequence shown in SEQ ID NO: 32. In some embodiments, the isolated monoclonal antibody that binds to human tissue factor pathway inhibitor comprises: a) a heavy chain comprising an amino acid sequence shown in SEQ ID NO: 25; and b) a light chain comprising an amino acid sequence shown in SEQ ID NO: 33. In some embodiments, the isolated monoclonal antibody that binds to human tissue factor pathway inhibitor comprises: a) a heavy chain comprising an amino acid sequence shown in SEQ ID NO: 26; and b) a light chain comprising an amino acid sequence shown in SEQ ID NO: 34.

2A8/4B7 Variant Combinations

It is also contemplated that the isolated monoclonal antibody that binds to human tissue factor pathway inhibitor may comprise combinations of the heavy and light chains of 2A8 and 4B7.

Accordingly, provided is an isolated monoclonal antibody that binds to human tissue factor pathway inhibitor, wherein the antibody comprises: a) a heavy chain of 2A8 comprising an amino acid sequence shown in SEQ ID NO:1, wherein said heavy chain amino acid sequence comprises one or more amino acid modifications; and b) a light chain of 4B7 comprising an amino acid sequence shown in SEQ ID NO:4, wherein said light chain amino acid sequence comprises one or more amino acid modifications. Examples of modifications that can be made are provided above.

Also provided is an isolated monoclonal antibody that binds to human tissue factor pathway inhibitor, wherein the antibody comprises: a) a heavy chain 4B7 comprising an amino acid sequence shown in SEQ ID NO:3, wherein said heavy chain amino acid sequence comprises one or more amino acid modifications; and b) a light chain of 2A8 comprising an amino acid sequence shown in SEQ ID NO:2, wherein said light chain amino acid sequence comprises one or more amino acid modifications. Examples of modifications that can be made are provided above.

In some embodiments, provided is an isolated monoclonal antibody that binds to human tissue factor pathway inhibitor, wherein the antibody comprises: a) a heavy chain comprising an amino acid sequence selected from the group consisting of SEQ ID NO:5, 6, 7, 8, 9, 10, 11, 19, 20, 21, 22, 23, 24, 25, and 26; and b) a light chain comprising an amino acid sequence selected from the group consisting of SEQ ID NO:12, 13, 14, 15, 16, 17, 18, 27, 28, 29, 30, 31, 32, 33, and 34.

Nucleic Acids, Vectors and Host Cells

Also provided are isolated nucleic acid molecules encoding any of the monoclonal antibodies described above.

Thus, provided is an isolated nucleic acid molecule encoding an antibody that binds to human tissue factor pathway inhibitor, wherein the antibody comprises a heavy chain comprising an amino acid sequence shown in SEQ ID NO:1, wherein said heavy chain amino acid sequence comprises one or more amino acid modifications. Examples of such modifications are described above.

Also provided is an isolated nucleic acid molecule encoding an antibody that binds to human tissue factor pathway inhibitor, wherein the antibody comprises a light chain comprising an amino acid sequence shown in SEQ ID NO:2, wherein said light chain amino acid sequence comprises one or more amino acid modifications. Examples of such modifications are described above.

Also provided is an isolated nucleic acid molecule encoding an antibody that binds to human tissue factor pathway inhibitor, wherein the antibody comprises a heavy chain comprising an amino acid sequence shown in SEQ ID NO:3, wherein said heavy chain amino acid sequence comprises one or more amino acid modifications. Examples of such modifications are described above.

Also provided is an isolated nucleic acid molecule encoding an antibody that binds to human tissue factor pathway inhibitor, wherein the antibody comprises a light chain comprising an amino acid sequence shown in SEQ ID NO:4, wherein said light chain amino acid sequence comprises one or more amino acid modifications. Examples of such modifications are described above.

Further, also provided are vectors comprising the isolated nucleic acid molecules encoding any of the monoclonal antibodies described above and host cells comprising such vectors.

Methods of Preparing Antibodies to TFPI

The monoclonal antibody may be produced recombinantly by expressing a nucleotide sequence encoding the variable regions of the monoclonal antibody according to the embodiments of the invention in a host cell. With the aid of an expression vector, a nucleic acid containing the nucleotide sequence may be transfected and expressed in a host cell suitable for the production. Accordingly, also provided is a method for producing a monoclonal antibody that binds with human TFPI comprising:

(a) transfecting a nucleic acid molecule encoding a monoclonal antibody of the invention into a host cell, (b) culturing the host cell so to express the monoclonal antibody in the host cell, and optionally (c) isolating and purifying the produced monoclonal antibody, wherein the nucleic acid molecule comprises a nucleotide sequence encoding a monoclonal antibody of the present invention.

In one example, to express the antibodies, or antibody fragments thereof, DNAs encoding partial or full-length light and heavy chains obtained by standard molecular biology techniques are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vectors or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain encoding genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Examples of regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or β-globin promoter.

In addition to the antibody chain genes and regulatory sequences, the recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Examples of selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Examples of mammalian host cells for expressing the recombinant antibodies include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells, HKB11 cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods, such as ultrafiltration, size exclusion chromatography, ion exchange chromatography and centrifugation.

Use of Partial Antibody Sequences to Express Intact Antibodies

Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. Sci. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. It is not necessary to obtain the entire DNA sequence of a particular antibody in order to recreate an intact recombinant antibody having binding properties similar to those of the original antibody (see WO 99/45962). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. For this reason, it is necessary to use the corresponding germline leader sequence for expression constructs. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts are used to design an overlapping set of synthetic oligonucleotides to create synthetic V sequences with identical amino acid coding capacities as the natural sequences. The synthetic heavy and light chain sequences can differ from the natural sequences. For example: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and restriction sites are engineered upstream or downstream of the translation initiation sites.

For both the heavy and light chain variable regions, the optimized coding, and corresponding non-coding, strand sequences are broken down into 30-50 nucleotide sections at approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed heavy and light chain variable regions are then combined with cloned promoter, translation initiation, constant region, 3' untranslated, polyadenylation, and transcription termination sequences to form expression vector constructs. The heavy and light chain expression constructs can be combined into a single vector, co-transfected, serially transfected, or separately transfected into host cells which are then fused to form a host cell expressing both chains.

Thus, in another aspect, the structural features of a human anti-TFPI antibody are used to create structurally related human anti-TFPI antibodies that retain the function of binding to TFPI. More specifically, one or more CDRs of the specifically identified heavy and light chain regions of the monoclonal antibodies of the invention can be combined recombinantly with known human framework regions and CDRs to create additional, recombinantly-engineered, human anti-TFPI antibodies of the invention.

Pharmaceutical Compositions

Also provided are pharmaceutical compositions comprising therapeutically effective amounts of anti-TFPI monoclonal antibody and a pharmaceutically acceptable carrier. "Pharmaceutically acceptable carrier" is a substance that may be added to the active ingredient to help formulate or stabilize the preparation and causes no significant adverse toxicological effects to the patient. Examples of such carriers are well known to those skilled in the art and include water, sugars such as maltose or sucrose, albumin, salts such as sodium chloride, etc. Other carriers are described for example in Remington's Pharmaceutical Sciences by E. W. Martin. Such compositions will contain a therapeutically effective amount of at least one anti-TFPI monoclonal antibody.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. The composition is preferably formulated for parenteral injection. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In some cases, it will include isotonic agents, for example, sugars, polyalcohols such as mannitol, sorbitol, or sodium chloride in the composition.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, some methods of preparation are vacuum drying and freeze-drying (lyophilization) that yield a powder of the active ingredient plus any additional desired ingredient from a previously sterile-filtered solution thereof.

Pharmaceutical Uses

The monoclonal antibody can be used for therapeutic purposes for treating genetic and acquired deficiencies or defects in coagulation. For example, the monoclonal antibodies in the embodiments described above may be used to block the interaction of TFPI with FXa, or to prevent TFPI-dependent inhibition of the TF/FVIIa activity. Additionally, the monoclonal antibody may also be used to restore the TF/FVIIa-driven generation of FXa to bypass the insufficiency of FVIII- or FIX-dependent amplification of FXa.

The monoclonal antibodies have therapeutic use in the treatment of disorders of hemostasis such as thrombocytopenia, platelet disorders and bleeding disorders (e.g., hemophilia A, hemophilia B and hemophlia C). Such disorders may be treated by administering a therapeutically effective amount of the anti-TFPI monoclonal antibody to a patient in need thereof. The monoclonal antibodies also have therapeutic use in the treatment of uncontrolled bleeds in indications such as trauma and hemorrhagic stroke. Thus, also provided is a method for shortening the bleeding time comprising administering a therapeutically effective amount of an anti-TFPI monoclonal antibody of the invention to a patient in need thereof.

The antibodies can be used as monotherapy or in combination with other therapies to address a hemostatic disorder. For example, co-administration of one or more antibodies of the invention with a clotting factor such as factor VIIa, factor VIII or factor IX is believed useful for treating hemophilia. In one embodiment, provided is a method for treating genetic and acquired deficiencies or defects in coagulation comprising administering (a) a first amount of a monoclonal antibody that binds to human tissue factor pathway inhibitor and (b) a second amount of factor VIII or factor IX, wherein said first and second amounts together are effective for treating said deficiencies or defect. In another embodiment, provided is a method for treating genetic and acquired deficiencies or defects in coagulation comprising administering (a) a first amount of a monoclonal antibody that binds to human tissue factor pathway inhibitor and (b) a second amount of factor VIII or factor IX, wherein said first and second amounts together are effective for treating said deficiencies or defects, and further wherein factor VII is not coadministered. The invention also includes a pharmaceutical composition comprising a therapeutically effective amount of the combination of a monoclonal antibody of the invention and factor VIII or factor IX, wherein the composition does not contain factor VII. "Factor VII" includes factor VII and factor VIIa. These combination therapies are likely to reduce the necessary infusion frequency of the clotting factor. By co-administration or combination therapy is meant administration of the two therapeutic drugs each formulated separately or formulated together in one composition, and, when formulated separately, administered either at approximately the same time or at different times, but over the same therapeutic period.

In some embodiments, one or more antibodies described herein can be used in combination to address a hemostatic disorder. For example, co-administration of two or more of the antibodies described herein is believed useful for treating hemophilia or other hemostatic disorder.

The pharmaceutical compositions may be parenterally administered to subjects suffering from hemophilia A or B at a dosage and frequency that may vary with the severity of the bleeding episode or, in the case of prophylactic therapy, may vary with the severity of the patient's clotting deficiency.

The compositions may be administered to patients in need as a bolus or by continuous infusion. For example, a bolus administration of an inventive antibody present as a Fab fragment may be in an amount of from 0.0025 to 100 mg/kg body weight, 0.025 to 0.25 mg/kg, 0.010 to 0.10 mg/kg or 0.10-0.50 mg/kg. For continuous infusion, an inventive antibody present as an Fab fragment may be administered at 0.001 to 100 mg/kg body weight/minute, 0.0125 to 1.25 mg/kg/min., 0.010 to 0.75 mg/kg/min., 0.010 to 1.0 mg/kg/min. or 0.10-0.50 mg/kg/min. for a period of 1-24 hours, 1-12 hours, 2-12 hours, 6-12 hours, 2-8 hours, or 1-2 hours. For administration of an inventive antibody present as a full-length antibody (with full constant regions), dosage amounts may be about 1-10 mg/kg body weight, 2-8 mg/kg, or 5-6 mg/kg. Such full-length antibodies would typically be administered by infusion extending for a period of thirty minutes to three hours. The frequency of the administration would depend upon the severity of the condition. Frequency could range from three times per week to once every two weeks to six months.

Additionally, the compositions may be administered to patients via subcutaneous injection. For example, a dose of 10 to 100 mg anti-TFPI antibody can be administered to patients via subcutaneous injection weekly, biweekly or monthly.

As used herein, "therapeutically effective amount" means an amount of an anti-TFPI monoclonal antibody or of a combination of such antibody and factor VIII or factor IX that is needed to effectively increase the clotting time in vivo or otherwise cause a measurable benefit in vivo to a patient in need. The precise amount will depend upon numerous factors, including, but not limited to the components and physical characteristics of the therapeutic composition, intended patient population, individual patient considerations, and the like, and can readily be determined by one skilled in the art.

EXAMPLES

Example 1

Cloning, Expression and Quantification of Antibody Expression Levels

The heavy and light chain of the wild-type Fabs 2A8 and 4B7 carrying a c-myc-tag and a hexa-histidine tag at the C-terminus of the heavy chain were subcloned into the pET28a bacterial expression vector (Novagen/Merck Chemicals Ltd., Nottingham, UK) and transformed into Top10F' cells (Invitrogen GmbH, Karlsruhe, Germany). Alternatively, other bacterial expression vectors (e.g. pQE vector system, Qiagen GmbH, Hilden, Germany) and strains (e.g. DH5α, Invitrogen GmbH, Karlsruhe, Germany) can be used. Variants were generated by standard oligo-based site-directed mutagenesis and confirmed by DNA sequencing. In particular, amino acid residues within or surrounding complementary determining regions were modified within the heavy and/or the light chain.

To be able to use wild-type or mutant antibodies as competitors, epitope-tags located at are C-terminus of the heavy chain were either removed or replaced using standard PCR-based techniques. In particular, for 4B7 the c-myc-tag was exchanged to a haemagglutinin (HA) epitope tag for all variants analyzed. In contrast, 4B7 wild-type or variants used as competitors carried a c-myc-tag. In case of 2A8, the c-myc-epitope tag was either replaced by a HA-tag or deleted, resulting in a variant that only displayed a 6×Histidine epitope tag at its C-terminus.

For expression, variants were transformed into the BL21starDE3 Escherichia coli strain (Invitrogen, C6010-03), inoculated into an overnight culture in LB medium containing kanamycin (30 μg/ml) and incubated at 37° C. for 18 hours. Expression cultures were generated by inoculating the overnight culture 1:20 into fresh LB medium with kanamycin (30 μg/ml). After 6 hours, 1 mM isopropyl-b-D-1-thiogalactopyranoside (Roth, 2316.5) was added to induce antibody expression and the cultures were incubated for additional 18 hours at 30° C. Alternatively, overnight cultures were inoculated 1:20 into the autoinduction medium Overnight Express TB medium (Merck, 71491) and incubated at 30' C. for 24 hours.

For quantification of expression levels an ELISA approach was used. Briefly, MTP plates (Nunc maxisorp black, 460518) were incubated with a Fab-specific antibody (Sigma, 15260) diluted in coating buffer (Candor Bioscience GmbH, 121500) at 4° C. over night, washed with PBST (phosphate buffered saline: 137 mM NaCl, Merck 1.06404.5000; 2.7 mM KCl, Merck 1.04936.1000; 10 mM $Na_2HPO_4$, Merck 1.06586.2500, 1.8 mM $KH_2PO_4$, Merck 1.04871.5000; containing 0.05% Tween 20 Acros Organics, 233360010), blocked with 2% milk in PBST for 1 h at room temperature and washed again. Cultures were diluted in 0.25% skim milk (Fluka analytical, 70166) in PBS and bound to the MTP plates for 1 h at room temperature. After washing with PBST, captured antibodies were incubated with a HRP-coupled anti-Fab antibody (Sigma, A0293) and detected by incubating the plate with 10 μM amplex red substrate (Invitrogen, A12222) for 10 to 30 minutes at room temperature in the dark followed by fluorescence measurement. Expression levels were normalized after determining the concentration relative to the wild-type purified antibody (2A8 or 4B7).

Example 2

Determination of Activity and Interspecies Cross Reactivity of Generated Antibody Variants To determine the activity of the mutated antibody variants on human or mouse TFPI (American Diagnostica, 4900B and R&D Systems, 2975-P1, respectively) an equilibrium or competitive ELISA assay format was used. Briefly, MTP plates (either Mesoscale Discovery, L21XA-4 or Nunc maxisorp black, 460518) were coated with 0.04-2 μg/ml either human or mouse TFPI diluted in phosphate buffered saline (PBS) or in coating buffer (Candor Bioscience GmbH, 121500), respectively and incubated over night at 4° C. After washing, plates were blocked with 3% bovine serum albumin (Sigma, A4503) in PBST for 1 hour at room temperature and the washing step was repeated. For binding of the antibodies 10-25 μl of culturing supernatants normalized to their respective antibody expression level (if not otherwise indicated) were added to the plates for 1 hour at RT followed by washing with PBST. Bound wild-type and variants were then either detected by an epitope tag specific antibody or a competition step was included. For competition, 50-300 nM competitor or free antigen was added and incubated for 20 minutes to 24 hours at room temperature. After washing, the remaining variants were detected with an epitope tag specific antibody either coupled to horseradish peroxidase (Biomol, anti-c-myc A190-105P for 2A8 variants and anti-IIAA190-108P for 4B7 variants) or by an anti-myc (Sigma, C3956) or anti-HA antibody (Sigma, H6908) which was previously labeled with a sulfo-NHS reagent according to the manufacturer's instructions for electrochemiluminiscent detection (Mesoscale Discovery, R91AN-1). For signal detection in maxisorp plates 10 μM amplex red substrate (Invitrogen,A12222) was added and incubated for 10 to 30 minutes at room temperature in the dark followed by fluorescence measurement. For the detection in MSD plates MSD read buffer T was diluted to 2× in $H_2O$ (Mesoscale Discovery, R92TC-1), added to the plates and the electrochemiluminiscence signal was detected at 620 nm using the Mesoscale Discovery Sector Imager 6000.

Example 3

Single and Multiple Amino Acid Substitutions

Provided in Table 1 are several examples of single amino acid substitutions introduced into the heavy or light chain of 2A8. The expression level of the variants was analyzed in quadruples in the quantification ELISA. After normalization to the respective expression level, performance was analyzed in quadruples in the competitive ELISA on human and murine TFPI and variant to wild-type (wt) ratios were determined. Errors were calculated by error propagation from the standard deviations.

TABLE 1

Analysis of single amino acid substitutions within 2A8.

| | hTFPI | | mTFPI | |
|---|---|---|---|---|
| 2A8 variants | variant/wild-type | error | variant/wild-type | error |
| HC_S31P | 3.6 | 0.5 | 2.4 | 0.3 |
| HC_S31V | 9.7 | 1.1 | 7.4 | 4.1 |
| HC_G33K | 1.8 | 0.2 | 0.7 | 0.1 |
| HC_G33P | 5.1 | 0.6 | 2.9 | 0.4 |
| HC_S35L | 1.7 | 0.1 | 1.5 | 0.2 |
| HC_S35D | 4.3 | 0.6 | 2.6 | 0.6 |
| HC_I51D | 3.9 | 0.3 | 1.4 | 0.2 |
| HC_I51E | 7.3 | 0.6 | 0.7 | 0.1 |
| HC_S54F | 6.5 | 0.6 | 3.1 | 0.6 |
| HC_S54D | 1.7 | 0.2 | 1.2 | 0.2 |
| HC_S55A | 2.0 | 0.3 | 1.2 | 0.2 |
| HC_S55R | 4.4 | 1.1 | 2.1 | 0.3 |
| HC_K99V | 7.5 | 0.9 | 3.9 | 0.5 |
| HC_K99L | 13.5 | 1.4 | 10.8 | 2.8 |
| HC_F104Y | 2.0 | 0.3 | 1.5 | 0.2 |
| LC_A32N | 3.5 | 0.4 | 2.0 | 0.3 |
| LC_Y48F | 4.6 | 0.6 | 3.2 | 0.7 |
| LC_N51V | 4.4 | 0.4 | 2.0 | 0.4 |
| LC_N52G | 3.4 | 0.5 | 1.5 | 0.2 |
| LC_P54L | 5.3 | 0.8 | 2.7 | 0.5 |
| LC_D91L | 4.2 | 0.3 | 1.6 | 0.5 |
| LC_D91R | 3.1 | 0.5 | 2.0 | 0.3 |
| LC_D91W | 7.4 | 0.7 | 4.0 | 0.7 |
| LC_D91K | 3.5 | 0.4 | 1.4 | 0.2 |
| LC_D92S | 3.8 | 0.5 | 2.6 | 0.3 |
| LC_D92T | 2.6 | 0.4 | 1.2 | 0.2 |
| LC_V96G | 3.2 | 0.4 | 1.2 | 0.2 |
| LC_V96M | 3.5 | 0.5 | 1.5 | 0.2 |
| LC_V96W | 4.0 | 0.4 | 4.3 | 0.6 |
| HC_S31P | 3.6 | 0.5 | 2.4 | 0.3 |
| HC_S31V | 9.7 | 1.1 | 7.4 | 4.1 |

TABLE 1-continued

Analysis of single amino acid substitutions within 2A8.

| 2A8 variants | hTFPI variant/wild-type | hTFPI error | mTFPI variant/wild-type | mTFPI error |
|---|---|---|---|---|
| HC_G33K | 1.8 | 0.2 | 0.7 | 0.1 |
| HC_G33P | 5.1 | 0.6 | 2.9 | 0.4 |
| HC_S35L | 1.7 | 0.1 | 1.5 | 0.2 |
| HC_S35D | 4.3 | 0.6 | 2.6 | 0.6 |
| HC_I51D | 3.9 | 0.3 | 1.4 | 0.2 |
| HC_I51E | 7.3 | 0.6 | 0.7 | 0.1 |
| HC_S54F | 6.5 | 0.6 | 3.1 | 0.6 |
| HC_S54D | 1.7 | 0.2 | 1.2 | 0.2 |
| HC_S55A | 2.0 | 0.3 | 1.2 | 0.2 |
| HC_S55R | 4.4 | 1.1 | 2.1 | 0.3 |
| HC_K99V | 7.5 | 0.9 | 3.9 | 0.5 |
| HC_K99L | 13.5 | 1.4 | 10.8 | 2.8 |
| HC_F104Y | 2.0 | 0.3 | 1.5 | 0.2 |
| LC_A32N | 3.5 | 0.4 | 2.0 | 0.3 |
| LC_Y48F | 4.6 | 0.6 | 3.2 | 0.7 |
| LC_N51V | 4.4 | 0.4 | 2.0 | 0.4 |
| LC_N52G | 3.4 | 0.5 | 1.5 | 0.2 |
| LC_P54L | 5.3 | 0.8 | 2.7 | 0.5 |
| LC_D91L | 4.2 | 0.3 | 1.6 | 0.5 |
| LC_D91R | 3.1 | 0.5 | 2.0 | 0.3 |
| LC_D91W | 7.4 | 0.7 | 4.0 | 0.7 |
| LC_D91K | 3.5 | 0.4 | 1.4 | 0.2 |
| LC_D92S | 3.8 | 0.5 | 2.6 | 0.3 |
| LC_D92T | 2.6 | 0.4 | 1.2 | 0.2 |
| LC_V96G | 3.2 | 0.4 | 1.2 | 0.2 |

TABLE 1-continued

Analysis of single amino acid substitutions within 2A8.

| 2A8 variants | hTFPI variant/wild-type | hTFPI error | mTFPI variant/wild-type | mTFPI error |
|---|---|---|---|---|
| LC_V96M | 3.5 | 0.5 | 1.5 | 0.2 |
| LC_V96W | 4.0 | 0.4 | 4.3 | 0.6 |

Provided in Table 2 are some examples of combined amino acid substitutions within 2A8 TFPI antibodies. While not every combination is provided in Table 2, it is contemplated that the TFPI antibody may comprise any combination of modifications provided. The expression level of variants was analyzed in quadruples in the quantification ELISA. If not otherwise indicated, variants were normalized to the respective expression level and performance was analyzed in quadruples in the competitive ELISA on human and murine TFPI followed by calculation of variant to reference (HC_K99L) ratios. Values are marked with "#" in case variant performance was analyzed without prior normalization and variant to reference ratios were normalized to the expression level by dividing the assay signal by the expression level. In cases were a different reference was used in the competitive ELISA and variants were analyzed without prior normalization, values are marked with "*". For these variants, the value listed in the table was calculated by multiplying the ratios variant/alternative reference with alternative reference/HC_K99L. Errors were calculated by error propagation from the standard deviations.

TABLE 2

Example of multiple amino acid substitutions within 2A8.

| 2A8 HC | | | | | | | | | | | | | 2A8 LC | | | | | | | | |
|---|---|---|---|---|---|---|---|---|---|---|---|---|---|---|---|---|---|---|---|---|---|
| Q1 | R30 | S31 | G33 | M34 | S35 | S50 | I51 | R52 | S54 | S55 | S56 | K99 | D1 | I2 | A13 | S21 | N26 | R28 | N29 | H33 | Y48 |
| | | V | | | | | D | | F | | | V | | | | | | | | | F |
| | | | P | | D | | | | F | | | L | | | | | | | | | F |
| | | | | | D | | D | | | R | | V | | | | | | | | | F |
| | | | | | L | | | | F | | | V | | | | | | | | | F |
| | | V | P | | D | | | | | | | | | | | | | | | | F |
| | | | | | D | | D | | | | | L | | | | | | | | | F |
| | | V | | | | | D | | | R | | L | | | | | | | | | F |
| | | V | | | D | | D | | | | | V | | | | | | | | | F |
| | | | P | | | | D | | F | | | | | | | | | | | | F |
| | | | | | | | D | | F | | | L | | | | | | | | | |
| | | V | | | D | | | | F | | | | | | | | | | | | F |
| | | | | | D | | | | | | | L | | | | | | | | | |
| | | V | P | | | | D | | F | | | V | | | | | | | | | F |
| | | | | | D | | E | | | R | | L | | | | | | | | | F |
| | | V | | | | | | | | | | V | | | | | | | | | |
| | | V | | | | | E | | | R | | V | | | | | | | | | F |
| | | | | | D | | | | | | | L | | | | | | | | | F |
| | | V | | | | | | | F | | | L | | | | | | | | | |
| | | V | P | | D | | | | | | | | | | | | | | | | F |
| | | | | | D | | | | | R | | L | | | | | | | | | F |
| | | V | | | D | | | | | R | | | | | | | | | | | F |
| | | V | | | D | | | | | | | | | | | | | | | | F |
| | | V | | | | | D | | | R | | | | | | | | | | | F |
| | | | | | D | | | | F | R | | L | | | | | | | | | |
| | | V | | | L | | D | | F | | | V | | | | | | | | | |
| | | V | | | L | | E | | F | | | V | | | | | | | | | |
| | | | | | D | | | | | | | L | | | | | | | | | |
| | | | | | D | | | | | | | L | | | | | | | | | F |
| | | V | | | | | D | | | R | | V | | | | | | | | | F |
| | | | | | D | | | | | R | | L | | | | | | | | | F |
| | | | | | D | | | | | R | | L | S | | | | | | | | F |
| | | | | | D | | | | | R | | L | | Y | | | | | | | F |
| | | | | | D | | | | | R | | L | | | S | | | | | | F |
| | | | | | D | | | | | R | | L | | | | T | | | | | F |
| | | | | | D | | | | | R | | L | | | | | A | | | | F |
| | | | | | D | | | | | R | | L | | | | | | P | | | F |

TABLE 2-continued

Example of multiple amino acid substitutions within 2A8.

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | | | | | | | D | | | | | | R | | | L | | | | | | | | | K | | | F | | |
| | | | | | | | D | | | | | | R | | | L | | | | | | | | | | | Y | F | | |
| | | | | | | | D | | | | | | R | | | L | | | | | | | | | | | | F | | |
| | | | | | | | D | | | | | | R | | | L | | | | | | | | | | | | F | | |
| | | | | | | | D | | | | | | R | | | L | | | | | | | | | | | | F | | |
| | | | | | | | D | | | | | | R | | | L | | | | | | | | | | | | F | | |
| | | | | | | | D | | | | | | R | | | L | | | | | | | | | | | | F | | |
| | | | | | | | D | | | | | | R | | | L | | | | | | | | | | | | F | | |
| | | | | | | | D | | | | | | R | | | L | | | | | | | | | | | | F | | |
| E | | | | | | | D | | | | | | R | | | L | | | | | | | | | | | | F | | |
| | S | | | | | | D | | | | | | R | | | L | | | | | | | | | | | | F | | |
| | | | | A | | | D | | | | | | R | | | L | | | | | | | | | | | | F | | |
| | | | | | I | | D | | | | | | R | | | L | | | | | | | | | | | | F | | |
| | | | | | K | | D | | | | | | R | | | L | | | | | | | | | | | | F | | |
| | | | | | | | D | A | | | | | R | | | L | | | | | | | | | | | | F | | |
| | | | | | | | D | | | S | | | R | | | L | | | | | | | | | | | | F | | |
| | | | | | | | D | | | | | | R | G | | L | | | | | | | | | | | | F | | |
| E | S | | | | | | D | | | | | | R | G | | L | S | Y | S | T | | | P | K | | | | F | | |
| E | S | | | | | | D | | | | | | R | G | | L | | | | | | | | | | | | F | | |
| | | | | | | | D | | | | | | R | | | L | S | Y | S | T | | | P | K | | | | F | | |
| E | S | | | | | | D | | | | | | R | G | | L | S | Y | S | T | | | P | | | | | F | | |
| E | S | | | | | | D | | | | | | R | G | | L | S | Y | S | T | | | P | K | | | | F | | |
| E | S | | | | | | D | | | | | | R | G | | L | S | Y | S | T | | | P | | | | | F | | |
| | | | | | | | D | | | | | | | | | L | | | | | | | | | | | | F | | |
| | | | | | | | D | | | | | | | | | L | | | | | | | | | | | | F | | |
| | | | | | | | D | | | | | | | | | L | | | | | | | | | | | | F | | |
| | | | | | | | D | | | | | | | | | L | | | | | | | | | | | | F | | |
| | | | | | | | D | | | | | | | | | L | | | | | | | | | | | | F | | |
| | | | | | | | D | | | | | | | | | L | | | | | | | | | | | | F | | |
| | | | | | | | D | A | | | | | | | | L | | | | | | | | | | | | F | | |
| | | | | | | | D | | | S | | | | | | L | | | | | | | | | | | | F | | |
| | | | | | | | D | | | | | | G | | | L | | | | | | | | | | | | F | | |
| | | | | | | | D | | | | | | | G | | L | | | | | | | | | | | | F | | |
| E | S | | | | | | D | | | | | | G | G | | L | | | | | | | | | | | | F | | |
| | S | V | | | | | | | D | | | | R | | | V | | | | | | | | | | | | F | | |
| | | V | | A | | | | | D | | | | R | | | V | | | | | | | | | | | | F | | |
| | | V | | | | | | A | D | | | | R | | | V | | | | | | | | | | | | F | | |
| | | V | | | | | | | D | S | | | R | | | V | | | | | | | | | | | | F | | |
| | | V | | | | | | | D | | | | R | G | | V | | | | | | | | | | | | F | | |
| E | | V | | | | | | A | D | | | | R | G | | V | | | | | | | | | | | | F | | |
| | | V | | | | | | | D | | | | R | | | V | S | Y | S | T | | | P | K | | | | F | | |
| E | | V | | | | | | A | D | | | | R | G | | V | S | Y | S | T | | | P | K | | | | F | | |
| E | | V | | | | | | A | D | | | | R | G | | V | S | Y | S | T | | | P | K | | | | F | | |
| | | V | | | | | | | D | | | | R | | | V | S | Y | S | T | | | P | K | | | | F | | |
| | | V | | | | | | | D | | | | R | | | V | S | Y | S | T | | | P | K | | | | F | | |

| | 2A8 LC | | | | | | | | | | | | hTFPI | | mTFPI | |
|---|---|---|---|---|---|---|---|---|---|---|---|---|---|---|---|---|
| | Y49 | N51 | N52 | G56 | E80 | S89 | D91 | D92 | G93 | V94 | P95 | V96 | variant/HC_K99L | error | variant/HC_K99L | error |
| | | V | | | | | | | | | | | 8.1# | 0.4 | 2.2# | 0.4 |
| | | | G | | | | | | | | | | 6.2# | 1.4 | 2.3# | 0.8 |
| | | V | | | | | | | | | | | 8.0# | 0.5 | 2.7# | 0.4 |
| | | | | | | | K | | | | | | 5.0# | 0.6 | 3.1# | 0.5 |
| | | | | | | | L | | | | | W | 22.5# | 1.6 | 5.9# | 1.3 |
| | | | | | | | W | | | | | | 0.8# | 0.1 | 0.2# | 0.0 |
| | | | G | | | | L | | | | | W | 0.4# | 0.1 | 0.1# | 0.0 |
| | | | | | | | K | | | | | | 0.6# | 0.0 | 0.1# | 0.0 |
| | | V | | | | | | | | | | W | 0.6 | 0.2 | 0.4 | 0.1 |
| | | | | | | | W | | | | | | 6.2 | 1.6 | 5.3 | 1.2 |
| | | | | | | | L | | | | | W | 5.4 | 1.6 | 4.2 | 1.0 |
| | | | | | | | L | | | | | W | 7.1 | 1.9 | 5.4 | 1.3 |
| | | V | | | | | W | | | | | | 6.6 | 0.7 | 5.9 | 0.9 |
| | | V | | | | | L | | | | | W | 10.4 | 1.3 | 8.0 | 1.6 |
| | | V | | | | | W | | | | | | 6.7 | 0.9 | 5.6 | 1.0 |
| | | | | | | | L | | | | | W | 9.2 | 1.0 | 7.0 | 1.9 |
| | | V | | D | | | | | | | | W | 18.8 | 2.1 | 18.7 | 2.6 |
| | | V | | | | | | | | | | | 16.3 | 1.8 | 15.7 | 2.6 |
| | | V | | | | | L | | | | | | 12.2 | 1.1 | 11.7 | 2.2 |
| | | V | | | | | L | | | | | W | 17.8 | 2.1 | 13.4 | 5.4 |
| | | V | | | | | L | | | | | W | 8.7 | 0.9 | 8.2 | 3.9 |
| | | V | | | | | | | | | | | 7.5 | 0.9 | 7.2 | 1.9 |

TABLE 2-continued

Example of multiple amino acid substitutions within 2A8.

| | | | | | | | | | | | | | |
|---|---|---|---|---|---|---|---|---|---|---|---|---|---|
| | V | | | L | | | | | | 8.4 | 0.9 | 6.5 | 1.4 |
| | | | | L | | | | | W | 14.9 | 1.6 | 12.1 | 4.8 |
| | V | | | K | | | | | | 8.6 | 1.0 | 8.2 | 1.4 |
| | V | | | K | | | | | | 4.9 | 0.6 | 3.9 | 0.7 |
| | | | | | | | | | | 3.9 | 0.7 | 4.5 | 0.7 |
| | | | | L | | | | | W | 18.8 | 1.7 | 18.2 | 3.4 |
| | | | | L | | | | | W | 16.4 | 1.5 | 11.9 | 4.0 |
| | V | | | W | | | | | | 19.7 | 2.2 | 17.4 | 3.8 |
| | V | | | W | | | | | | 21.9* | 5.3 | 22.0* | 8.9 |
| | V | | | W | | | | | | 18.7* | 4.2 | 19.0* | 6.8 |
| | V | | | W | | | | | | 20.1* | 6.2 | 19.9* | 7.4 |
| | V | | | W | | | | | | 19.5* | 4.5 | 18.8* | 6.6 |
| | V | | | W | | | | | | 4.1* | 1.1 | 4.1* | 1.5 |
| | V | | | W | | | | | | 22.0* | 5.7 | 23.2* | 9.1 |
| | V | | | W | | | | | | 20.0* | 5.8 | 18.9* | 7.1 |
| | V | | | W | | | | | | 14.0* | 3.4 | 11.2* | 4.4 |
| | V | M | | W | | | | | | 23.1* | 5.5 | 21.2* | 7.5 |
| | V | | A | W | | | | | | 18.6* | 5.0 | 18.2* | 6.8 |
| | V | | | W | S | | | | | 23.9* | 6.3 | 22.8* | 7.6 |
| | V | | | W | | S | | | | 17.0* | 4.0 | 16.5* | 5.9 |
| | V | | | W | | | T | | | 22.8* | 6.4 | 19.9* | 8.0 |
| | V | | | W | | | | V | | 15.7* | 3.9 | 13.7* | 5.1 |
| | V | | A | W | S | S | T | A | | 10.9* | 3.1 | 9.0* | 4.0 |
| | V | | | W | | | | | | 20.9* | 5.3 | 20.3* | 7.4 |
| | V | | | W | | | | | | 17.9* | 4.5 | 19.1* | 6.9 |
| | V | | | W | | | | | | 16.0* | 3.6 | 14.7* | 5.2 |
| | V | | | W | | | | | | 19.6* | 4.9 | 18.1* | 6.8 |
| | V | | | W | | | | | | 11.2* | 2.8 | 11.6* | 4.1 |
| | V | | | W | | | | | | 10.9* | 2.8 | 12.6* | 4.4 |
| | V | | | W | | | | | | 10.1* | 2.7 | 7.9* | 2.7 |
| | V | | | W | | | | | | 21.4* | 5.2 | 18.7* | 7.2 |
| | V | M | A | W | S | S | T | | | 18.3* | 4.6 | 13.3* | 4.3 |
| | V | | | W | | | | | | 11.9* | 2.1 | 9.3* | 2.9 |
| | V | M | A | W | S | S | T | | | 21.4* | 3.6 | 16.8* | 5.8 |
| | V | M | A | W | S | S | T | | | 18.8* | 4.4 | 12.3* | 3.5 |
| | V | M | | W | | | | | | 19.8* | 3.3 | 15.5* | 4.8 |
| | V | M | | W | | | | | | 18.7* | 3.4 | 15.1* | 4.6 |
| | S | | | L | | | | | W | 19.9* | 4.0 | 20.3* | 5.7 |
| | | | A | L | | | | | W | 4.4* | 1.3 | 6.1* | 1.7 |
| | | | | L | S | | | | W | 20.7* | 4.1 | 20.5* | 6.7 |
| | | | | L | | S | | | W | 14.2* | 2.7 | 15.6* | 4.2 |
| | | | | L | | | T | | W | 18.6* | 4.0 | 19.3* | 5.4 |
| | | | | L | | | | V | W | 10.2* | 2.1 | 13.6* | 4.6 |
| | | | | L | | | | | W | 4.0* | 0.9 | 4.6* | 1.3 |
| | | | | L | | | | | W | 3.9* | 1.2 | 3.0* | 1.0 |
| | | | | L | | | | | W | 18.1* | 4.3 | 18.2* | 5.8 |
| | | | | L | | | | | W | 17.8* | 4.2 | 16.9* | 5.0 |
| | | | | L | | | | | W | 13.6* | 2.8 | 10.6* | 3.6 |
| | | | | L | | | | | W | 13.5* | 2.8 | 6.5* | 3.3 |
| | | | | L | | | | | W | 9.0* | 2.0 | 4.7* | 2.3 |
| | | | | L | | | | | W | 16.6* | 3.8 | 9.3* | 4.3 |
| | | | | L | | | | | W | 11.7* | 2.9 | 7.9* | 4.6 |
| | | | | L | | | | | W | 16.2* | 3.9 | 12.1* | 6.0 |
| | | | | L | | | | | W | 12.1* | 2.8 | 7.7* | 3.8 |
| R | S | M | | L | S | | T | | W | 2.2* | 0.9 | 2.4* | 1.4 |
| | S | M | | L | S | | T | | W | 11.4* | 2.7 | 7.1* | 3.6 |
| | | M | | L | S | | T | | W | 9.8* | 2.5 | 5.9* | 2.0 |
| | S | M | | L | S | | T | | W | 19.6* | 3.5 | 21.4* | 9.6 |
| | | M | | L | S | | T | | W | 18.0* | 4.9 | 15.4* | 7.6 |

Provided in Table 3 are several examples of single and/or double amino acid substitutions introduced into the heavy and/or light chain of 4B7. The expression level of the variants was analyzed in quadruples in the quantification ELISA. After normalization to the respective expression level, performance was analyzed in quadruples in the competitive ELISA on human TFPI and in the equilibrium ELISA on murine TFPI followed by determination of variant to wild-type ratios. Errors were calculated by error propagation from the standard deviations.

TABLE 3

Analysis of single and double amino acid substitutions within 4B7.

| | hTFPI | | mTFPI | |
|---|---|---|---|---|
| 4B7 variants | variant/wild-type | error | variant/wild-type | error |
| HC_N32D | 3.8 | 0.7 | 6.0 | 2.9 |
| HC_N32E | 3.2 | 1.0 | 2.1 | 0.3 |
| HC_S33G | 1.5 | 0.3 | 6.5 | 1.2 |
| HC_S57K | 1.7 | 0.4 | 6.5 | 1.1 |
| HC_S57R | 2.0 | 0.4 | 6.6 | 1.4 |
| HC_D62I | 9.8 | 1.6 | 44.4 | 11.6 |
| HC_D62R | 32.3 | 4.5 | 230.2 | 34.1 |

TABLE 3-continued

Analysis of single and double amino acid substitutions within 4B7.

| 4B7 variants | hTFPI variant/wild-type | hTFPI error | mTFPI variant/wild-type | mTFPI error |
|---|---|---|---|---|
| HC_D62L | 6.8 | 1.2 | 22.9 | 6.1 |
| HC_D62Q | 20.6 | 2.8 | 142.5 | 28.0 |
| HC_D62S | 29.3 | 4.3 | 146.5 | 40.4 |
| HC_H103D | 2.4 | 0.4 | 12.9 | 2.0 |
| HC_H103G | 1.4 | 0.3 | 10.7 | 2.0 |
| HC_Y112D | 2.9 | 0.6 | 5.7 | 1.3 |
| LC_S32R | 4.2 | 0.7 | 7.8 | 1.5 |
| LC_S32Y | 2.0 | 0.4 | 6.7 | 1.2 |
| LC_D33F | 5.3 | 1.3 | 7.0 | 2.6 |
| LC_D33R | 3.6 | 0.7 | 7.2 | 1.9 |
| LC_N35I | 3.6 | 0.7 | 7.1 | 1.5 |
| LC_N35L | 2.1 | 1.0 | 6.0 | 1.3 |
| LC_N35T | 5.4 | 1.0 | 3.4 | 1.1 |
| LC_Y37F | 3.6 | 0.7 | 1.9 | 0.6 |
| LC_S57Y | 1.6 | 0.4 | 2.2 | 0.4 |
| LC_S61C | 3.1 | 0.5 | 15.3 | 4.2 |
| LC_D97M | 2.4 | 0.5 | 1.3 | 0.4 |
| LC_D97T | 1.8 | 0.3 | 5.5 | 1.6 |
| HC_N61G | 2.2 | 0.5 | 1.4 | 0.3 |
| HC_D62V | 31.9 | 5.6 | 95.0 | 20.4 |
| HC_D62N | 52.3 | 9.5 | 146.4 | 28.9 |
| HC_H107M | 8.1 | 1.6 | 5.6 | 1.7 |
| LC_F31I | 9.1 | 2.1 | 23.6 | 4.3 |
| LC_F31M | 1.7 | 0.4 | 1.3 | 0.4 |
| LC_N35V LC_G56D | 1.9 | 0.4 | 8.2 | 1.7 |
| LC_N35L LC_G56A | 3.1 | 0.7 | 6.9 | 1.6 |
| LC_D33F LC_Y54F | 4.3 | 0.9 | 7.9 | 1.9 |
| HC_S30R HC_S57K | 1.6 | 0.3 | 6.6 | 1.1 |

TABLE 3-continued

Analysis of single and double amino acid substitutions within 4B7.

| 4B7 variants | hTFPI variant/wild-type | hTFPI error | mTFPI variant/wild-type | mTFPI error |
|---|---|---|---|---|
| HC_N61G HC_D62V | 8.0 | 1.1 | 31.1 | 9.1 |
| HC_H107M LC_F31I | 1.7 | 0.7 | 9.2 | 2.7 |
| HC_G109A LC_D33R | 3.8 | 0.6 | 8.0 | 1.3 |
| HC_N61T LC_G167C | 2.8 | 0.4 | 6.4 | 1.6 |
| HC_K58M HC_D62N | 6.6 | 1.2 | 15.2 | 4.5 |

Provided in Table 4 are some examples of combinations of amino acid substitutions within 4B7 TFPI antibodies. While not every combination is provided in Table 4, it is contemplated that the TFPI antibody may comprise any combination of modifications provided. The expression level of variants was analyzed in quadruples in the quantification ELISA. If not otherwise indicated, variants were normalized to the respective expression level and performance was analyzed in quadruples in the competitive ELISA on human and murine TFPI followed by calculation of variant to reference (HC_D62R) ratios. In cases were a different reference was used and variants were analyzed without prior normalization, values are marked with "*". For these variants, the value listed in the table was calculated by multiplying the ratios variant/alternative reference with alternative reference/HC_D62R. Errors were calculated by error propagation from the standard deviations. nb: no binding detected under assay conditions used.

TABLE 4

Example of multiple amino acid substitutions within 4B7.

| HC_4B7 | | | | | | | | | | LC_4B7 | | | | | | | | | | | |
|---|---|---|---|---|---|---|---|---|---|---|---|---|---|---|---|---|---|---|---|---|---|
| Q1 | N32 | S37 | G44 | I53 | K55 | D62 | H103 | H107 | Y112 | M4 | V30 | F31 | S32 | D33 | N35 | T36 | Y37 | N39 | L42 | K44 | Q50 |
| | D | | | | | R | | | D | | | | R | | I | | | | | | |
| | D | | | | | R | | M | D | | | I | R | | I | | | | | | |
| | D | | | | | R | | | D | | | | | R | I | | | | | | |
| | D | | | | | S | | M | D | | | | R | R | T | | | | | | |
| | D | | | | | R | D | | | | | I | | R | | | | | | | |
| | | | | | | R | | M | D | | | | | F | I | | | | | | |
| | D | | | | | R | | | D | | | | | F | I | | | | | | |
| | D | | | | | R | | | D | | | I | | F | I | | | | | | |
| | | | | | | R | | M | D | | | M | | F | | | | | | | |
| | | | | | | R | | M | D | | | I | | R | I | | | | | | |
| | D | | | | | R | D | M | D | | | | R | | T | | | | | | |
| | D | | | | | Q | | | D | | | M | R | F | I | | | | | | |
| | D | | | | | R | | | D | | | | R | F | I | | | | | | |
| | D | | | | | R | | M | D | | | | R | F | T | | | | | | |
| | D | | | | | Q | | M | D | | | | | R | T | | | | | | |
| | D | | | | | Q | | M | D | | | | R | | T | | | | | | |
| | D | | | | | R | | M | | | | | R | R | I | | | | | | |
| | D | | | | | R | | M | D | | | I | | R | I | | | | | | |
| | D | | | | | R | | | D | | | M | R | R | I | | | | | | |
| | | | | | | R | | | D | | | | | F | I | | | | | | |
| | D | | | | | R | | M | D | | | I | | R | | | | | | | |
| | D | | | | | R | | M | D | | | M | L | R | I | | | | | | |
| | D | | | | | R | | M | D | | | M | | F | I | | | | | | |
| | D | | | | | Q | | M | D | | | M | R | F | I | | | | | | |
| | D | | | | | R | | | D | | | | | | T | | | | | | |
| | D | | | | | R | | M | D | | | M | | R | | | | | | | |
| | D | | | | | R | | M | D | | | M | | R | I | | | | | | |
| | D | | | | | R | | M | D | | | M | | F | T | | | | | | |
| | | | | | | Q | | | D | | | | R | F | I | | | | | | |
| | D | | | | | Q | | | D | | | | R | R | I | | | | | | |
| | D | | | | | R | | M | D | | | I | | | I | | | | | | |
| | D | | | | | Q | | M | D | | | | R | F | I | | | | | | |
| | D | | | | | Q | | | D | | | I | | F | I | | | | | | |
| | | | | | | R | | M | D | | | M | | F | I | | | | | | |
| | D | | | | | Q | | M | D | | | I | R | R | I | | | | | | |

TABLE 4-continued

Example of multiple amino acid substitutions within 4B7.

| | | | | | | | | | | | | | | | | | | | | | |
|---|---|---|---|---|---|---|---|---|---|---|---|---|---|---|---|---|---|---|---|---|---|
| | | | | | | R | | M | D | | | | | | T | | | | | | |
| | D | | | | | R | | M | D | | | M | R | R | | | | | | | |
| | D | | | | | R | | M | D | | | I | R | F | I | | | | | | |
| | D | | | | | R | D | M | D | | | | R | | | | | | | | |
| | D | | | | | Q | | | D | | | | R | R | I | | | | | | |
| | | | | | | R | | M | D | | | | R | F | I | | | | | | |
| | D | | | | | R | | M | D | | | I | R | F | T | | | | | | |
| | D | | | | | Q | | M | D | | | | R | R | | | | | | | |
| | D | | | | | R | | M | D | | | M | R | R | I | | | | | | |
| | D | | | | | R | | M | D | | | | R | | T | | | | | | |
| | D | | | | | R | | M | D | | | M | R | F | | | | | | | |
| | D | | | | | R | | M | D | | | M | R | R | T | | | | | | |
| | | | | | | S | | M | D | | | | R | F | I | | | | | | |
| | | | | | | R | | M | D | | | I | R | F | I | | | | | | |
| | D | | | | | Q | | M | D | | | M | | F | T | | F | | | | |
| | D | | | | | R | | | D | | | | R | R | | | | | | | |
| | D | | | | | R | | M | D | | | | | F | T | | F | | | | |
| | D | | | | | Q | | M | D | | | | | | I | | | | | | |
| | D | | | | | Q | | M | D | | | | R | F | | | | | | | |
| | D | | | | | R | | M | D | | | | | R | | | | | | | |
| | | | | | | Q | | M | D | | | | | F | I | | | | | | |
| | D | | | | | R | | M | D | | | | | R | I | | | | | | |
| | D | | | | | R | | M | D | | | | R | | T | | | | | | |
| | D | | | | | R | | M | D | | | | | R | T | | | | | | |
| | D | | | | | R | | | D | | | | R | F | I | | | | | | |
| | D | | | | | R | | M | D | | | M | R | F | I | | | | | | |
| | | | | | | R | | | D | | | | R | F | I | | | | | | |
| | D | | | | | R | | | D | L | | | R | F | I | | | | | | |
| | D | | | | | R | | | D | I | | | R | F | I | | | | | | |
| | D | | | | | R | | | D | | L | | R | F | I | | | | | | |
| | D | | | | | R | | | D | | | H | R | F | I | | | | | | |
| | D | | | | | R | | | D | | | Y | R | F | I | | | | | | |
| | D | | | | | R | | | D | | | | R | F | I | N | | | | | |
| | D | | | | | R | | | D | | | | R | F | I | | | D | | | |
| | D | | | | | R | | | D | | | | R | F | I | | | | Q | | |
| | D | | | | | R | | | D | | | | R | F | I | | | | | R | |
| | D | | | | | R | | | D | | | | R | F | I | | | | | | R |
| | D | | | | | R | | | D | | | | R | F | I | | | | | | |
| | D | | | | | R | | | D | | | | R | F | I | | | | | | |
| | D | | | | | R | | | D | | | | R | F | I | | | | | | |
| | D | | | | | R | | | D | | | | R | F | I | | | | | | |
| | D | | | | | R | | | D | | | | R | F | I | | | | | | |
| E | D | | | | | R | | | D | | | | R | F | I | | | | | | |
| | D | N | | | | R | | | D | | | | R | F | I | | | | | | |
| | D | | S | | | R | | | D | | | | R | F | I | | | | | | |
| | D | | | T | | R | | | D | | | | R | F | I | | | | | | |
| | D | | | | Y | R | | | D | | | | R | F | I | | | | | | |
| | D | | | | | K | | | D | | | | R | F | I | | | | | | |
| | D | | | | | Q | | | D | | | | R | F | I | | | | | | |
| E | D | | S | | Y | R | | | D | | L | | R | F | I | N | | | | | |
| | D | | | | | R | | | D | | L | | R | F | I | N | | | | | |
| E | D | | S | | Y | R | | | D | | | | R | F | I | | | | | | |
| | D | | | | | Q | | | D | | L | I | | F | I | | | | | | |
| | D | | | | | Q | | | D | | | I | | F | I | N | | | | | |
| | D | | | | | Q | | | D | | | I | | F | I | | | | Q | | |
| | D | | | | | Q | | | D | | | I | | F | I | | | | | R | |
| | D | | | | | Q | | | D | | | I | | F | I | | | | | | |
| | D | | | | | Q | | | D | | | I | | F | I | | | | | | |
| | D | | | T | | Q | | | D | | | I | | F | I | | | | | | |
| | D | | | | Y | Q | | | D | | | I | | F | I | | | | | | |
| E | D | | S | | Y | R | | | D | | L | | R | | I | N | | | | | |
| | D | | | | | R | | | D | | L | | R | | I | N | | | | | |
| E | D | | S | | Y | R | | | D | | | | R | | I | | | | | | |

| LC_4B7 | | | | | | hTFPI | | mTFPI | |
|---|---|---|---|---|---|---|---|---|---|
| L51 | K55 | G56 | A60 | D97 | S98 | variant/HC_D62R | error | variant/HC_D62R | error |
| | | | | | | 26.1 | 2.2 | 30.1 | 4.3 |
| | | | | T | | 18.2 | 3.6 | 8.7 | 1.4 |
| | | | | | | 22.9 | 2.5 | 19.5 | 3.2 |
| | | | | | | 19.6 | 1.9 | 20.3 | 3.2 |
| | | | | | | 13.6 | 1.4 | 14.6 | 2.4 |
| | | | | | | 20.0 | 3.4 | 36.6 | 9.8 |
| | | | | T | | 25.5 | 1.7 | 15.9 | 2.6 |
| | | | | T | | 23.3 | 3.1 | 11.9 | 2.2 |
| | | | | | | 24.2 | 1.8 | 31.3 | 5.0 |
| | | | | | | 22.0 | 2.2 | 35.4 | 5.0 |

TABLE 4-continued

Example of multiple amino acid substitutions within 4B7.

| | | | | | | | | | | | | | | | |
|---|---|---|---|---|---|---|---|---|---|---|---|---|---|---|---|
| | | | | | | | | | | | | 14.0 | 1.7 | 18.4 | 2.7 |
| | | | | | | | | | | | | 20.8 | 1.6 | 15.8 | 2.1 |
| | | | | | | | | | | | | 29.7 | 2.2 | 42.0 | 5.9 |
| | | | | | | | | | | | | 29.2 | 1.9 | 44.1 | 7.2 |
| | | | | | | | | | | | | 23.7 | 1.4 | 18.8 | 3.2 |
| | | | | | | | | | | | | 25.0 | 2.0 | 27.1 | 5.0 |
| | | | | | | | | | | | | 12.9 | 1.4 | 16.1 | 2.4 |
| | | | | | | | | | | | | 29.8 | 2.9 | 43.0 | 7.0 |
| | | | | | | | | | | | | 15.8 | 1.0 | 11.2 | 2.0 |
| | | | | | | | | | | | | 20.3 | 1.5 | 20.8 | 3.6 |
| | | | | | | | | | | | | 30.1 | 1.6 | 27.9 | 6.9 |
| | | | | | | | | | | | T | 32.2 | 3.1 | 26.7 | 4.5 |
| | | | | | | | | | | | | 28.4 | 2.2 | 46.8 | 7.6 |
| | | | | | | | | | | | T | 19.0 | 1.8 | 12.0 | 2.9 |
| | | | | | | | | | | | T | 26.0 | 3.2 | 9.5 | 2.9 |
| | | | | | | | | | | | | 26.9 | 2.9 | 24.6 | 4.7 |
| | | | | | | | | | | | | 21.3 | 1.8 | 23.0 | 8.6 |
| | | | | | | | | | | | | 29.9 | 2.2 | 34.3 | 5.6 |
| | | | | | | | | | | | | 23.6 | 1.9 | 38.1 | 5.7 |
| | | | | | | | | | | | | 21.4 | 1.5 | 23.5 | 4.4 |
| | | | | | | | | | | | | 28.8 | 2.6 | 30.0 | 5.2 |
| | | | | | | | | | | | | 24.7 | 4.2 | 46.6 | 6.2 |
| | | | | | | | | | | | | 22.4 | 3.0 | 14.0 | 5.6 |
| | | | | | | | | | | | | 30.9 | 3.0 | 47.0 | 7.9 |
| | | | | | | | | | | | T | 20.2 | 1.7 | 11.5 | 1.9 |
| | | | | | | | | | | | T | 20.1 | 2.1 | 19.4 | 3.4 |
| | | | | | | | | | | | | 18.6 | 1.4 | 13.9 | 2.1 |
| | | | | | | | | | | | T | 28.7 | 3.2 | 20.6 | 5.0 |
| | | | | | | | | | | | | 17.7 | 1.4 | 16.0 | 2.9 |
| | | | | | | | | | | | T | 17.2 | 1.0 | 13.4 | 1.9 |
| | | | | | | | | | | | | 24.1 | 2.5 | 50.3 | 6.6 |
| | | | | | | | | | | | | 29.5 | 2.9 | 19.7 | 3.5 |
| | | | | | | | | | | | | 24.9 | 2.3 | 24.7 | 3.2 |
| | | | | | | | | | | | T | 16.9 | 1.5 | 9.6 | 1.7 |
| | | | | | | | | | | | T | 27.7 | 2.5 | 15.8 | 2.5 |
| | | | | | | | | | | | T | 21.9 | 1.7 | 16.5 | 3.7 |
| | | | | | | | | | | | | 17.0 | 2.1 | 18.7 | 2.5 |
| | | | | | | | | | | | | 18.2 | 3.5 | 31.7 | 5.7 |
| | | | | | | | | | | | T | 20.4 | 2.5 | 18.2 | 2.6 |
| | | | | | | | | | | | | 19.4 | 3.2 | 35.3 | 5.6 |
| | | | | | | | | | | | | 14.8 | 2.7 | 7.2 | 1.3 |
| | | | | | | | | | | | | 35.7 | 4.3 | 57.5 | 9.1 |
| | | | | | | | | | | | | 22.2 | 1.6 | 16.4 | 2.5 |
| | | | | | | | | | | | | 23.2 | 1.7 | 16.9 | 3.8 |
| | | | | | | | | | | | | 25.3 | 2.6 | 20.3 | 2.6 |
| | | | | | | | | | | | | 22.7 | 1.4 | 31.7 | 5.1 |
| | | | | | | | | | | | T | 29.1 | 1.8 | 28.1 | 4.9 |
| | | | | | | | | | | | | 25.3 | 2.8 | 29.3 | 4.8 |
| | | | | | | | | | | | | 28.2 | 2.7 | 29.3 | 4.5 |
| | | | | | | | | | | | T | 26.2 | 2.9 | 40.0 | 6.1 |
| | | | | | | | | | | | | 27.0 | 1.5 | 32.3 | 4.9 |
| | | | | | | | | | | | | 21.9 | 2.0 | 39.9 | 5.9 |
| | | | | | | | | | | | T | 21.3* | 6.7 | 23.9* | 4.7 |
| | | | | | | | | | | | T | 19.3* | 5.3 | 12* | 2.8 |
| | | | | | | | | | | | T | 26.1* | 7.6 | 42.2* | 10.1 |
| | | | | | | | | | | | T | 22.1* | 6.8 | 15.2* | 3.2 |
| | | | | | | | | | | | T | 27.9* | 9.8 | 39.7* | 10.4 |
| | | | | | | | | | | | T | 25.2* | 7.6 | 35.4* | 8.8 |
| | | | | | | | | | | | T | 1.3* | 0.5 | nb | 0.0 |
| | | | | | | | | | | | T | 26.9* | 7.6 | 43* | 10.5 |
| | | | | | | | | | | | T | 26* | 8.1 | 40.1* | 9.1 |
| | | | | | | | | | | | T | 25.9* | 7.4 | 39.4* | 10.4 |
| | | | | | | R | | | | | T | 11.2* | 3.6 | 5.2* | 1.5 |
| | | | | | | | L | | | | T | 7.8* | 2.0 | nb | 0.0 |
| | | | | | | | | | V | | T | 12.1* | 3.4 | nb | 0.0 |
| | | | | | | | | | | D | T | 19.1* | 6.2 | 14.3* | 3.6 |
| | | | | | | | | | | | T | H 17.9* | 5.3 | 7.1* | 1.7 |
| | | | | | | | | | | | T | 26.7* | 9.0 | 39.8* | 8.9 |
| | | | | | | | | | | | T | 1.9* | 0.7 | nb | 0.0 |
| | | | | | | | | | | | T | 26.5* | 8.1 | 41.5* | 10.2 |
| | | | | | | | | | | | T | 19.6* | 6.0 | 8.3* | 2.3 |
| | | | | | | | | | | | T | 25.6* | 8.5 | 42.8* | 10.4 |
| | | | | | | | | | | | T | 22.7* | 7.1 | 38.8* | 8.8 |
| | | | | | | | | | | | T | 23.2* | 7.0 | 40* | 8.8 |
| | | | | | | | | | | | T | 20.4* | 5.3 | 29.4* | 6.3 |
| | | | | | | | | | | | T | 23.9* | 4.9 | 28.4* | 8.2 |
| | | | | | | | | | | | T | 26.3* | 4.8 | 45.1* | 9.6 |
| | | | | | | | | | | | | 22.9* | 8.0 | 24.6* | 12.8 |

TABLE 4-continued

Example of multiple amino acid substitutions within 4B7.

| | | | | | |
|---|---|---|---|---|---|
| | | 27.3* | 8.9 | 46.3* | 23.5 |
| | | 21.4* | 6.9 | 16.7* | 8.9 |
| | | 22.8* | 7.9 | 18.5* | 9.6 |
| T | | 14.4* | 4.2 | 4.6* | 2.5 |
| | H | 13.5* | 4.8 | nb | 0.0 |
| | | 5.7* | 1.5 | nb | 0.0 |
| | | 25.6* | 9.0 | 26.2* | 13.3 |
| | | 23* | 5.0 | 9.9* | 3.3 |
| | | 25* | 4.3 | 7* | 4.2 |
| | | 22.6* | 3.9 | 25.5* | 5.8 |

Example 4

Purification of Antibodies

Cells were harvested by centrifugation at 9000 rpm for 30 min at 4° C. and stored at −20° C. Supernatant was buffered-exchanged with buffer A (50 mM $NaH_2PO_4$, 300 mM NaCl, 10 mM imidazole pH8.0), concentrated and purified using a two-step purification procedure. Briefly, 100 ml concentrated supernatant was loaded on a 5 ml Ni-NTA superflow column (Qiagen, 1018142) washed first with 5× column volumes of buffer A followed by 5× column volumes of 4.3% buffer B (50 mM $NaH_2PO_4$, 300 mM NaCl, 250 mM imidazole pH8.0) and eluted with 7 volumes of buffer B. Fractions are combined and dialyzed in PBS. In a second purification step the Ni-NTA purified antibodies were incubated with a light chain-specific affinity matrix, i.e. capture select lambda or kappa (BAC 0849.010 and BAC 0833.10, respectively) for 2A8 and 4B7, respectively. After incubation at 4° C. over night the matrix was loaded into a column, washed with 5 volumes of PBS, 5 volumes of 500 mM arginine 100 mM $NaH_2PO_4$, 100 mM NaCl pH6.0 and again 5 volumes of PBS. Antibodies were eluted with 6 volumes of 100 mM glycine pH3.0 followed by 3 volumes of 100 mM glycine pH2.0 into 1/10 of total volume of 1M HEPES pH 7.5 to neutralize the elutes. Finally, eluates were dialyzed in PBS over night at 4° C. Purified antibodies were analyzed by SDS-PAGE and mass spectrometry.

Example 5

Measure Affinity of Antibody Binding to TFPI Using Surface Plasmon Resonance (Biacore)

Either human or mouse TFPI, was immobilized on the surface for analysis. The CMS-chips and the amine coupling kit (GE HealthCare) were used for the immobilization of the ligand according to the instructions from the manufacturer. The amount of immobilized TFPI was approximately 70 RU to adapt to the mass of antibody that could generate RMax of 100 RU. Parental and affinity matured anti-TFPI antibodies were in the mobile phase. The affinity determination was performed with at least five different concentrations (0.1, 0.4, 1.6, 6.4 and 25 nM) of the purified antibodies.

By analyzing antibody variants that contain single mutations in CDR regions, we identified many clones that had a higher signal in the Elisa binding assay. Selected clones were purified and their affinity to human or mouse TFPI was analyzed using Biacore. As shown in Table 5 and Table 6, these clones have higher affinity to TFPI than do the parental antibodies 2A8 or 4B7. Although some of the 2A8 mutants have slower associate rate (ka) than the parental antibody 2A8, all of these mutants have much slower dissociate rate (kd) than 2A8. Overall, these single mutations increase affinity of 2A8 in the range from 1.47 fold to 7.22 fold on human TFPI, and 1.71 fold to 7.20 fold on mouse TFPI. When we analyzed 4B7 variants, the D62R mutation in heavy chain CDR2 domain significantly increased the signal. This clone was chosen for affinity measurement. As shown in Table 5 and Table 6, this single mutation increases 4B7's affinity to human TFPI from 11.1 nM to 58.2 pM, a 191 fold improvement. The slow dissociate rate (kd) of 4B7HcD62R mainly contributes to its affinity improvement, from $8.40\times10^{-3}$/s of 4B7 to $1.65\times10^{-4}$ of 4B7HcD62R, approximately 50 fold improvement. Similarly, this mutation increases the 4B7's affinity to mouse TFPI from 58.6 nM to 427 pM, a 137-fold improvement.

TABLE 5

Affinity of selected 2A8 or 4B7 variants (single mutation) on human TFPI

| Sample | Clone | ka (1/Ms) | kd (1/s) | KD (M) | Improvement |
|---|---|---|---|---|---|
| 2A8-1 | HC_G33P | 2.71E+06 | 2.24E−03 | 8.27E−10 | 2.70 |
| 2A8-2 | HC_S31P | 2.91E+06 | 3.33E−03 | 1.15E−09 | 1.95 |
| 2A8-3 | HC_S31V | 3.84E+06 | 1.43E−03 | 3.73E−10 | 6.00 |
| 2A8-4 | HC_S35D | 4.01E+06 | 3.80E−03 | 9.50E−10 | 2.35 |
| 2A8-6 | HC_I51E | 1.29E+06 | 1.62E−03 | 1.26E−09 | 1.78 |
| 2A8-7 | HC_S54F | 2.81E+06 | 2.04E−03 | 7.27E−10 | 3.08 |
| 2A8-8 | HC_S55R | 4.30E+06 | 3.94E−03 | 9.17E−10 | 2.44 |
| 2A8-9 | HC_K99L | 2.60E+06 | 8.03E−04 | 3.09E−10 | 7.22 |
| 2A8-10 | HC_K99V | 2.55E+06 | 2.54E−03 | 9.95E−10 | 2.25 |
| 2A8-11 | LC_A32N | 2.70E+06 | 4.10E−03 | 1.52E−09 | 1.47 |
| 2A8-12 | HC_I51D | 3.61E+06 | 4.95E−03 | 1.37E−09 | 1.63 |
| 2A8-13 | LC_N51V | 4.26E+06 | 2.20E−03 | 5.18E−10 | 4.32 |
| 2A8-14 | LC_Y48F | 2.64E+06 | 3.00E−03 | 1.14E−09 | 1.97 |
| 2A8-15 | LC_D91K | 4.33E+06 | 2.09E−03 | 4.82E−10 | 4.64 |
| 2A8-16 | LC_D91L | 4.41E+06 | 4.40E−03 | 9.99E−10 | 2.24 |
| 2A8-17 | LC_D91W | 3.86E+06 | 4.32E−03 | 1.12E−09 | 2.00 |
| 2A8-20 | 2A8wt | 3.13E+06 | 7.00E−03 | 2.24E−09 | 1.00 |
| 4B7HcD62R | HC_D62R | 2.83E+06 | 1.65E−04 | 5.82E−11 | 190.83 |
| 4B7 | 4B7wt | 7.56E+05 | 8.40E−03 | 1.11E−08 | 1.00 |

TABLE 6

Affinity of selected 2A8 and 4B7 variants (single mutation) on mouse TFPI

| Sample | Clone | ka (1/Ms) | kd (1/s) | KD (M) | Improvement |
|---|---|---|---|---|---|
| 2A8-1 | HC_G33P | 9.12E+05 | 1.45E−03 | 1.59E−09 | 2.21 |
| 2A8-2 | HC_S31P | 1.53E+06 | 3.16E−03 | 2.06E−09 | 1.71 |
| 2A8-3 | HC_S31V | 3.39E+06 | 2.02E−03 | 5.95E−10 | 5.91 |
| 2A8-4 | HC_S35D | 1.25E+06 | 2.46E−03 | 1.98E−09 | 1.78 |
| 2A8-7 | HC_S54F | 8.84E+05 | 1.83E−03 | 2.07E−09 | 1.69 |
| 2A8-9 | HC_K99L | 1.56E+06 | 7.59E−04 | 4.88E−10 | 7.20 |
| 2A8-17 | LC_D91W | 2.86E+06 | 2.32E−03 | 8.14E−10 | 4.32 |
| 2A8wt | 2A8wt | 1.47E+06 | 5.17E−03 | 3.51E−09 | 1.00 |

TABLE 6-continued

Affinity of selected 2A8 and 4B7 variants (single mutation) on mouse TFPI

| Sample | Clone | ka (1/Ms) | kd (1/s) | KD (M) | Improvement |
|---|---|---|---|---|---|
| 4B7HcD62R | HC_D62R | 8.58E+06 | 3.67E−03 | 4.27E−10 | 137.00 |
| 4B7wt | 4B7wt | 2.18E+06 | 1.28E−01 | 5.86E−08 | 1.00 |

Next, binding affinity of multiple mutations within 2A8 and 4B7 was investigated. As shown in Table 7(a) and Table 8(a), the mutants of 2A8 that contain multiple mutations in CDR domains have higher affinity than single mutated 2A8 on both human TFPI and mouse TFPI binding. For example, 2A8-200 has 53.7 fold higher affinity than 2A8 on human TFPI binding, and 55.4 fold higher affinity on mouse TFPI binding. As shown in Table 7(b) and Table 8(b), the mutants of 4B7 that contain multiple mutations in CDR domains have higher affinity than single mutated 4B7 on both human TFPI and mouse TFPI binding. Those variants from the parental 2A8 and 4B7 sequences provided in Tables 7 and 8 have also been provided in the sequence listing. SEQ ID NOs: 5-11 correspond to the heavy chain variants of 2A8 listed in Table 7 and 8. SEQ ID NOs: 12-18 correspond to the light chain variants of 2A8. SEQ ID NOs: 19-26 correspond to the heavy chain variants of 4B7 listed in Table 7 and 8. SEQ ID NOs: 27-34 correspond to the light chain variants of 4B7.

TABLE 7(a)

Affinity of selected 2A8 variants (multiple mutations) on human TFPI

| | 2A8 HC | | | | | | | | 2A8 LC | | | | | | | | | | |
|---|---|---|---|---|---|---|---|---|---|---|---|---|---|---|---|---|---|---|---|
| Samples | Q1 | R30 | S31 | S35 | I51 | S55 | S56 | K99 | D1 | I2 | A13 | S21 | R28 | N29 | Y48 | N51 | G56 | E80 | S89 |
| 2A8-127 | | | | D | | | | L | | | | | | | F | V | D | | |
| 2A8-143 | | | | D | | R | | L | | | | | | | F | V | | | |
| 2A8-200 | | | | D | | R | | L | | | | | | | F | V | | | |
| 2A8-216 | | | V | | D | R | | V | | | | | | | F | | | | |
| 2A8-227 | | | | D | | | | L | | | | | | | F | | | | |
| 2A8-g200 | E | S | | D | | R | G | L | S | Y | S | T | P | K | F | V | | M | A |
| 2A8-g216 | | | V | | D | R | | V | S | Y | S | T | P | K | F | S | | M | |
| 2A8 wt | | | | | | | | | | | | | | | | | | | |

| | 2A8 LC | | | | | | | | KD fold |
|---|---|---|---|---|---|---|---|---|---|
| Samples | D91 | D92 | G93 | V94 | V96 | ka (1/Ms) | kd (1/s) | KD (M) | improvement |
| 2A8-127 | | | | | W | 1.68E+06 | 1.41E−04 | 8.41E−11 | 22 |
| 2A8-143 | L | | | | W | 2.88E+06 | 1.05E−04 | 3.64E−11 | 50.9 |
| 2A8-200 | W | | | | | 2.87E+06 | 9.88E−05 | 3.44E−11 | 53.7 |
| 2A8-216 | L | | | | W | 3.29E+06 | 1.54E−04 | 4.67E−11 | 39.6 |
| 2A8-227 | L | | | | W | 3.28E+06 | 1.23E−04 | 3.75E−11 | 49.4 |
| 2A8-g200 | W | S | S | T | | 6.17E+05 | 3.61E−05 | 5.84E−11 | 31.7 |
| 2A8-g216 | L | S | | T | W | 1.45E+06 | 5.29E−05 | 3.65E−11 | 50.7 |
| 2A8 wt | | | | | | 2.05E+06 | 3.80E−03 | 1.85E−09 | 1 |

TABLE 7(B)

Affinity of selected 4B7 variants (multiple mutations) on human TFPI

| | 4B7 HC | | | | | | 4B7 LC | | | | | | | | KD fold |
|---|---|---|---|---|---|---|---|---|---|---|---|---|---|---|---|
| Samples | Q1 | N32 | G44 | K55 | D62 | Y112 | F31 | S32 | D33 | N35 | D97 | ka (1/Ms) | kd (1/s) | KD (M) | improvement |
| B18.5 | | D | | | Q | D | I | | F | I | | 1.23E+06 | 3.18E−05 | 2.60E−11 | 428.2 |
| B2.0 | | D | | | R | D | | R | F | I | T | 7.46E+06 | 3.81E−05 | 5.10E−12 | 2177.8 |
| B27.1 | | D | | | R | D | | | | T | T | 2.78E+06 | 3.53E−05 | 1.27E−11 | 874.9 |
| B32.5 | | | | | R | D | | | F | I | | 2.15E+06 | 3.19E−05 | 1.48E−11 | 748.7 |
| B41.2 | | D | | | R | D | | R | F | I | | 3.46E+06 | 2.47E−05 | 7.16E−12 | 1552.7 |
| B9.7 | | D | | | R | D | | R | | I | | 2.97E+06 | 2.61E−05 | 8.78E−12 | 1266.2 |
| gB9.7 | E | D | S | Y | R | D | | R | | I | | 9.38E+05 | 9.55E−06 | 1.02E−11 | 1091.5 |
| gB9.7-IgG | | D | S | Y | R | D | | R | | I | | 2.03E+06 | 1.56E−05 | 7.65E−12 | 1450.9 |
| 4B7 | | | | | | | | | | | | 7.56E+05 | 8.40E−03 | 1.11E−08 | 1 |

TABLE 8(a)

Affinity of selected 2A8 variants (multiple mutations) on mouse TFPI

| | 2A8 HC | | | | | | | |
|---|---|---|---|---|---|---|---|---|
| Sample | Q1 | R30 | S31 | S35 | I51 | S55 | S56 | K99 |
| 2A8-127 | | | | D | | | | L |
| 2A8-143 | | | | D | | R | | L |
| 2A8-200 | | | | D | | R | | L |
| 2A8-216 | | | V | | D | R | | V |
| 2A8-227 | | | | D | | | | L |
| 2A8-g200 | E | S | | D | | R | G | L |
| 2A8-g216 | | | V | | D | R | | V |
| 2A8 wt | | | | | | | | |

| | 2A8 LC | | | | | | | |
|---|---|---|---|---|---|---|---|---|
| Sample | D1 | I2 | A13 | S21 | R28 | N29 | Y48 | N51 |
| 2A8-127 | | | | | | | F | V |
| 2A8-143 | | | | | | | F | V |
| 2A8-200 | | | | | | | F | V |
| 2A8-216 | | | | | | | F | |
| 2A8-227 | | | | | | | F | |
| 2A8-g200 | S | Y | S | T | P | K | F | V |
| 2A8-g216 | S | Y | S | T | P | K | F | S |
| 2A8 wt | | | | | | | | |

TABLE 8(a)-continued

Affinity of selected 2A8 variants (multiple mutations) on mouse TFPI

| | 2A8 LC | | | | | | | |
|---|---|---|---|---|---|---|---|---|
| Sample | G56 | E80 | S89 | D91 | D92 | G93 | V94 | V96 |
| 2A8-127 | D | | | | | | | W |
| 2A8-143 | | | | L | | | | W |
| 2A8-200 | | | | W | | | | |
| 2A8-216 | | | | L | | | | W |
| 2A8-227 | | | | L | | | | W |
| 2A8-g200 | | M | A | W | S | S | T | |
| 2A8-g216 | | M | | L | S | | T | W |
| 2A8 wt | | | | | | | | |

| Sample | Ka (1/Ms) | Kd (1/s) | KD (M) | KD feld improvement |
|---|---|---|---|---|
| 2A8-127 | 8.24E+05 | 1.47E−03 | 1.78E−10 | 18.5 |
| 2A8-143 | 1.40E+06 | 1.25E−03 | 6.78E−11 | 48.5 |
| 2A8-200 | 1.04E+06 | 6.19E−04 | 5.94E−11 | 55.4 |
| 2A8-216 | 4.19E+06 | 2.16E−04 | 5.15E−11 | 63.9 |
| 2A8-227 | 6.91E+06 | 1.06E−03 | 1.53E−10 | 21.4 |
| 2A8-g200 | 1.15E+06 | 1.39E−04 | 1.21E−10 | 27.3 |
| 2A8-g216 | 9.84E+05 | 7.78E−05 | 7.91E−11 | 41.6 |
| 2A8 wt | 9.40E+05 | 3.10E−03 | 3.29E−09 | 1 |

TABLE 8(B)

Affinity of selected 4B7 variants (multiple mutations) on mouse TFPI

| | 4B7 HC | | | | | | 4B7 LC | | | | | | | | KD fold |
|---|---|---|---|---|---|---|---|---|---|---|---|---|---|---|---|
| Samples | Q1 | N32 | G44 | K55 | D62 | Y112 | F31 | S32 | D33 | N35 | D97 | ka (1/Ms) | kd (1/s) | KD (M) | improvement |
| B18.5 | | D | | | Q | D | I | | F | I | | 1.09E+06 | 4.30E−04 | 3.95E−10 | 138.7 |
| B2.0 | | D | | | R | D | | R | F | I | T | 6.99E+06 | 3.15E−04 | 4.51E−11 | 1213.5 |
| B27.1 | | D | | | R | D | | | | T | T | 4.06E+06 | 7.42E−04 | 1.83E−10 | 299.3 |
| B32.5 | | | | | R | D | | | F | I | | 4.52E+06 | 4.68E−04 | 1.04E−10 | 528.4 |
| B41.2 | | D | | | R | D | | R | F | I | | 4.73E+06 | 2.45E−04 | 5.19E−11 | 1055.7 |
| B9.7 | | D | | | R | D | | R | | I | | 3.59E+06 | 3.34E−04 | 9.31E−11 | 588.2 |
| gB9.7 | E | D | S | Y | R | D | | R | | I | | 9.29E+05 | 1.85E−04 | 1.99E−10 | 275.4 |
| gB9.7-IgG | | D | S | Y | R | D | | R | | I | | 2.70E+06 | 2.36E−05 | 8.75E−12 | 6251.4 |
| 4B7 | | | | | | | | | | | | 3.15E+06 | 1.72E−01 | 5.47E−08 | 1 |

Example 6

Affinity-Improved Antibodies Showed More Potency in Restoring FXa Activity

To determine if affinity-improved anti-TFPI antibodies also improved their potency in restoring FXa activity by blocking the inhibitory effect of TFPI protein, we performed a FXa restoring assay. In this assay, a various indicated amount of the individual affinity-improved antibodies (30 μL) was incubated with the fixed amount of human, mouse or rat recombinant TFPI (20 μL, 6.6 nM) in a total reaction mixture of 50 μl for 30 min at room temperature. After incubation, 50 μL of FXa (3.39 nM) was added to the reaction mixture and incubated at 37° C. for 30 min. Then, 20 μL of Spectrozyme FXa substrate was added to the reaction mixture. After incubation of 12 min, the absorbance of each well was read at 405 nm using a plate reader (Molecular Device). For each experiment, a linear standard curve of the same amount of FXa (3.39 nM) inhibited by known amounts of TFPI was obtained. The 100% restored FXa activity was defined as the FXa activity without adding any amount of TFPI and 0% activity was defined as the FXa activity in the presence of TFPI protein (6.6 nM). The half maximal inhibitory concentration (IC50) was thus calculated for each individual anti-TFPI antibody, some of which are provided in Table 9. The half maximal effective concentration (EC50) was also calculated for selected 2A8 second-round variants and provided in Table 10.

TABLE 9

IC50 and potency improvement for selected anti-TFPI antibodies with single amino acid substitutions using a FXa restoring assay as compared to their parental antibodies, 2A8 and 4B7, respectively.

| Sample | Clone | IC 50 (μg/mL) | Improvement |
|---|---|---|---|
| 2A8-2 | HC_S31P | 0.33 | 1.7 |
| 2A8-3 | HC_S31V | 0.201 | 3.5 |
| 2A8-4 | HC_S35D | 0.55 | 1.1 |
| 2A8-6 | HC_I51E | 0.76 | 0.9 |
| 2A8-7 | HC_S54F | 0.35 | 2.0 |
| 2A8-9 | HC_K99L | 0.181 | 3.9 |
| 2A8-10 | HC_K99V | 0.39 | 1.6 |
| 2A8-14 | LC_Y48F | 0.34 | 1.9 |
| 2A8-15 | LC_D91K | 0.34 | 1.9 |
| 2A8-16 | LC_D91L | 0.37 | 1.7 |
| 2A8-17 | LC_D91W | 0.23 | 3.0 |
| 2A8-20 | 2A8wt | 0.70 | 1.0 |
| 4B7HcD62R | HC_D62R | 0.058 | 25 |
| 4B7 | 4B7wt | 1.46 | 1.0 |

TABLE 10

EC50 and fold improvement for the selected anti-TFPI antibodies having multiple amino acid substitutions as compared to the parental 2A8.

| | 2A8 HC | | | | | 2A8 LC | | | | | EC50 | |
|---|---|---|---|---|---|---|---|---|---|---|---|---|
| Samples | S31 | S35 | I51 | S55 | K99 | Y48 | N51 | G56 | D91 | V96 | (nM) | Improvement |
| 2A8-127 | | D | | | L | F | V | D | | W | 0.44 | 18.2 |
| 2A8-143 | | D | | R | L | F | V | | L | W | 0.50 | 15.8 |
| 2A8-200 | | D | | R | L | F | V | | W | | 0.81 | 9.7 |
| 2A8-216 | V | | D | R | V | F | | | L | W | 1.08 | 7.3 |
| 2A8-9 | | | | | L | | | | | | 1.00 | 7.9 |
| 2A8 wt | | | | | | | | | | | 7.91 | 1.00 |

Example 7

Affinity-Improved Antibodies Showed More Potency in Shortening Clotting Time in a dPT Assay To confirm if these affinity-improved antibodies also improved the potency in shortening clotting time, a dPT is carried out determining the effect of selected affinity-matured antibodies on clotting time using human hemophilia A plasma. The dPT assay is done essentially as described in Welsch et al. (Thrombosis Res., 1991, 64(2): 213-222). Briefly, human hemophilia A plasma (George King Biomedical) is prepared by mixing plasma with 0.1 volumes of control buffer (as a negative control) or indicated anti-TFPI antibodies. After incubation for 30 min at 25° C., each of the prepared plasma samples (100 μL) is combined with 100 μL of appropriately diluted (1:500 dilution) Simplastiu (Biometieux) as a source of thromboplastin and 100 μL of 25 mM calcium chloride. The clotting time is determined using a fibrometer STA4 (Stago) right after adding calcium chloride.

Example 8

Affinity-Improved Antibodies Showed More Potency in Shortening Whole Blood Clotting Time Using Anti-Factor Viii Antibody-Induced Human Hemophilia A Blood To confirm if affinity-improved antibodies show more potency in shortening clotting time, we used a ROTEM system to test the effect of these antibodies on clotting time in human FVIII-neutralizing antibody-induced hemophilia A blood, which mimics the blood from hemophilia A patients with inhibitors. The ROTEM system (Pentapharm GmbH) includes a four-channel instrument, a computer, plasma standards, activators and disposable cups and pins. Thrombelastographic parameters of ROTEM hemostasis systems includes: Clotting Time (CT), which reflects the reaction time (the time required to obtain 2 mm amplitude following the initiation of data collection) to initiate blood clotting; Clot Formation Time (CFT) and the alpha angle to reflect cloning propagation, and the maximum amplitude and the maximum elastic modulus to reflect clot firmness. In a ROTEM assay, 300 μl of freshly drawn citrated whole blood, in which the FVIII activity was neutralized by addition of polyclonal antibodies against FVIII, was used to test the effect of affinity-improved anti-TFPI antibodies as compared to the parental anti-TFPI antibodies. All constituents were reconstituted and mixed according to the manufacturer's instructions, with data collection for the time period required for each system. Briefly, samples were mixed by withdrawing/dispensing 300 μl of blood or plasma with an automated pipette into ROTEM cups with 20 μl of $CaCl_2$ (200 mmol) added, followed immediately by mixing of the sample and initiation of data collection. Data were collected for 2 hours using a computer-controlled (software version 2.96) ROTEM system.

Figure 2:
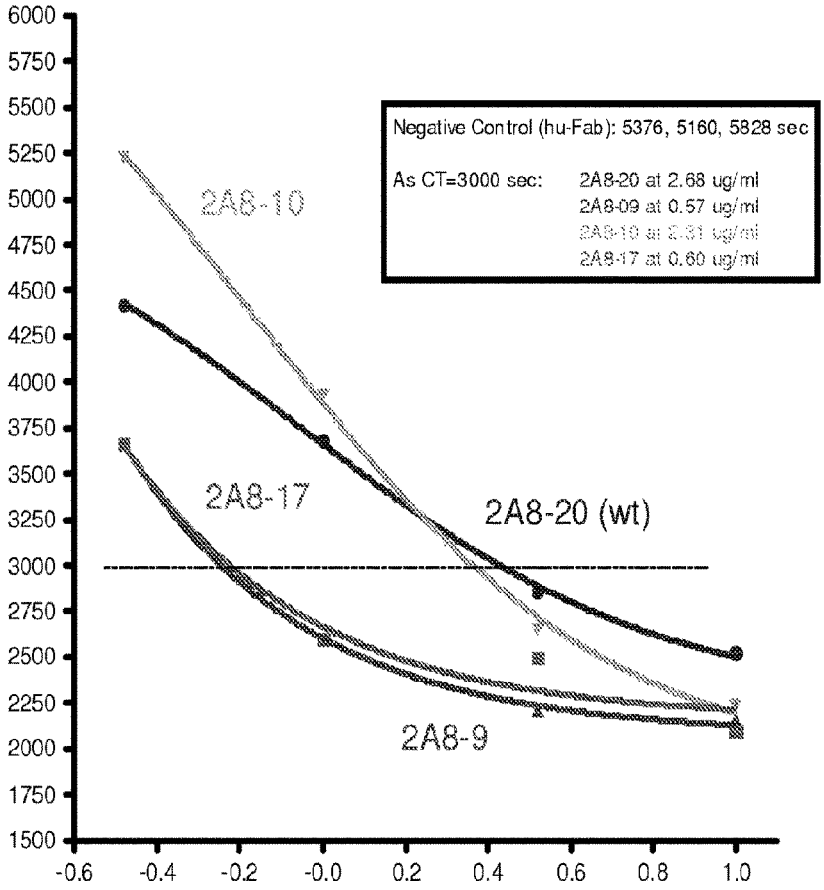
FIG. 2 depicts a graph showing the effect of selected single amino acid mutated anti-TFPI antibodies on clotting time of anti-factor VIII antibody-induced human hemophilic blood.
Figure 3:
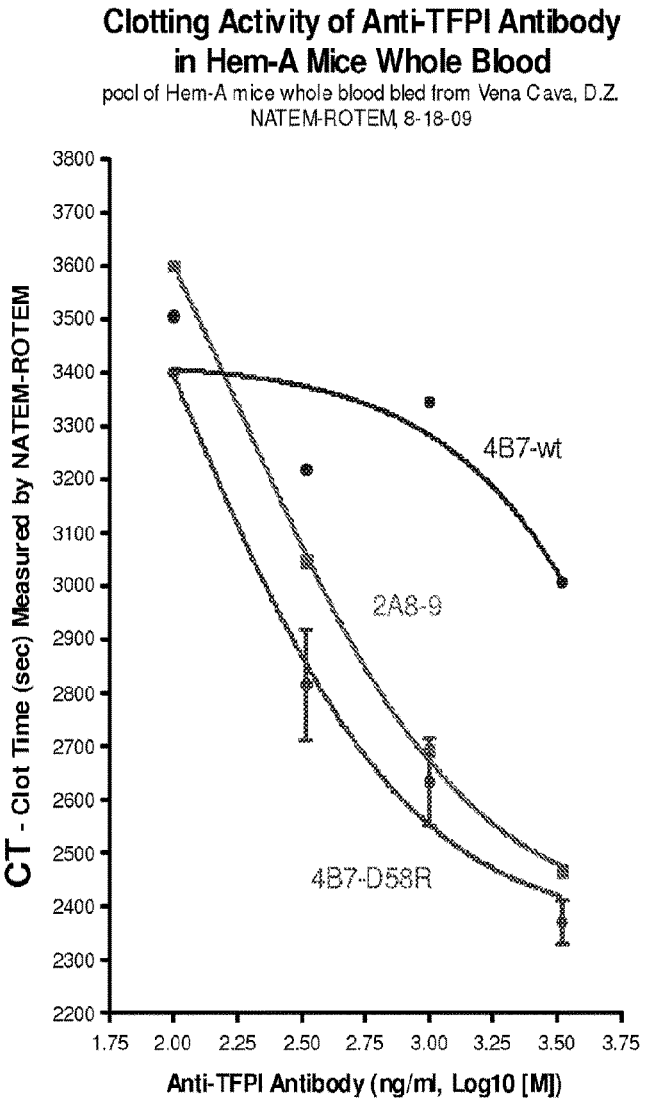
FIG. 3 depicts a graph showing that 4B7-D62R has much more potency in shortening clotting time in human antibody-induced hemophilia A blood as compared to the parental 4B7 antibody and to a less degree, as compared to single amino acid substitutions within 2A8.

An exemplary result of ROTEM assay in detecting the effect of affinity-improved anti-TFPI antibodies in shortening blood clotting time is shown in FIGS. 2 and 3. FIG. 2 shows the effect of selected first round affinity-maturated anti-TFPI antibodies on clotting time of human antibody-induced hemophilia blood. The much affinity-improved antibodies, 2A8-9 and 2A8-17 shows much more potency in shortening clotting time in human antibody-induced hemophilia A blood, whereas 2A8-10, whose binding affinity to TFPI was not improved, remained a similar clotting potency, as compared to the parental 2A8 antibody.

Example 9

Affinity-Improved Antibodies Show Better Survival Rate in a Tail-Vein-Transection Model of Hemophilia A Mice To determine if affinity-improved antibodies are more potency in a protective effect on bleeding mice, a tail-vein-transection model of hemophilia A mice was used. Mice were dosed via tail vein infusion with a various indicated amount of the parental anti-TFPI antibody 2A8 or the various indicated amount of A200, 24 hr prior to the injury.

At 24 hours post-dosing, the left vein of the tail at 2.7 mm from the tip (in diameter) was transected. Survival was observed over 24 hours post transection. Survival rate was demonstrated to be dose-dependent when given with recombinant FVIII (10 IU/kg to 30 IU/kg).

Figure 4:
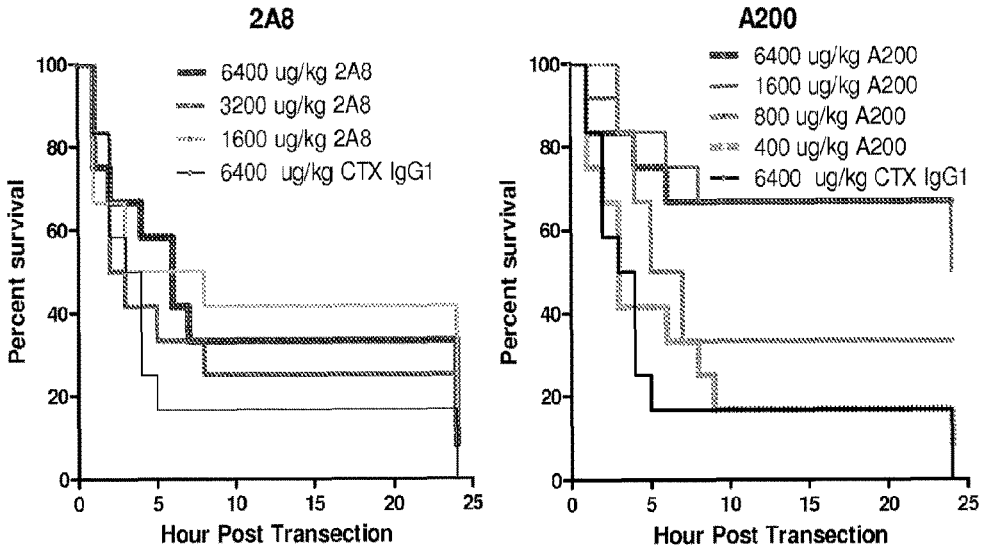
FIG. 4 depicts two graphs showing survival of hemophilia A mice treated with the parental antibody 2A8 and a 2A8 variant having multiple amino acid substitutions (A200) in a dose-dependent manner as compared to control mouse IgG1 (CTX IgG1).

FIG. 4 shows that a selected affinity-improved antibody A200 significantly prolonged the survival of hemophilia A mice in a dose-dependent manner as compared to control mouse IgG1 (CTX IgG1), and displayed a better survival rate than the parental antibody 2A8 at each of the equivalent doses.

Example 10

Figure 5:
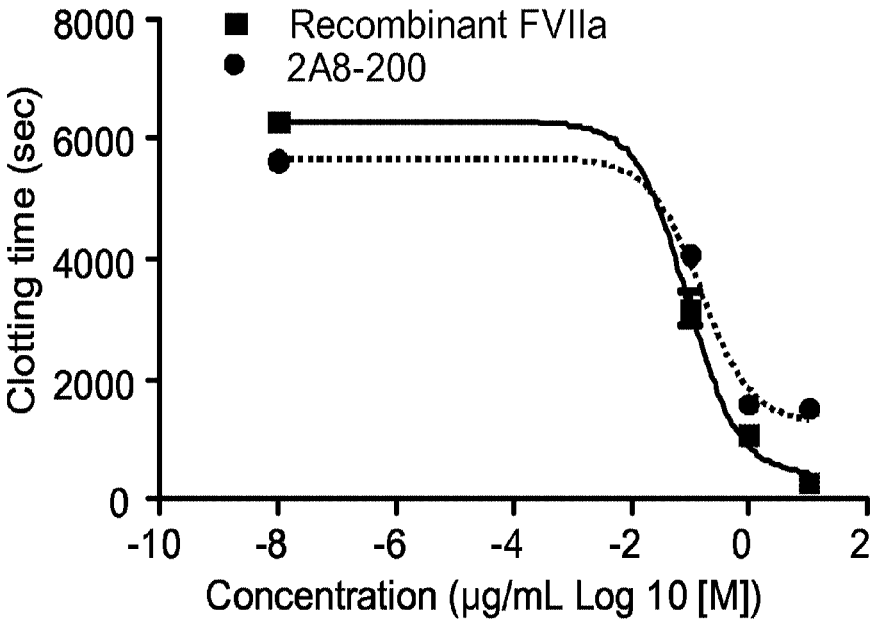
FIG. 5 depicts a graph showing that a 2A8 variant enhanced clotting in human hemophilia C (FXI-deficient) plasma in a dose-dependent manner and its effects were comparable to those of recombinant FVIIa.

Affinity-Improved Antibodies Showed Enhanced Clotting Using Human Hemophilia C (FXI-Deficient) Plasma Further, a ROTEM assay was utilized to test the effect of the antibodies on clotting time in human Factor XI deficient (FXI-deficient) plasma, which mimics the hemophilia C patients. The result of this ROTEM assay in detecting the effect of affinity-improved anti-TFPI antibodies in shortening plasma clotting time is shown in FIG. 5. FIG. 5 shows that a 2A8 variant. 2A8-200, enhanced clotting in human hemophilia C plasma in a dose-dependent manner and its effects are comparable to those of recombinant FVIIa.

While the present invention has been described with reference to the specific embodiments and examples, it should be understood that various modifications and changes may be made and equivalents may be substituted without departing from the true spirit and scope of the invention. The specification and examples are, accordingly, to be regarded in an illustrative rather then a restrictive sense. Furthermore, all articles, books, patent applications and patents referred to herein are incorporated herein by reference in their entireties.

SEQUENCE LISTING

```
<160> NUMBER OF SEQ ID NOS: 46

<210> SEQ ID NO 1
<211> LENGTH: 117
<212> TYPE: PRT
<213> ORGANISM: Homo sapiens

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Ser Trp Val Arg Gln Ala Pro Gly Lys Gly Leu Glu Trp Val
        35                  40                  45

Ser Ser Ile Arg Gly Ser Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Tyr Arg Tyr Trp Phe Asp Tyr Trp Gly Gln Gly Thr Leu
            100                 105                 110

Val Thr Val Ser Ser
        115


<210> SEQ ID NO 2
<211> LENGTH: 108
<212> TYPE: PRT
<213> ORGANISM: Homo sapiens

<400> SEQUENCE: 2

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Tyr
        35                  40                  45

Tyr Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
```

```
65                  70                  75                  80

Asp Glu Ala Asp Tyr Tyr Cys Gln Ser Trp Asp Asp Gly Val Pro Val
                85                  90                  95

Phe Gly Gly Gly Thr Lys Leu Thr Val Leu Gly Gln
            100                 105


<210> SEQ ID NO 3
<211> LENGTH: 123
<212> TYPE: PRT
<213> ORGANISM: Homo sapiens

<400> SEQUENCE: 3

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Tyr
            100                 105                 110

Trp Gly Gln Gly Thr Leu Val Thr Val Ser Ser
        115                 120


<210> SEQ ID NO 4
<211> LENGTH: 114
<212> TYPE: PRT
<213> ORGANISM: Homo sapiens

<400> SEQUENCE: 4

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Ser
            20                  25                  30

Asp Gly Asn Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr


<210> SEQ ID NO 5
<211> LENGTH: 117
<212> TYPE: PRT
<213> ORGANISM: Artificial
<220> FEATURE:
<223> OTHER INFORMATION: Variant
```

<400> SEQUENCE: 5

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser Tyr
20 25 30

Gly Met Asp Trp Val Arg Gln Ala Pro Gly Lys Gly Leu Glu Trp Val
35 40 45

Ser Ser Ile Arg Gly Ser Ser Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Leu Tyr Arg Tyr Trp Phe Asp Tyr Trp Gly Gln Gly Thr Leu
100 105 110

Val Thr Val Ser Ser
115

<210> SEQ ID NO 6
<211> LENGTH: 117
<212> TYPE: PRT
<213> ORGANISM: Artificial
<220> FEATURE:
<223> OTHER INFORMATION: Variant

<400> SEQUENCE: 6

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser Tyr
20 25 30

Gly Met Asp Trp Val Arg Gln Ala Pro Gly Lys Gly Leu Glu Trp Val
35 40 45

Ser Ser Ile Arg Gly Ser Arg Ser Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Leu Tyr Arg Tyr Trp Phe Asp Tyr Trp Gly Gln Gly Thr Leu
100 105 110

Val Thr Val Ser Ser
115

<210> SEQ ID NO 7
<211> LENGTH: 117
<212> TYPE: PRT
<213> ORGANISM: Artificial
<220> FEATURE:
<223> OTHER INFORMATION: Variant

<400> SEQUENCE: 7

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Ser Tyr
20 25 30

Gly Met Asp Trp Val Arg Gln Ala Pro Gly Lys Gly Leu Glu Trp Val
35 40 45

```
Ser Ser Ile Arg Gly Ser Arg Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser
        115


<210> SEQ ID NO 8
<211> LENGTH: 117
<212> TYPE: PRT
<213> ORGANISM: Artificial
<220> FEATURE:
<223> OTHER INFORMATION: Variant

<400> SEQUENCE: 8

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Val Tyr
            20                  25                  30

Gly Met Ser Trp Val Arg Gln Ala Pro Gly Lys Gly Leu Glu Trp Val
        35                  40                  45

Ser Ser Asp Arg Gly Ser Arg Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Arg Tyr Trp Phe Asp Tyr Trp Gly Gln Gly Thr Leu
            100                 105                 110

Val Thr Val Ser Ser
        115


<210> SEQ ID NO 9
<211> LENGTH: 117
<212> TYPE: PRT
<213> ORGANISM: Artificial
<220> FEATURE:
<223> OTHER INFORMATION: Variant

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met Asp Trp Val Arg Gln Ala Pro Gly Lys Gly Leu Glu Trp Val
        35                  40                  45

Ser Ser Ile Arg Gly Ser Ser Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110
```

Val Thr Val Ser Ser
        115

<210> SEQ ID NO 10
<211> LENGTH: 117
<212> TYPE: PRT
<213> ORGANISM: Artificial
<220> FEATURE:
<223> OTHER INFORMATION: Variant

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Asp Trp Val Arg Gln Ala Pro Gly Lys Gly Leu Glu Trp Val
        35                  40                  45

Ser Ser Ile Arg Gly Ser Arg Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Tyr Arg Tyr Trp Phe Asp Tyr Trp Gly Gln Gly Thr Leu
            100                 105                 110

Val Thr Val Ser Ser
        115

<210> SEQ ID NO 11
<211> LENGTH: 117
<212> TYPE: PRT
<213> ORGANISM: Artificial
<220> FEATURE:
<223> OTHER INFORMATION: Variant

<400> SEQUENCE: 11

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Val Tyr
            20                  25                  30

Gly Met Ser Trp Val Arg Gln Ala Pro Gly Lys Gly Leu Glu Trp Val
        35                  40                  45

Ser Ser Asp Arg Gly Ser Arg Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Tyr Arg Tyr Trp Phe Asp Tyr Trp Gly Gln Gly Thr Leu
            100                 105                 110

Val Thr Val Ser Ser
        115

<210> SEQ ID NO 12
<211> LENGTH: 108
<212> TYPE: PRT
<213> ORGANISM: Artificial
<220> FEATURE:
<223> OTHER INFORMATION: Variant

<400> SEQUENCE: 12

Asp Ile Glu Leu Thr Gln Pro Pro Ser Val Ser Val Ala Pro Gly Gln
1 5 10 15

Thr Ala Arg Ile Ser Cys Ser Gly Asp Asn Leu Arg Asn Tyr Tyr Ala
20 25 30

His Trp Tyr Gln Gln Lys Pro Gly Gln Ala Pro Val Val Val Ile Phe
35 40 45

Tyr Asp Val Asn Arg Pro Ser Asp Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gln Ser Trp Asp Asp Gly Val Pro Trp
85 90 95

Phe Gly Gly Gly Thr Lys Leu Thr Val Leu Gly Gln
100 105

<210> SEQ ID NO 13
<211> LENGTH: 108
<212> TYPE: PRT
<213> ORGANISM: Artificial
<220> FEATURE:
<223> OTHER INFORMATION: Variant

<400> SEQUENCE: 13

Asp Ile Glu Leu Thr Gln Pro Pro Ser Val Ser Val Ala Pro Gly Gln
1 5 10 15

Thr Ala Arg Ile Ser Cys Ser Gly Asp Asn Leu Arg Asn Tyr Tyr Ala
20 25 30

His Trp Tyr Gln Gln Lys Pro Gly Gln Ala Pro Val Val Val Ile Phe
35 40 45

Tyr Asp Val Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

Asp Glu Ala Asp Tyr Tyr Cys Gln Ser Trp Leu Asp Gly Val Pro Trp
85 90 95

Phe Gly Gly Gly Thr Lys Leu Thr Val Leu Gly Gln
100 105

<210> SEQ ID NO 14
<211> LENGTH: 108
<212> TYPE: PRT
<213> ORGANISM: Artificial
<220> FEATURE:
<223> OTHER INFORMATION: Variant

<400> SEQUENCE: 14

Asp Ile Glu Leu Thr Gln Pro Pro Ser Val Ser Val Ala Pro Gly Gln
1 5 10 15

Thr Ala Arg Ile Ser Cys Ser Gly Asp Asn Leu Arg Asn Tyr Tyr Ala
20 25 30

His Trp Tyr Gln Gln Lys Pro Gly Gln Ala Pro Val Val Val Ile Phe
35 40 45

Tyr Asp Val Asn Arg Pro Ser Gly Ile Pro Glu Arg Phe Ser Gly Ser
50 55 60

Asn Ser Gly Asn Thr Ala Thr Leu Thr Ile Ser Gly Thr Gln Ala Glu
65 70 75 80

```
Asp Glu Ala Asp Tyr Tyr Cys Gln Ser Trp Trp Asp Gly Val Pro Val
                85                  90                  95

Phe Gly Gly Gly Thr Lys Leu Thr Val Leu Gly Gln
            100                 105


<210> SEQ ID NO 15
<211> LENGTH: 108
<212> TYPE: PRT
<213> ORGANISM: Artificial
<220> FEATURE:
<223> OTHER INFORMATION: Variant

<400> SEQUENCE: 15

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Phe
        35                  40                  45

Tyr Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Leu Asp Gly Val Pro Trp
                85                  90                  95

Phe Gly Gly Gly Thr Lys Leu Thr Val Leu Gly Gln
            100                 105


<210> SEQ ID NO 16
<211> LENGTH: 108
<212> TYPE: PRT
<213> ORGANISM: Artificial
<220> FEATURE:
<223> OTHER INFORMATION: Variant

<400> SEQUENCE: 16

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Arg Asn Tyr Tyr Ala
            20                  25                  30

His Trp Tyr Gln Gln Lys Pro Gly Gln Ala Pro Val Val Val Ile Phe
        35                  40                  45

Tyr Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Trp Leu Asp Gly Val Pro Trp
                85                  90                  95

Phe Gly Gly Gly Thr Lys Leu Thr Val Leu Gly Gln
            100                 105


<210> SEQ ID NO 17
<211> LENGTH: 108
<212> TYPE: PRT
<213> ORGANISM: Artificial
<220> FEATURE:
<223> OTHER INFORMATION: Variant

<400> SEQUENCE: 17
```

```
Ser Tyr Glu Leu Thr Gln Pro Pro Ser Val Ser Val Ser Pro Gly Gln
1               5                   10                  15

Thr Ala Arg Ile Thr Cys Ser Gly Asp Asn Leu Pro Lys Tyr Tyr Ala
            20                  25                  30

His Trp Tyr Gln Gln Lys Pro Gly Gln Ala Pro Val Val Val Ile Phe
        35                  40                  45

Tyr Asp Val Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Trp Ser Ser Thr Pro Val
                85                  90                  95

Phe Gly Gly Gly Thr Lys Leu Thr Val Leu Gly Gln
            100                 105


<210> SEQ ID NO 18
<211> LENGTH: 108
<212> TYPE: PRT
<213> ORGANISM: Artificial
<220> FEATURE:
<223> OTHER INFORMATION: Variant

<400> SEQUENCE: 18

Ser Tyr Glu Leu Thr Gln Pro Pro Ser Val Ser Val Ser Pro Gly Gln
1               5                   10                  15

Thr Ala Arg Ile Thr Cys Ser Gly Asp Asn Leu Pro Lys Tyr Tyr Ala
            20                  25                  30

His Trp Tyr Gln Gln Lys Pro Gly Gln Ala Pro Val Val Val Ile Phe
        35                  40                  45

Tyr Asp Ser Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ser Trp Leu Ser Gly Thr Pro Trp
                85                  90                  95

Phe Gly Gly Gly Thr Lys Leu Thr Val Leu Gly Gln
            100                 105


<210> SEQ ID NO 19
<211> LENGTH: 123
<212> TYPE: PRT
<213> ORGANISM: Artificial
<220> FEATURE:
<223> OTHER INFORMATION: Variant

<400> SEQUENCE: 19

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Gln Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95
```

```
Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120


<210> SEQ ID NO 20
<211> LENGTH: 123
<212> TYPE: PRT
<213> ORGANISM: Artificial
<220> FEATURE:
<223> OTHER INFORMATION: Variant

<400> SEQUENCE: 20

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120


<210> SEQ ID NO 21
<211> LENGTH: 123
<212> TYPE: PRT
<213> ORGANISM: Artificial
<220> FEATURE:
<223> OTHER INFORMATION: Variant

<400> SEQUENCE: 21

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120


<210> SEQ ID NO 22
<211> LENGTH: 123
<212> TYPE: PRT
```

<213> ORGANISM: Artificial
<220> FEATURE:
<223> OTHER INFORMATION: Variant

<400> SEQUENCE: 22

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asn
20 25 30

Ser Ala Ala Trp Ser Trp Ile Arg Gln Ser Pro Gly Arg Gly Leu Glu
35 40 45

Trp Leu Gly Ile Ile Tyr Lys Arg Ser Lys Trp Tyr Asn Arg Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Trp His Ser Asp Lys His Trp Gly Phe Asp Asp
100 105 110

Trp Gly Gln Gly Thr Leu Val Thr Val Ser Ser
115 120

<210> SEQ ID NO 23
<211> LENGTH: 123
<212> TYPE: PRT
<213> ORGANISM: Artificial
<220> FEATURE:
<223> OTHER INFORMATION: Variant

<400> SEQUENCE: 23

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asp
20 25 30

Ser Ala Ala Trp Ser Trp Ile Arg Gln Ser Pro Gly Arg Gly Leu Glu
35 40 45

Trp Leu Gly Ile Ile Tyr Lys Arg Ser Lys Trp Tyr Asn Arg Tyr Ala
50 55 60

Val Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Trp His Ser Asp Lys His Trp Gly Phe Asp Asp
100 105 110

Trp Gly Gln Gly Thr Leu Val Thr Val Ser Ser
115 120

<210> SEQ ID NO 24
<211> LENGTH: 123
<212> TYPE: PRT
<213> ORGANISM: Artificial
<220> FEATURE:
<223> OTHER INFORMATION: Variant

<400> SEQUENCE: 24

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Ser Asp
20 25 30

```
Ser Ala Ala Trp Ser Trp Ile Arg Gln Ser Pro Gly Arg Gly Leu Glu
        35                  40                  45

Trp Leu Gly Ile Ile Tyr Lys Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120


<210> SEQ ID NO 25
<211> LENGTH: 123
<212> TYPE: PRT
<213> ORGANISM: Artificial
<220> FEATURE:
<223> OTHER INFORMATION: Variant

<400> SEQUENCE: 25

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Ser Arg Gly Leu Glu
        35                  40                  45

Trp Leu Gly Ile Ile Tyr Tyr Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120


<210> SEQ ID NO 26
<211> LENGTH: 123
<212> TYPE: PRT
<213> ORGANISM: Artificial
<220> FEATURE:
<223> OTHER INFORMATION: Variant

<400> SEQUENCE: 26

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asp
            20                  25                  30

Ser Ala Ala Trp Ser Trp Ile Arg Gln Ser Pro Ser Arg Gly Leu Glu
        35                  40                  45

Trp Leu Gly Ile Ile Tyr Tyr Arg Ser Lys Trp Tyr Asn Arg Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
```

```
                85                  90                  95

Tyr Tyr Cys Ala Arg Trp His Ser Asp Lys His Trp Gly Phe Asp Asp
            100                 105                 110

Trp Gly Gln Gly Thr Leu Val Thr Val Ser Ser
        115                 120


<210> SEQ ID NO 27
<211> LENGTH: 114
<212> TYPE: PRT
<213> ORGANISM: Artificial
<220> FEATURE:
<223> OTHER INFORMATION: Variant

<400> SEQUENCE: 27

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ile Ser
            20                  25                  30

Phe Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr


<210> SEQ ID NO 28
<211> LENGTH: 114
<212> TYPE: PRT
<213> ORGANISM: Artificial
<220> FEATURE:
<223> OTHER INFORMATION: Variant

<400> SEQUENCE: 28

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Arg
            20                  25                  30

Phe Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Thr Ser Tyr Pro Leu Thr Phe Gly Gln Gly Thr Lys Val Glu Ile Lys
            100                 105                 110

Arg Thr


<210> SEQ ID NO 29
<211> LENGTH: 114
<212> TYPE: PRT
<213> ORGANISM: Artificial
```

<220> FEATURE:
<223> OTHER INFORMATION: Variant

<400> SEQUENCE: 29

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Val Phe Ser
20 25 30

Asp Gly Thr Thr Tyr Leu Asn Trp Tyr Leu Gln Lys Pro Gly Gln Ser
35 40 45

Pro Gln Leu Leu Ile Tyr Lys Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Gln Gln Tyr
85 90 95

Thr Ser Tyr Pro Leu Thr Phe Gly Gln Gly Thr Lys Val Glu Ile Lys
100 105 110

Arg Thr

<210> SEQ ID NO 30
<211> LENGTH: 114
<212> TYPE: PRT
<213> ORGANISM: Artificial
<220> FEATURE:
<223> OTHER INFORMATION: Variant

<400> SEQUENCE: 30

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Val Phe Ser
20 25 30

Phe Gly Ile Thr Tyr Leu Asn Trp Tyr Leu Gln Lys Pro Gly Gln Ser
35 40 45

Pro Gln Leu Leu Ile Tyr Lys Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Gln Gln Tyr
85 90 95

Asp Ser Tyr Pro Leu Thr Phe Gly Gln Gly Thr Lys Val Glu Ile Lys
100 105 110

Arg Thr

<210> SEQ ID NO 31
<211> LENGTH: 114
<212> TYPE: PRT
<213> ORGANISM: Artificial
<220> FEATURE:
<223> OTHER INFORMATION: Variant

<400> SEQUENCE: 31

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Val Phe Arg
20 25 30

Phe Gly Ile Thr Tyr Leu Asn Trp Tyr Leu Gln Lys Pro Gly Gln Ser
35 40 45

```
Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr


<210> SEQ ID NO 32
<211> LENGTH: 114
<212> TYPE: PRT
<213> ORGANISM: Artificial
<220> FEATURE:
<223> OTHER INFORMATION: Variant

<400> SEQUENCE: 32

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Arg
            20                  25                  30

Asp Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110

Arg Thr


<210> SEQ ID NO 33
<211> LENGTH: 114
<212> TYPE: PRT
<213> ORGANISM: Artificial
<220> FEATURE:
<223> OTHER INFORMATION: Variant

<400> SEQUENCE: 33

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Phe Arg
            20                  25                  30

Asp Gly Ile Thr Tyr Leu Asn Trp Tyr Leu Gln Lys Pro Gly Gln Ser
        35                  40                  45

Pro Gln Leu Leu Ile Tyr Lys Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gln Gln Tyr
                85                  90                  95

Asp Ser Tyr Pro Leu Thr Phe Gly Gln Gly Thr Lys Val Glu Ile Lys
            100                 105                 110
```

Arg Thr

<210> SEQ ID NO 34
<211> LENGTH: 114
<212> TYPE: PRT
<213> ORGANISM: Artificial
<220> FEATURE:
<223> OTHER INFORMATION: Variant

<400> SEQUENCE: 34

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Val Phe Arg
20 25 30

Asp Gly Ile Thr Tyr Leu Asn Trp Tyr Leu Gln Lys Pro Gly Gln Ser
35 40 45

Pro Gln Leu Leu Ile Tyr Lys Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Gln Gln Tyr
85 90 95

Asp Ser Tyr Pro Leu Thr Phe Gly Gln Gly Thr Lys Val Glu Ile Lys
100 105 110

Arg Thr

<210> SEQ ID NO 35
<211> LENGTH: 9
<212> TYPE: PRT
<213> ORGANISM: Homo sapiens
<220> FEATURE:
<221> NAME/KEY: MISC_FEATURE
<223> OTHER INFORMATION: CDR1 region of IgG heavy chain of 2A8 antibody

<400> SEQUENCE: 35

Phe Thr Phe Arg Ser Tyr Gly Met Ser
1 5

<210> SEQ ID NO 36
<211> LENGTH: 17
<212> TYPE: PRT
<213> ORGANISM: Homo sapiens
<220> FEATURE:
<221> NAME/KEY: MISC_FEATURE
<223> OTHER INFORMATION: CDR2 region of human IgG heavy chain of 2A8
antibody

<400> SEQUENCE: 36

Ser Ile Arg Gly Ser Ser Ser Ser Thr Tyr Tyr Ala Asp Ser Val Lys
1 5 10 15

Gly

<210> SEQ ID NO 37
<211> LENGTH: 8
<212> TYPE: PRT
<213> ORGANISM: Homo sapiens
<220> FEATURE:
<221> NAME/KEY: MISC_FEATURE
<223> OTHER INFORMATION: CDR3 region of human IgG heavy chain of 2A8
antibody

<400> SEQUENCE: 37

Lys Tyr Arg Tyr Trp Phe Asp Tyr 1 5

<210> SEQ ID NO 38
<211> LENGTH: 11
<212> TYPE: PRT
<213> ORGANISM: Homo sapiens
<220> FEATURE:
<221> NAME/KEY: MISC_FEATURE
<223> OTHER INFORMATION: CDR1 region of human IgG light chain of 2A8
antibody

<400> SEQUENCE: 38

Ser Gly Asp Asn Leu Arg Asn Tyr Tyr Ala His
1 5 10

<210> SEQ ID NO 39
<211> LENGTH: 8
<212> TYPE: PRT
<213> ORGANISM: Homo sapiens
<220> FEATURE:
<221> NAME/KEY: MISC_FEATURE
<223> OTHER INFORMATION: CDR2 region of IgG light chain of 2A8 antibody

<400> SEQUENCE: 39

Tyr Tyr Asp Asn Asn Arg Pro Ser
1 5

<210> SEQ ID NO 40
<211> LENGTH: 9
<212> TYPE: PRT
<213> ORGANISM: Homo sapiens
<220> FEATURE:
<221> NAME/KEY: MISC_FEATURE
<223> OTHER INFORMATION: CDR3 region of IgG light chain of 2A8 antibody

<400> SEQUENCE: 40

Gln Ser Trp Asp Asp Gly Val Pro Val
1 5

<210> SEQ ID NO 41
<211> LENGTH: 11
<212> TYPE: PRT
<213> ORGANISM: Homo sapiens
<220> FEATURE:
<221> NAME/KEY: MISC_FEATURE
<223> OTHER INFORMATION: CDR1 region of IgG heavy chain of 4B7 antibody

<400> SEQUENCE: 41

Asp Ser Val Ser Ser Asn Ser Ala Ala Trp Ser
1 5 10

<210> SEQ ID NO 42
<211> LENGTH: 18
<212> TYPE: PRT
<213> ORGANISM: Homo sapiens
<220> FEATURE:
<221> NAME/KEY: MISC_FEATURE
<223> OTHER INFORMATION: CDR2 region of IgG heavy chain of 4B7 antibody

<400> SEQUENCE: 42

Ile Ile Tyr Lys Arg Ser Lys Trp Tyr Asn Asp Tyr Ala Val Ser Val
1 5 10 15

Lys Ser

<210> SEQ ID NO 43
<211> LENGTH: 11
<212> TYPE: PRT

-continued

```
<213> ORGANISM: Homo sapiens
<220> FEATURE:
<221> NAME/KEY: MISC_FEATURE
<223> OTHER INFORMATION: CDR3 region of IgG heavy chain of 4B7 antibody

<400> SEQUENCE: 43

Trp His Ser Asp Lys His Trp Gly Phe Asp Tyr
1               5                   10


<210> SEQ ID NO 44
<211> LENGTH: 16
<212> TYPE: PRT
<213> ORGANISM: Homo sapiens
<220> FEATURE:
<221> NAME/KEY: MISC_FEATURE
<223> OTHER INFORMATION: CDR1 region of IgG light chain of 4B7 antibody

<400> SEQUENCE: 44

Arg Ser Ser Gln Ser Leu Val Phe Ser Asp Gly Asn Thr Tyr Leu Asn
1               5                   10                  15


<210> SEQ ID NO 45
<211> LENGTH: 7
<212> TYPE: PRT
<213> ORGANISM: Homo sapiens
<220> FEATURE:
<221> NAME/KEY: MISC_FEATURE
<223> OTHER INFORMATION: CDR2 region of IgG light chain of 4B7 antibody

<400> SEQUENCE: 45

Lys Gly Ser Asn Arg Ala Ser
1               5


<210> SEQ ID NO 46
<211> LENGTH: 9
<212> TYPE: PRT
<213> ORGANISM: Homo sapiens
<220> FEATURE:
<221> NAME/KEY: MISC_FEATURE
<223> OTHER INFORMATION: CDR3 region of IgG light chain of 4B7 antibody

<400> SEQUENCE: 46

Gln Gln Tyr Asp Ser Tyr Pro Leu Thr
1               5
```

We claim:

1. An isolated human monoclonal [IgG] antibody that binds specifically to human tissue factor pathway (TFPI) inhibitor, wherein the antibody comprises [at least] one *or more* amino acid [substitution] *substitutions, comprising*:

(a) a human heavy chain comprising:

a CDR 1 region with the amino acid sequence shown in SEQ ID NO: 41[, optionally comprising a substitution at N32 relative to SEQ ID NO: 3];

a CDR2 region with the amino acid sequence shown in SEQ ID NO: 42[, optionally comprising a substitution selected from the group consisting of K55 and D62 relative to SEQ ID NO: 3];

a CDR3 region that binds specifically to TFPI and has the amino acid sequence shown in SEQ ID NO: 43; [optionally comprising a substitution at Y112 relative to SEQ ID NO: 3, optionally, an amino acid substitution at G44 relative to SEQ ID NO: 3;] and (b) a human light chain comprising:

a CDR1 region with the amino acid sequence shown in SEQ ID NO: 44[, optionally comprising a substitution of a position selected from the group consisting of S32 and N35 and combinations thereof relative to SEQ ID NO: 4];

a CDR2 region with the amino acid sequence shown in SEQ ID NO: 45;

a CDR3 region that binds specifically to TFPI and has the amino acid sequence shown in SEQ ID NO: 46*;*

*wherein the one or more amino acid substitutions is selected from the group consisting of:*

*N32 relative to SEQ ID NO: 3 within the CDR1 region of the human heavy chain;*

*K55 relative to SEQ ID NO: 3 within the CDR2 region of the human heavy chain;*

*D62 relative to SEQ ID NO: 3 within the CDR2 region of the human heavy chain;*

*Y112 relative to SEQ ID NO: 3 within the CDR3 region of the human heavy chain;*

*G44 relative to SEQ ID NO: 3 within the human heavy chain;*

*S32 relative to SEQ ID NO: 4 within CDR1 of the human light chain; and*

*N35 relative to SEQ ID NO: 4 within CDR1 of the human light chain.*

2. An isolated human monoclonal [IgG] antibody that binds specifically to human tissue factor pathway inhibitor (TFPI), wherein the antibody comprises:

(a) a human heavy chain comprising:

a CDR 1 region with the amino acid sequence shown in SEQ ID NO: 41, comprising a substitution of N32 relative to SEQ ID NO: 3, a CDR2 region with the amino acid sequence shown in SEQ ID NO: 42, comprising at least one substitution relative to SEQ ID NO: 3 selected from the group consisting of K55Y and D62R and combinations thereof;

a CDR3 region that binds specifically to TFPI and has the amino acid sequence shown in SEQ ID NO: 43 comprising a substitution [relative to SEQ ID NO: 43] of Y112D relative to SEQ ID NO: 3, and a substitution relative to SEQ ID No. 3 of G44S; and (b) a human light chain comprising:

a CDR1 region with the amino acid sequence shown in SEQ ID NO: 44, comprising at least one substitution selected from the group consisting of S32R and N35I relative to SEQ ID NO: 4 and combinations thereof;

a CDR2 region with the amino acid sequence shown in SEQ ID NO: 45, a CDR3 region that binds specifically to TFPI and has the amino acid sequence shown in SEQ ID NO: 46.

3. The antibody of claim 1, *wherein the antibody comprises the amino acid substitution of N32 relative to SEQ ID NO: 3 within the CDR1 region of the human heavy chain, and* wherein the substitution at N32 is N32D.

4. The antibody of claim 1, *wherein the antibody comprises the amino acid substitution of K55 relative to SEQ ID NO: 3 within the CDR2 region of the heavy chain, and* wherein the substitution of K55 is K55Y.

5. The antibody of claim 1, *wherein the antibody comprises the amino acid substitution of G44 within the human heavy chain, and* wherein the substitution of G44 is G44S.

6. The antibody of claim 1, *wherein the antibody comprises the amino acid substitution of D62 relative to SEQ ID NO: 3 within the CDR2 region of the human heavy chain, and* wherein the substitution of D62 is D62R.

7. The antibody of claim 1, *wherein the antibody comprises the amino acid substitution of Y112 relative to SEQ ID NO: 3 within the CDR3 region of the human heavy chain, and* wherein the substitution of Y112 is Y112D.

8. The antibody of claim 1, *wherein the antibody comprises the amino acid substitution of S32 relative to SEQ ID NO:4 within the CDR1 region of the human light chain, and* wherein the substitution of S32 is S32R.

9. The antibody of claim 1, *wherein the antibody comprises the amino acid substitution of N35 relative to SEQ ID NO: 4 within the CDR1 region of the human light chain, and* wherein the substitution of N35 is N35I.

10. The antibody of claim 1, wherein the amino *acid* at position 1 of the heavy chain relative to SEQ ID NO: 3 is Q.

*11. The antibody of claim 1, wherein the antibody is an IgG antibody.*

*12. A method of treating a subject suffering from hemophilia A or hemophilia B, comprising administering to the subject a therapeutically effective amount of an isolated human monoclonal antibody that binds specifically to human tissue factor pathway (TFPI) inhibitor, wherein the antibody comprises one or more amino acid substitutions, comprising:*

*(a) a human heavy chain comprising:*

*a CDR 1 region with the amino acid sequence shown in SEQ ID NO: 41;*

*a CDR2 region with the amino acid sequence shown in SEQ ID NO: 42;*

*a CDR3 region that binds specifically to TFPI and has the amino acid sequence shown in SEQ ID NO: 43; and*

*(b) a human light chain comprising:*

*a CDR 1 region with the amino acid sequence shown in SEQ ID NO: 44;*

*a CDR2 region with the amino acid sequence shown in SEQ ID NO: 45;*

*a CDR3 region that binds specifically to TFPI and has the amino acid sequence shown in SEQ ID NO: 46;*

*wherein the one or more amino acid substitutions is selected from the group consisting of:*

*N32 relative to SEQ ID NO: 3 within the CDR1 region of the human heavy chain;*

*K55 relative to SEQ ID NO: 3 within the CDR2 region of the human heavy chain;*

*D62 relative to SEQ ID NO: 3 within the CDR2 region of the human heavy chain;*

*Y112 relative to SEQ ID NO: 3 within the CDR3 region of the human heavy chain:*

*G44 relative to SEQ ID NO: 3 within the human heavy chain;*

*S32 relative to SEQ ID NO: 4 within CDR1 of the human light chain; and*

*N35 relative to SEQ ID NO: 4 within CDR1 of the human light chain.*

*13. A method of treating a subject suffering from hemophilia A or hemophilia B, comprising administering to the subject a therapeutically effective amount of an isolated human monoclonal antibody that binds specifically to human tissue factor pathway inhibitor (TFPI), wherein the antibody comprises:*

*(a) a human heavy chain comprising:*

*a CDR1 region with the amino acid sequence shown in SEQ ID NO: 41, comprising a substitution of N32 relative to SEQ ID NO: 3;*

*a CDR2 region with the amino acid sequence shown in SEQ ID NO: 42, comprising at least one substitution selected from the group consisting of K55Y, D62R, and a combination thereof, relative to SEQ ID NO: 3;*

*a CDR3 region that binds specifically to TFPI and has the amino acid sequence shown in SEQ ID NO: 43 comprising a substitution of Y112D relative to SEQ ID NO: 3; and*

*a substitution relative to SEQ ID NO: 3 of G44S; and*

*(b) a human light chain comprising:*

*a CDR1 region with the amino acid sequence shown in SEQ ID NO: 44, comprising at least one substitution selected from the group consisting of S32R, N35I, and a combination thereof, relative to SEQ ID NO: 4;*

*a CDR2 region with the amino acid sequence shown in SEQ ID NO: 45; and*

*a CDR3 region that binds specifically to TFPI and has the amino acid sequence shown in SEQ ID NO: 46.*

*14. The method of claim 12, wherein the subject is suffering from hemophilia A.*

*15. The method of claim 12, wherein the subject is suffering from hemophilia B.*

*16. The method of claim 12, wherein the antibody is an IgG antibody.*

*17. The method of claim 12, wherein the antibody comprises the amino acid substitution of N32 relative to SEQ ID NO: 3 within the CDR1 region of the human heavy chain, and wherein the substitution at N32 is N32D.*

*18. The antibody of claim 12, wherein the antibody comprises the amino acid substitution of K55 relative to SEQ ID NO: 3 within the CDR2 region of the heavy chain, and wherein the substitution of K55 is K55Y.*

*19. The method of claim 12, wherein the antibody comprises the amino acid substitution of G44 within the human heavy chain, and wherein the substitution of G44 is G44S.*

*20. The method of claim 12, wherein the antibody comprises the amino acid substitution of D62 relative to SEQ ID NO: 3 within the CDR2 region of the human heavy chain, and wherein the substitution of D62 is D62R.*

*21. The method of claim 12, wherein the antibody comprises the amino acid substitution of Y112 relative to SEQ ID NO: 3 within the CDR3 region of the human heavy chain, and wherein the substitution of Y112 is Y112D.*

*22. The method of claim 12, wherein the antibody comprises the amino acid substitution of S32 relative to SEQ ID NO: 4 within the CDR1 region of the human light chain, and wherein the substitution of S32 is S32R.*

*23. The method of claim 12, wherein the antibody comprises the amino acid substitution of N35 relative to SEQ ID NO:4 within the CDR1 region of the human light chain, and wherein the substitution of N35 is N35I.*

*24. The antibody of claim 12, wherein the amino acid at position 1 of the heavy chain relative to SEQ ID NO: 3 is Q.*

* * * * *